(12) United States Patent
De Groot et al.

(10) Patent No.: US 7,223,837 B2
(45) Date of Patent: May 29, 2007

(54) ELONGATED AND MULTIPLE SPACERS IN ACTIVATIBLE PRODRUGS

(75) Inventors: Franciscus Marinus Hendrikus De Groot, Nijmegen (NL); Patrick Henry Beusker, Nijmegen (NL); Johannes Wilhelm Scheeren, Malden (NL); Dick De Vos, Oegstgeest (NL); Leonardus Wilhelmus Adriaan Van Berkom, Oss (NL); Guuske Frederike Busscher, Nijmegen (NL); Antoinette Eugenie Seelen, Heerlen (NL); Ralph Koekkoek, Beuningen (NL); Carsten Albrecht, Oss (NL)

(73) Assignee: Syntarga B.V., Nijmegen (NL)

( * ) Notice: Subject to any disclaimer, the term of this patent is extended or adjusted under 35 U.S.C. 154(b) by 0 days.

(21) Appl. No.: 10/472,921

(22) PCT Filed: Mar. 25, 2002

(86) PCT No.: PCT/EP02/03591

§ 371 (c)(1),
(2), (4) Date: Feb. 2, 2004

(87) PCT Pub. No.: WO02/083180

PCT Pub. Date: Oct. 24, 2002

(65) Prior Publication Data

US 2004/0121940 A1 Jun. 24, 2004

(30) Foreign Application Priority Data

Mar. 23, 2001 (EP) .............................. 01201095.5

(51) Int. Cl.
*C07K 5/08* (2006.01)
(52) U.S. Cl. .................. 530/331; 530/330; 514/18; 514/19
(58) Field of Classification Search ............... 530/330, 530/331; 514/2, 18, 19
See application file for complete search history.

(56) References Cited

U.S. PATENT DOCUMENTS

| | | | |
|---|---|---|---|
| 5,691,371 A | | 11/1997 | Denny et al. |
| 6,759,509 B1 * | | 7/2004 | King et al. .................. 530/330 |
| 2003/0096743 A1 * | | 5/2003 | Senter et al. .................. 514/12 |
| 2003/0130189 A1 * | | 7/2003 | Senter et al. .................. 514/12 |
| 2005/0256030 A1 * | | 11/2005 | Feng .............................. 514/2 |

FOREIGN PATENT DOCUMENTS

| | | |
|---|---|---|
| EP | 0624377 | 11/1994 |
| EP | 1243276 | 9/2002 |
| WO | WO 8101145 | 4/1981 |
| WO | WO 9813059 | 4/1998 |

OTHER PUBLICATIONS

Avalos, Martin (Tetrahedron: Asymmetry 6(4), 945-56, 1995).*
Goodwin, (Journal of Organic Chemistry 50(26), 5889-92, 1985).*
PCT/EP02/03591 International Search Report.
Chakravarty et al. "Plasmin-activated prodrugs" J. Med. Chem (1983), 26(5), 368-44.
Dubowchik et al. Cathepsin B-sensitive dipeptide prodrugs. 1 Bioorganic & Medicinal Chemistry Letters, Oxford, GB vol. 8, No. 23, Dec. 1, 1998, pp. 3341-3346.
De Groot et al. "Synthesis and Biological Evaluation of Novel Prodrugs" J. Med. Chem. (1999) 42(25) 5277-5283.
De Groot et al. "Synthesis and Biological Evaluation of 2'-Carbamate-Linked" Journal of Medicinal Chemistry (2000) 43(16), 3093-3102.
De Groot et al. "Elongated Multiple Electronic Cascade" Journal of Organic Chemistry (2001) 66(26), 8815-8830.
De Groot et al. "In vivo efficacy of spacer-containing antitumor prodrugs" Proceedings of the American Association for Cancer Research Annual, vol. 43, Mar. 2002, p. 415.
De Groot et al. "Design, synthesis and initial evaluation" proceedings of the American Association for Cancer Research Annual, vol. 43, Mar. 2002 p. 414.
EPO communication dated Dec. 19, 2005 regarding European Patent Application No. 02727513.0 (claiming priority of European Patent Application No. 01201095.5).

* cited by examiner

Primary Examiner—David Lukton
(74) Attorney, Agent, or Firm—Kilpatrick & Lockhart Preston Gates Ellis LLP

(57) ABSTRACT

This invention is directed to prodrugs that can be activated at the preferred site of action in order to selectively deliver the corresponding therapeutic parent drugs to target cells or to the target site. This invention will therefore primarily but not exclusively relate to tumor cells as target cells. More specifically the prodrugs are compounds of the formula V—$(W)_k$—$(X)_l$—A—Z, wherein: V is a specifier; $(W)_k$—$(X)_l$—A is an elongated self-elimination spacer system; W and X are each a 1,(4+2n) electronic cascade spacer, being the same or different; A is either a spacer group of formula $(Y)_m$ wherein: Y is a 1,(4+2n) electronic cascade spacer, or a group of formula U being a cyclization elimination spacer; Z is a therapeutic drug; k, l and m are integers from 0 (included) to 5 (included); n is an integer of 0 (included) to 10 (included), with the provisos that: —when A is $(Y)_m$: $k+l+m \geq 1$, and if $k+l+m=1$; —when A is U: $k+l \geq 1$.

35 Claims, 14 Drawing Sheets

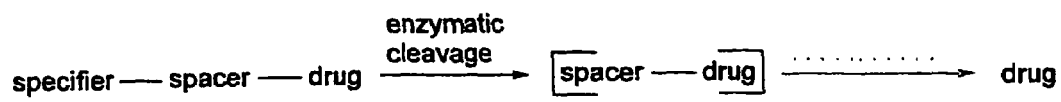
FIG. 1
— (elongated spacer system) — drug
FIG. 2
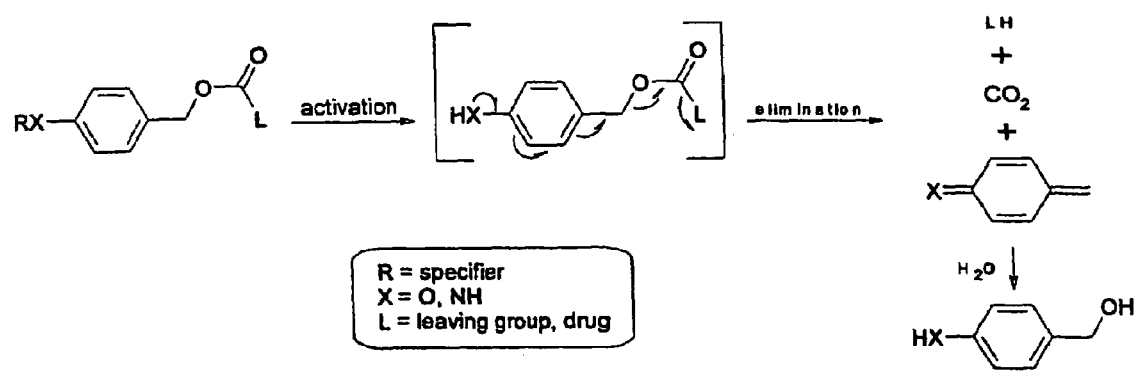
R = specifier
X = O, NH
L = leaving group, drug
FIG. 3 specifier ——— (electronic cascade spacer) ——— (electronic cascade spacer)$_n$ ——— drug
FIG. 11
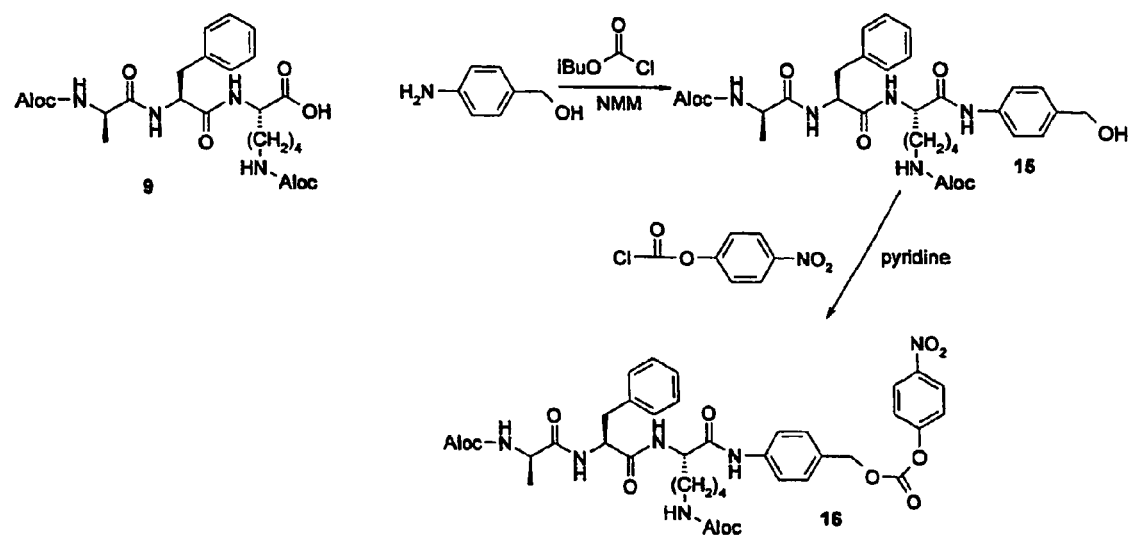
FIG. 12
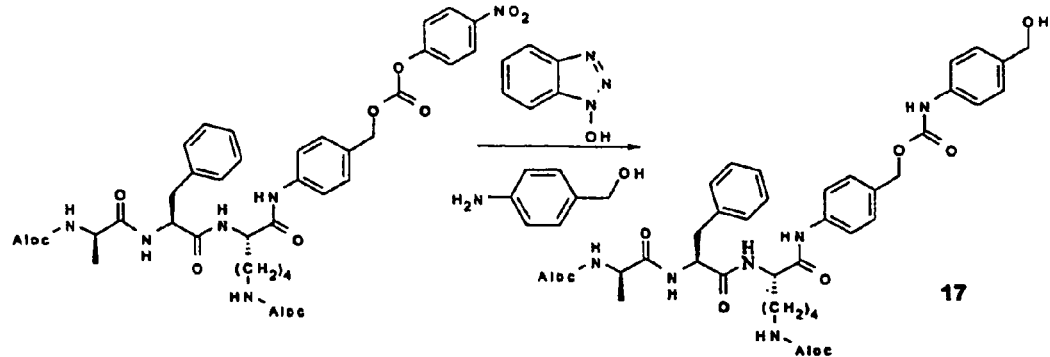
FIG. 13 specifier ——(1,(4 + 2n)-electronic cascade spacer)——(cyclisation spacer)——2'-O-paclitaxel

ELONGATED AND MULTIPLE SPACERS IN ACTIVATIBLE PRODRUGS

CROSS-REFERENCE TO A RELATED APPLICATION

This application claims the priority of EP-A-01201095.5, filed 23 Mar. 2001, publication No. EP 1 243 276, the disclosure thereof being incorporated by reference.

FIELD OF THE INVENTION

This invention is directed to prodrugs that can be activated at the preferred site of action in order to selectively deliver the corresponding therapeutic or diagnostic parent moiety to target cells or to the target site. This invention will therefore primarily but not exclusively relate to tumor cells as target cells.

BACKGROUND OF THE INVENTION

Lack of selectivity of chemotherapeutic agents is a major problem in cancer treatment. Because highly toxic compounds are used in cancer chemotherapy, it is typically associated with severe side effects. Drug concentrations that would completely eradicate the tumor cannot be reached because of dose-limiting side effects such as gastrointestinal tract and bone marrow toxicity. In addition, tumors can develop resistance against anticancer agents after prolonged treatment. In modem drug development, targeting of cytotoxic drugs to the tumor site can be considered one of the primary goals.

A promising approach to obtain selectivity for tumor cells or tumor tissue is to exploit the existence of tumor-associated enzymes. A relatively high level of tumor-specific enzyme can convert a pharmacologically inactive prodrug to the corresponding active parent drug in the vicinity of the tumor. Via this concept a high concentration of toxic anticancer agent can be generated at the tumor site. All tumor cells may be killed if the dose is sufficiently high, which may decrease development of drug resistant tumor cells.

There exist several enzymes that are present at elevated levels in certain tumor tissues. One example is the enzyme β-glucuronidase, which is liberated from certain necrotic tumor areas. Furthermore, several proteolytic enzymes have been shown to be associated with tumor invasion and metastasis. Several proteases, like for example the cathepsins and proteases from the urokinase-type plasminogen activator (u-PA) system are all involved in tumor metastasis. The serine protease plasmin plays a key role in tumor invasion and metastasis. The proteolytically active form of plasmin is formed from its inactive pro-enzyme form plasminogen by u-PA. The tumor-associated presence of plasmin can be exploited for targeting of plasmin-cleavable prodrugs.

In this invention a new technology is disclosed that can be applied to prepare improved prodrugs or conjugates for targeting drugs to disease-related or organ-specific tissue or cells, for example tumor-specific prodrugs. This technology can furthermore find application in (non-specific) controlled release of compounds, with the aim of facilitating release of the parent moiety. The present invention is deemed to be applicable to all drugs that need to be delivered at a specific target site where a specific disease-related biomolecule can convert the prodrug into the drug or induce conversion of the prodrug into the drug.

DESCRIPTION OF THE INVENTION

The technology of this invention relates to novel linker systems to be inserted between a specifier (=part of prodrug to be cleaved by the enzyme) and parent drug. A great number of anticancer prodrugs that have been developed in the past contain a self-eliminating connector or linker, also called self-elimination spacer. This spacer is incorporated between the specifier and the drug in order to facilitate enzymatic cleavage and so enhance the kinetics of drug release (as shown in FIG. 1). The specifier (which for example can be an oligopeptide substrate for a protease or for example a β-glucuronide substrate for β-glucuronidase) must be site-specifically removed, followed by a spontaneous spacer elimination to release the cytotoxic parent drug. In this invention, greatly improved linker systems are disclosed. These are applicable in prodrugs, for example anticancer prodrugs, and significantly enhance enzymatic activation rates.

More specifically, the invention relates to compounds of the formula:

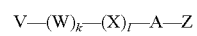

wherein:

V is an enzymatically removable specifier, $(W)_k$—$(X)_l$—A is an elongated self-eliminating spacer system, W and X are each a 1,(4+2n) electronic cascade spacer, being the same or different, A is either a spacer group of formula $(Y)_m$, wherein Y is a 1,(4+2n) electronic cascade spacer, or a group of formula U, being a cyclisation elimination spacer, Z is a therapeutic or diagnostic moiety, k, l and m are independently an integer of 0 (included) to 5 (included), n is an integer of 0 (included) to 10 (included), with the provisos that:

when A is $(Y)_m$: then $k+l+m \geq 1$, and if $k+l+m=1$, then $n>1$;

when A is U: then $k+l \geq 1$.

These novel elongated linker systems show improved enzymatic activation characteristics, which is demonstrated in the following Examples.

An activatible prodrug according to this invention comprises a specifier V, which is meant to consist of a group that can be site specifically removed and that is covalently attached to a therapeutic or diagnostic moiety Z via the novel elongated self-eliminating connector system $(W)_k$—$(X)_l$—A of the invention (FIG. 2). These self-eliminating connector systems possess increased lengths, which places the parent moiety Z at an increased distance from the specifier.

It is observed that spacers which self-eliminate through a 1,(4+2n)-elimination (n=0,1,2,3,4,5 . . . 10) (for example 1,6-elimination, 1,8-elimination, or 1,10-elimination) are from now called 'electronic cascade' spacers.

According to a preferred embodiment of the invention are the electronic cascade spacers W, X, and Y independently selected from compounds having the formula:

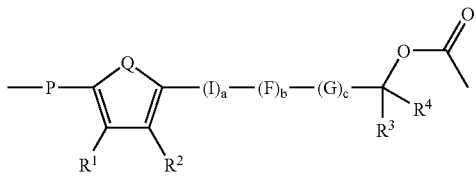

Q=—R⁵C=CR⁶—, S, O, NR⁵, —R⁵C=N—, or —N=CR⁵—

P=NR⁷, O, S wherein
a, b, and c are independently an integer of 0 (included) to 5 (included);
I, F and G are independently selected from compounds having the formula:

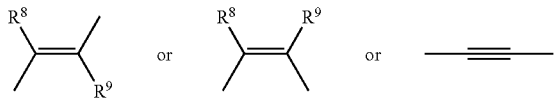

wherein $R^1$, $R^2$, $R^3$, $R^4$, $R^5$, $R^6$, $R^7$, $R^8$, and $R^9$ independently represent H, $C_{1-6}$ alkyl, $C_{3-20}$ heterocyclyl, $C_{5-20}$ aryl, $C_{1-6}$ alkoxy, hydroxy (OH), amino ($NH_2$), mono-substituted amino ($NR_xH$), di-substituted amino ($NR_x^1R_x^2$), nitro ($NO_2$), halogen, $CF_3$, CN, $CONH_2$, $SO_2Me$, CONHMe, cyclic $C_{1-5}$ alkylamino, imidazolyl, $C_{1-6}$ alkylpiperazinyl, morpholino, thiol (SH), thioether ($SR_x$), tetrazole, carboxy (COOH), carboxylate ($COOR_x$), sulphoxy ($S(=O)_2OH$), sulphonate ($S(=O)_2OR_x$), sulphonyl ($S(=O)_2R_x$), sulphixy ($S(=O)OH$), sulphinate ($S(=O)OR_x$), sulphinyl ($S(=O)R_x$), phosphonooxy ($OP(=O)(OH)_2$), and phosphate ($OP(=O)(OR_x)_2$), where $R_x$, $R_x^1$ and $R_x^2$ are independently selected from a $C_{1-6}$ alkyl group, a $C_{3-20}$ heterocyclyl group or a $C_{5-20}$ aryl group, two or more of the substituents $R^1$, $R^2$, $R^3$, $R^4$, $R^5$, $R^6$, $R^7$, $R^8$, or $R^9$ optionally being connected to one another to form one or more aliphatic or aromatic cyclic structures.

It is further observed that the principle of 1,6-elimination, as such developed in 1981, can be considered one of the most versatile self-elimination principles that can be used in prodrug design. According to this principle, spacer elimination proceeds via the mechanism depicted in FIG. 3. This particular elimination process has proven to be very successful when applied in the prodrug concept. Spacers that self-eliminate through an electronic cascade sequence as indicated in FIG. 3 generally show much faster half-lives of elimination than do spacers that eliminate via a cyclisation reaction. This is a significant difference between cyclization spacers and electronic cascade spacers.

In the following Examples, para-aminobenzyloxycarbonyl (PABC) and related electronic cascade spacer systems are used because they eliminate more rapidly upon unmasking of the amine, when compared to hydroxybenzyl-based electronic cascade spacers, which need electron-withdrawing substituents on the phenyl part of the spacer in order to let spacer elimination take place. Drug release will not take place when the spacer is an un-substituted hydroxybenzyl electronic cascade spacer.

Most efforts were, in the past, directed to the synthesis of electronic cascade spacers containing electron-withdrawing substituent(s). It was hypothesized that the withdrawal of electrons from the site where enzymatic activation occurs would enhance the rate of enzymatic activation. However, the activation rate of prodrugs containing an electron-withdrawing group on the spacer is usually not significantly different from that of un-substituted electronic cascade spacer containing prodrugs: A chloro-substituent on an aminobenzyl spacer for example only marginally enhances the rate of enzymatic prodrug activation by plasmin. In the case of aminobenzyl spacer-containing anthracycline prodrugs for activation by β-glucuronidase, chloro- or bromo-substituents showed only a marginal effect. It must further be considered that, although electron-withdrawing substituents on aminobenzyl spacers may increase enzymatic activation rates, spacer elimination rates will decrease as a consequence of substituents with such electronic properties. In the case of generation of hydroxylamino benzyl electronic cascade spacers it appeared that indeed electron-donating substituents on the benzyl ring accelerated fragmentation. This effect can probably be ascribed to stabilization of the developing positive charge on the benzylic carbon by these substituents. In some cases, when one or more of the spacer substituents are too electron-withdrawing, spacer elimination will not occur at all. An aminobenzyl spacer containing a nitro substituent at the meta position with respect to the specifier did not self-eliminate to release the free drug. It was also found that a hydroxylamino benzyl spacer with a nitro substituent at the meta position with respect to the specifier showed the slowest spacer elimination rate of such substituted hydroxylamino benzyl spacers. It appears that electron-withdrawing properties of spacer substituents have only marginal impact on enzymatic activation rates, whereas spacer elimination is greatly dependent on electronic properties of spacer substituents and occurs only in a relatively narrow characteristic electronic profile depending on the type of cascade spacer that is used.

In several previously reported prodrugs, containing one electronic cascade spacer, differences in enzymatic activation rates can still be observed when different parent drugs are connected with the same promoiety or when a parent drug is connected to the same promoiety via a different site of the drug. For example, β-glucuronidase cleaves the glucuronide from a β-glucuronide-cyclisation spacer promoiety much slower when paclitaxel is the parent drug in comparison with the prodrug containing doxorubicin as the parent drug. In another example, a dipeptide derivative of paclitaxel, linked via an aminobenzyl spacer was more readily cleaved by cathepsin B when paclitaxel was linked via its 7-position than via its 2'-position. In addition, half-lives of cathepsin B cleavage of electronic cascade spacer containing prodrugs of doxorubicin or mitomycin C were much shorter than the half-life of the corresponding prodrugs with paclitaxel as the parent drug. Finally, plasmin cleaves the tripeptide from an electronic cascade spacer containing doxorubicin prodrug much more readily than the tripeptide from the corresponding paclitaxel prodrug. Thus, in several prodrug systems the parent drug still exerts a significant effect on the rate of enzymatic activation, even though the mentioned prodrugs all contained one electronic cascade spacer.

The invention obviates the above-mentioned drawbacks by reduction of the influence of substituents of the spacer group on prodrug activation and/or spacer elimination and of the parent drug on the rate of enzymatic activation of the prodrug due to the presence of elongated spacer systems.

The invention is in a second aspect related to compounds of the above-mentioned formula wherein group U is a cyclisation spacer, from now called 'ω-amino aminocarbonyl' cyclisation spacer, and Z is a molecule having a hydroxyl group.

More preferably, the ω-amino aminocarbonyl cyclisation elimination spacer U of the invention is a compound having the formula:

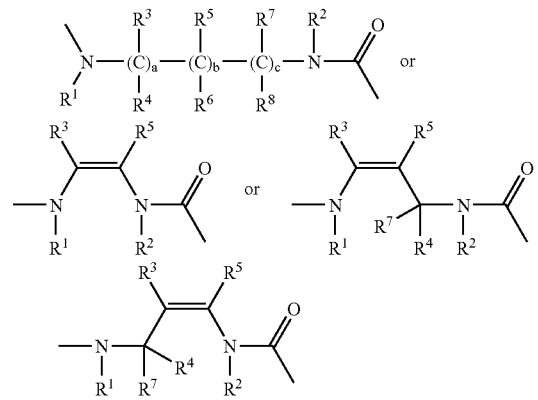

wherein:

a is an integer of 0 or 1; and b is an integer of 0 or 1; and c is an integer of 0 or 1; provided that a+b+c=2 or 3;

and wherein $R^1$ and/or $R^2$ independently represent H, $C_{1-6}$ alkyl, said alkyl being optionally substituted with one or more of the following groups: hydroxy (OH), ether ($OR_x$), amino ($NH_2$), mono-substituted amino ($NR_xH$), disubstituted amino ($NR_x^1R_x^2$), nitro ($NO_2$), halogen, $CF_3$, CN, $CONH_2$, $SO_2Me$, CONHMe, cyclic $C_{1-5}$ alkylamino, imidazolyl, $C_{1-6}$ alkylpiperazinyl, morpholino, thiol (SH), thioether ($SR_x$), tetrazole, carboxy (COOH), carboxylate ($COOR_x$), sulphoxy ($S(=O)_2OH$), sulphonate ($S(=O)_2OR_x$), sulphonyl ($S(=O)_2R_x$), sulphixy ($S(=O)OH$), sulphinate ($S(=O)OR_x$), sulphinyl ($S(=O)R_x$), phosphonooxy ($OP(=O)(OH)_2$), and phosphate ($OP(=O)(OR_x)_2$), where $R_x$, $R_x^1$ and $R_x^2$ are selected from a $C_{1-6}$ alkyl group, a $C_{3-20}$ heterocyclyl group or a $C_{5-20}$ aryl group; and $R^3$, $R^4$, $R^5$, $R^6$, $R^7$, and $R^8$ independently represent H, $C_{1-4}$ alkyl, $C_{3-20}$ heterocyclyl, $C_{5-20}$ aryl, $C_{1-6}$ alkoxy, hydroxy (OH), amino ($NH_2$), mono-substituted amino ($NR_xH$), disubstituted amino ($NR_x^1R_x^2$), nitro ($NO_2$), halogen, $CF_3$, CN, $CONH_2$, $SO_2Me$, CONHMe, cyclic $C_{1-5}$ alkylamino, imidazolyl, $C_{1-6}$ alkylpiperazinyl, morpholino, thiol (SH), thioether ($SR_x$), tetrazole, carboxy (COOH), carboxylate ($COOR_x$), sulphoxy ($S(=O)_2OH$), sulphonate ($S(=O)_2OR_x$), sulphonyl ($S(=O)_2R_x$), sulphixy ($S(=O)OH$), sulphinate ($S(=O)OR_x$), sulphinyl ($S(=O)R_x$), phosphonooxy ($OP(=O)(OH)_2$), and phosphate ($OP(=O)(OR_x)_2$), where $R_x$, $R_x^1$ and $R_x^2$ are selected from a $C_{1-6}$ alkyl group, a $C_{3-20}$ heterocyclyl group or a $C_{5-20}$ aryl group, two or more of the substituents $R^1$, $R^2$, $R^3$, $R^4$, $R^5$, $R^6$, $R^7$, or $R^8$ optionally being connected to one another to form one or more aliphatic or aromatic cyclic structures.

In a third aspect, the invention relates to compounds of the above-mentioned formula wherein spacer group A is an electronic cascade spacer having the formula:

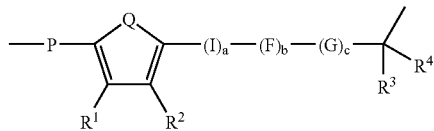

$Q=-R^5C=CR^6-$, S, O, $NR^5$, $-R^5C=N-$, or $-N=CR^5-$ $P=NR^7$, O, S wherein a, b, and c are independently an integer of 0 to 5;

I, F and G are independently selected from compounds having the formula:

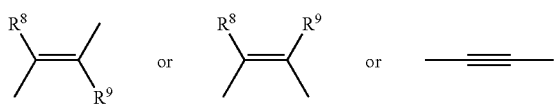

wherein $R^1$, $R^2$, $R^3$, $R^4$, $R^5$, $R^6$, $R^7$, $R^8$, and $R^9$ independently represent H, $C_{1-6}$ alkyl, $C_{3-20}$ heterocyclyl, $C_{5-20}$ aryl, $C_{1-6}$ alkoxy, hydroxy (OH), amino ($NH_2$), mono-substituted amino ($NR_xH$), disubstituted amino ($NR_x^1R_x^2$), nitro ($NO_2$), halogen, $CF_3$, CN, $CONH_2$, $SO_2Me$, CONHMe, cyclic $C_{1-5}$ alkylamino, imidazolyl, $C_{1-6}$ alkylpiperazinyl, morpholino, thiol (SH), thioether ($SR_x$), tetrazole, carboxy (COOH), carboxylate ($COOR_x$), sulphoxy ($S(=O)_2OH$), sulphonate ($S(=O)_2OR_x$), sulphonyl ($S(=O)_2R_x$), sulphixy ($S(=O)OH$), sulphinate ($S(=O)OR_x$), sulphinyl ($S(=O)R_x$), phosphonooxy ($OP(=O)(OH)_2$), and phosphate ($OP(=O)(OR_x)_2$), where $R_x$, $R_x^1$ and $R_x^2$ are independently selected from a $C_{1-4}$ alkyl group, a $C_{3-20}$ heterocyclyl group or a $C_{5-20}$ aryl group, two or more of the substituents $R^1$, $R^2$, $R^3$, $R^4$, $R^5$, $R^6$, $R^7$, $R^8$, or $R^9$ optionally being connected to one another to form one or more aliphatic or aromatic cyclic structures.

In one embodiment the elongated spacer system $(W)_k-(X)_l-A$ is a molecule that self-eliminates via a 1,(4+2n)-elimination (n=2,3,4,5 . . . 10), for example a 1,8-elimination (FIG. 4). The length of this novel spacer system can be extended, for example to a 1,10-elimination spacer system, in which two or more double or triple bonds instead of one are conjugated with the aromatic part of the spacer (FIG. 5).

In another embodiment, the spacer system of the invention consists of two or more electronic cascade spacers that are connected to one another. Release of the leaving group (the drug) occurs after two or more subsequent spacer eliminations.

In again another embodiment, prodrugs of hydroxyl functionality containing drugs (such as for example paclitaxel) are claimed that contain both one or more electronic cascade spacers and a cyclisation spacer.

In a preferred embodiment the spacer that is directly connected to the paclitaxel molecule is an ω-amino aminocarbonyl cyclisation spacer that is linked to the 2'-position of paclitaxel via a carbamate linkage. A convenient synthetic route to this class of paclitaxel derivatives is disclosed.

In another embodiment the elongated electronic cascade spacer system is coupled to the phenolic hydroxyl group of the drug moiety via an ether linkage. When the leaving group (i.e., the drug) is an phenolic hydroxyl group, a para-aminobenzylether has been reported to self-eliminate.

The elongated spacer systems provide for improved enzymatic activation characteristics.

The self-eliminating connector systems in this invention possess increased lengths with respect to an electronic cascade spacer system available at present. It is observed that one end of the linker system must be able to react with the specifier, for example the tripeptide that is a substrate for plasmin. Typically, this end of the spacer system is an amino group or a hydroxyl group, but it can also be another functionality. The functionality at the other end of the linker system must be able to react with the drug. Typically, this end of the spacer system is a hydroxyl group, but it can also be another functionality. In one embodiment this functionality reacts with an amino group of the drug to form a carbamate linkage between linker and drug. In another embodiment, this functionality reacts with a hydroxyl group of the drug to form a carbonate linkage between linker and drug. In again another embodiment, this functionality reacts with a sulfhydryl group of the drug to form a thiocarbonate linkage between linker and drug. In again another embodiment this functionality reacts with a carboxylic acid group of the drug to form an ester linkage between linker and drug.

Typically, the spacer system is p-aminobenzyloxycarbonyl-p-aminobenzyloxycarbonyl, p-aminobenzyloxycarbonyl-p-aminobenzyloxycarbonyl-p-aminobenzyloxycarbonyl, p-aminocinnamyloxycarbonyl, p-aminocinnamyloxycarbonyl-p-aminobenzyloxycarbonyl, p-aminobenzyloxycarbonyl-p-aminocinnamyloxycarbonyl, p-aminocinnamyloxycarbonyl-p-amino-cinnamyloxycarbonyl, p-aminophenylpentadienyloxycarbonyl, p-aminophenylpenta-dienyloxycarbonyl-p-aminocinnamyloxycarbonyl, p-aminophenylpentadienyloxycarbonyl-p-aminobenzyloxycarbonyl, p-aminophenylpentadienyloxycarbonyl-p-aminophenylpentadienyloxycarbonyl, p-aminobenzyloxycarbonyl(methylamino)ethyl(methylamino)carbonyl, p-aminocinnamyloxycarbonyl(methylamino)ethyl(methylamino)carbonyl, p-aminobenzyloxycarbonyl-p-aminobenzyloxycarbonyl(methylamino)ethyl(methylamino)carbonyl, p-aminocinnamyloxycarbonyl-p-aminobenzyloxycarbonyl(methylamino)ethyl(methylamino)carbonyl, p-aminobenzyloxycarbonyl-p-aminocinnamyloxycarbonyl(methylamino)ethyl(methylamino)carbonyl, p-aminocinnamyloxycarbonyl-p-aminocinnamyloxycarbonyl(methylamino)ethyl(methylamino)carbonyl, p-aminobenzyloxycarbonyl-p-aminobenzyl, p-aminobenzyloxycarbonyl-p-aminobenzyloxycarbonyl-p-aminobenzyl, p-aminocinnamyl, p-aminocinnamyloxycarbonyl-p-aminobenzyl, p-aminobenzyloxycarbonyl-p-aminocinnamyl, p-aminocinnamyloxycarbonyl-p-aminocinnamyl, p-aminophenylpentadienyl, p-aminophenylpentadienyloxycarbonyl-p-aminocinnamyl, p-aminophenylpentadienyloxycarbonyl-p-aminobenzyl, or p-aminophenylpentadienyloxycarbonyl-p-aminophenylpentadienyl.

In the compounds of formula V—(W)$_k$—(X)$_l$—A—Z, the specifier V typically contains a substrate molecule that is specifically cleaved by an enzyme present in the vicinity of the target cells, for example tumor cells. More preferably, the specifier V contains a substrate that is specifically cleaved by an enzyme present at elevated levels in the vicinity of the target cells as compared to other parts of the body, and most preferably the enzyme is present only in the vicinity of the target cells.

The specifier V may also contain a moiety that targets the compounds of formula V—(W)$_k$—(X)$_l$—A—Z to the target site by selective complexing with a receptor or other receptive moiety associated with a given target cell population or by causing accumulation of compounds V—(W)$_k$—(X)$_l$—A—Z in the vicinity of the target cells by another mechanism. This targeting moiety may, for example, be bombesin, transferrin, gastrin, gastrin-releasing peptide, a molecule that specifically binds $\alpha_v\beta_3$ and/or $\alpha_v\beta_5$-integrin receptors, such as RGD-containing peptides, platelet-derived growth factor, IL-2, IL-6, a tumor growth factor, vaccinia growth factor, insulin and insulin-like growth factors I en II, an antigen-recognizing immunoglobulin or an antigen-recognizing fragment thereof, or a carbohydrate. Preferably, that antigen recognized by the immunoglobulin (or fragment thereof) is specific for the target cells, e.g. a tumor-specific antigen. The specifier V may also contain a polymer, which causes accumulation of compounds V—(W)$_k$—(X)$_l$—A—Z in the vicinity of the target cells, e.g. tumor cells, because of the Enhanced Permeability and Retention (EPR) effect.

In one embodiment, the specifier is a di-, tri-, or oligopeptide which consists of an amino acid sequence specifically recognized by a protease, for example plasmin, a cathepsin, cathepsin B, prostate-specific antigen (PSA), urokinase-type plasminogen activator (u-PA), or a member of the family of matrix metalloproteinases, present in the vicinity of the target cells, for example tumor cells, or, in another embodiment, a β-glucuronide that is specifically recognized by β-glucuronidase present in the vicinity of tumor cells. In again another embodiment the specifier is a nitro-aromatic moiety that can be reduced under hypoxic conditions or by nitroreductases. After removal of the nitro-aromatic specifier, elimination of the spacer systems described in this invention leads to drug release. It can be understood that any specifier that is specifically cleaved following recognition by a disease-specific and/or organ-specific enzyme and/or receptor can be incorporated into prodrugs that contain the linker systems claimed in this invention.

The moiety Z is a therapeutic or diagnostic moiety. Z can for instance be an anticancer drug, an antibiotic, an anti-inflammatory agent, or an anti-viral agent. Typically, the moiety Z is an anticancer drug. Preferably the anticancer drug is the amino containing daunorubicin, doxorubicin, N-(5,5-diacetoxypentyl)doxorubicin, an anthracycline, mitomycin C, mitomycin A, 9-amino campiothecin, aminopterin, actinomycin, bleomycin, N$^8$-acetyl spermidine, 1-(2-chloroethyl)-1,2-dimethanesulfonyl hydrazine, tallysomycin, or derivatives thereof. The anticancer drug can also be the hydroxyl containing etoposide, camptothecin, irinotecan, topotecan, 9-amino camptothecin, paclitaxel, docetaxel, esperamycin, 1,8-dihydroxybicyclo[7.3.1]trideca-4-ene-2,6-diyne-13-one, anguidine, doxorubicin, morpholinedoxorubicin, N-(5,5-diacetoxypentyl) doxorubicin, vincristine, vinblastine, or derivatives thereof. The anticancer drug can also be the sulfhydryl containing esperamicin, 6-mercaptopurine, or derivatives thereof. The drug can also be the carboxyl containing methotrexate, camptothecin (ring-opened form of the lactone), butyric acid, retinoic acid, or derivatives thereof.

To show the principle of elimination of elongated spacer systems, tumor-specific prodrugs that are selectively hydrolyzed by the tumor-associated protease plasmin were synthesized. The synthesized prodrugs consist of a tripeptide specifier that is coupled to the drug via an elongated self-eliminating spacer. The tripeptide specifier contains an amino acid sequence that is specifically recognized by the tumor-associated enzyme plasmin. The synthesis of these derivatives is disclosed.

There is an increasing body of literature that links production of certain proteases to tumor malignancy. Mostly, proteolytic activity is required for tumor cells when they become invasive and form metastases. A primary tumor is encapsulated in an extracellular matrix, which consists of proteins. In order to form metastases, the primary tumor must break through this matrix. For this reason, enhanced expression of proteolytic enzymes by invading and metastasizing tumors is generated. Recent studies indicate that proteases are involved also in earlier stages of tumor progression, at both primary and metastatic sites. A number of proteases, like cathepsins, the u-PA system, and the matrix metalloproteinases, take part in the proteolytic cascade.

The u-PA system has received broad attention in the literature, especially in the last decade. Several invasive and metastasizing human tumors express a significantly higher plasminogen activator activity in comparison with normal tissue. An increased activity and expression of u-PA is found in several tumor cell lines and human solid tumors, like lung tumors, prostate cancers, breast cancers, ovarian carcinomas and several other cancer types. u-PA is an important enzyme in proteolytic reactions that are required for the spreading and invasiveness of cells, both in cancer and in tissue remodeling processes. u-PA interacts with a specific high-affinity receptor on the cell surface. Receptor-bound u-PA is catalytically active on the surface of the cell without requiring internalization. It interacts with plasminogen to produce plasmin that is still bound to the cell surface. The high u-PA level via this pathway leads to elevated levels of plasmin. There exists substantial evidence that the protease plasmin itself plays a key role in tumor invasion and metastasis. Plasmin itself catalyses the breakdown of extracellular matrix proteins. Thus, the plasminogen activator system is intimately associated with tumor metastasis. Even the process of angiogenesis, nowadays considered as an important target mechanism for the development of new therapeutic strategies, is a urokinase dependent process. The plasminogen activation system may be involved in cell adhesion processes by regulating integrin functions. Vascular endothelial growth factor (VEGF), an angiogenic molecule, is suggested to interact with u-PA in tumor progression. u-PA catalyzed plasmin generation proved to be an important determinant of tumor metastasis in many experiments with animal model systems.

For the reasons outlined above, plasmin can be a very promising enzyme for the targeting of peptide prodrugs of anticancer agents. Active plasmin is localized in tumor tissue because it is formed from its inactive pro-enzyme form plasminogen by u-PA, produced by cancer and/or stroma cells. In the blood circulation active plasmin is rapidly inhibited by inhibitors that block the active site, such as $\alpha_2$-antiplasmin. Cell-bound plasmin as present in tumor tissue is not inhibited. In addition, plasmin is suitable as a target enzyme for prodrugs, because it is generated at the end of the proteolytic cascade. One molecule of u-PA can generate more than one molecule of plasmin.

The amino acid sequence of the tripeptide to be a plasmin substrate must be chosen such that it is a specific substrate for the serine protease plasmin. The C-terminal amino acid that is coupled to the spacerdrug moiety is arginine or lysine, preferably an L-lysine residue. Plasmin is known to cleave most easily after a lysine residue. The amino acid at the N-terminus possesses the D-configuration in order to prevent in vivo cleavage by ubiquitous amino peptidases. Protecting the N-terminal amino function by a Boc or Fmoc group can also prevent unwanted peptidase cleavage. The amino acid in the middle is preferably a hydrophobic L-amino acid and is selected from the group consisting of alanine, valine, leucine, isoleucine, methionine, phenylalanine, cyclohexylglycine, tryptophan and proline. Preferred tripeptide sequences are D-alanylphenylalanyllysine, D-valylleucyllysine, D-alanylleucyllysine, D-valylphenylalanyllysine, D-valyltryptophanyllysine, and D-alanyltryptophanyllysine.

By converting the two amino groups of the tripeptide into the corresponding ammonium salts, the water solubility of the prodrug should be improved.

In the present invention the synthesis and application of new elongated spacer systems is described. In one embodiment, this spacer self-eliminates through a 1,(4+2n)-elimination process (FIGS. 4, 5). These 1,(4+2n)-elimination spacers are elongated with respect to the conventional 1,6-elimination spacer. Proof of principle of 1,8-elimination was delivered upon chemical reduction of the nitrocinnamyl carbonate derivative of paclitaxel using zinc and acetic acid (FIGS. 6, 7). Released paclitaxel was isolated in good yield. Firstly, the doubly protected tripeptide was synthesized (FIG. 8). The 1,8-elimination spacer itself was synthesized from 4-nitrocinnamyl alcohol as depicted in FIG. 9. 4—Aminocinnamyl alcohol was incorporated between doxorubicin and a tripeptide for plasmin activation (FIG. 10). What is also disclosed in this invention are prodrugs that contain two or more electronic cascade spacers connected to one another, incorporated between specifier and drug (FIG. 11). Prodrugs containing linker systems of this kind have not been reported before. This embodiment of the present invention was exemplified by synthesizing two prodrugs containing a tripeptide specifier coupled to doxorubicin or paclitaxel via two 1,6-elimination spacers. This protected tripeptide was subsequently coupled with 4-aminobenzyl alcohol, and the resulting benzylic alcohol was activated with 4-nitrophenyl chloroformate to yield the corresponding 4-nitrophenyl carbonate (FIG. 12). In a very efficient reaction a second molecule of 4-aminobenzyl alcohol was coupled to the activated carbonate in which hydroxy benzotriazole HOBt) was employed as a catalyst to yield the corresponding tripeptide-double spacer conjugate (FIG. 13). When this reaction was performed using diphenyl phosphinic acid as a catalyst, the product was isolated in only 16 percent yield (FIG. 14). The peptide-double spacer conjugate was incorporated into a doxorubicin prodrug (FIG. 15) and a paclitaxel prodrug (FIG. 16), by subsequent chloroformate activation, coupling with the drug and final deprotection. A double spacer-containing doxorubicin prodrug with a tryptophan residue instead of phenylalanine was also synthesized (FIGS. 17, 18). According to a further embodiment a third 4-aminobenzyl alcohol spacer was reacted with the 4-nitrophenyl carbonate activated tripeptide-double spacer conjugate to yield the corresponding tripeptide-triple spacer conjugate (FIG. 19). This compound was subsequently converted to the corresponding triple electronic cascade spacer containing doxorubicin prodrug employing a similar route as depicted in FIGS. 15 and 16.

What is also claimed are prodrugs in which the promoiety is coupled to a hydroxyl group of parent moiety Z via a carbamate linkage. These carbamate coupled prodrugs contain an elongated linker system that contains both one or more electronic cascade spacers and an ω-amino aminocarbonyl cyclisation spacer (FIG. 20). Paclitaxel-2'-carbamate prodrugs of this type were synthesized via a novel convergent route; which leads to high yields, as claimed in claims 35 and 36. Paclitaxel will be released after one or more 1,(4+2n)-eliminations (n=0,1,2,3,4,5, . . . 10) and a subsequent intramolecular cyclisation. In the present invention the cyclisation spacer is connected to the 2'-OH group of paclitaxel through a carbamate linkage (FIG. 20). Firstly, paclitaxel was selectively activated at the 2'-position (FIG. 21) Secondly, a mono-protected cyclisation spacer was coupled to the 2'-activated paclitaxel analog and the protective group was removed under acidic conditions to yield the first fragment (FIG. 22). The second fragment was synthesized by connecting the 1,6-elimination spacer to the tripeptide specifier and subsequent 4-nitrophenyl chloroformate activation of the benzylic alcohol function (FIG. 12). Then, both fragments were coupled to one another (FIG. 23) and the coupled product was deprotected (FIG. 24). Coupling of two separate fragments according to this strategy in which in the final stage the chemical link between the two spacers is established, did provide the most efficient route to the paclitaxel prodrug. This is a novel route to obtain prodrugs of this type, in which a specifier is connected to a hydroxyl containing drug via an electronic cascade spacer system (connected to the specifier) and a cyclisation spacer (connected to the drug). The preparation of two other prodrugs of paclitaxel that contain both an electronic cascade spacer system and a cyclisation spacer is depicted in FIGS. 25–27. In FIG. 28 previously reported plasmin-activatible prodrugs containing one electronic cascade spacer are depicted.

In a further aspect the invention relates to processes for the synthesis of the prodrugs as defined above. The invention e.g. relates to a process for the synthesis of prodrugs as defined above having at least one electronic cascade spacer group, and an ω-amino aminocarbonyl cyclisation elimination spacer group, connected to each other, incorporated between a specifier group and a drug molecule such that said drug molecule is connected to said cyclisation elimination spacer group, via the hydroxyl functionality of the drug molecule, by coupling a first electronic cascade spacer group, connected to said specifier group, if desired via at least one, second electronic cascade spacer group, being the same or different as said first electronic cascade spacer group, to said cyclisation elimination spacer group. In a preferred process said drug molecule is paclitaxel, and in a first step a cyclisation elimination spacer group is coupled to paclitaxel via its 2'-hydroxyl group through a carbamate linkage via addition of the free spacer-amine to a 4-nitrophenyl carbonate activated drug, followed by deprotection to obtain a first fragment consisting of a cyclisation spacer connected with paclitaxel, and in a second step one or more 1,(4+2n) electronic cascade spacers, being the same or different, wherein n is an integer of 0 to 10, are coupled to a specifier group, subsequently activated to the corresponding 4-nitrophenyl carbonate, whereafter in a third step the fragments obtained in the first and second step are coupled to one another under basic reaction conditions.

The invention further relates to a process for the synthesis of prodrugs as defined above, in which electronic cascade spacers are connected to one another by coupling of the terminal alcohol group of an electronic cascade spacer to the aniline amino group of another electronic cascade spacer through a carbamate linkage by conversion of the alcohol group of the first-mentioned electronic cascade spacer to the corresponding 4-nitrophenyl carbonate and reacting this molecule with the other electronic cascade spacer in the presence of a catalytic amount of 1-hydroxybenzotriazole either in the presence or absence of base.

In yet another aspect the invention relates to the use of any of the compounds defined above for the manufacture of a pharmaceutical preparation for the treatment of a mammal being in need thereof. The invention also relates to methods of treating a mammal being in need thereof, whereby the method comprises the administration of a pharmaceutical composition to the mammal in a therapeutically effective dose.

In a further aspect the invention relates to a process for preparing a pharmaceutical composition containing a compound as defined above, to provide a solid or a liquid formulation for administration orally, topically or by injection. Such a process at least comprises the step of mixing the compound with a pharmaceutically acceptable carrier.

The invention also relates to pharmaceutical compositions comprising the compounds of the invention as defined above. The compounds of the invention may be administered in purified form together with a pharmaceutical carrier as a pharmaceutical composition. The preferred form depends on the intended mode of administration and therapeutic or diagnostic application. The pharmaceutical carrier can be any compatible, nontoxic substance suitable to deliver the compounds of the invention to the patient. Pharmaceutically acceptable carriers are well known in the art and include, for example, aqueous solutions such as (sterile) water or physiologically buffered saline or other solvents or vehicles such as glycols, glycerol, oils such as olive oil or injectable organic esters, alcohol, fats, waxes, and inert solids may be used as the carrier. A pharmaceutically acceptable carrier may further contain physiologically acceptable compounds that act, e.g. to stabilise or to increase the absorption of the compounds of the invention. Such physiologically acceptable compounds include, for example, carbohydrates, such as glucose, sucrose or dextrans, antioxidants, such as ascorbic acid or glutathione, chelating agents, low molecular weight proteins or other stabilisers or excipients. One skilled in the art would know that the choice of a pharmaceutically acceptable carrier, including a physiologically acceptable compound, depends, for example, on the route of administration of the composition. Pharmaceutically acceptable adjuvants, buffering agents, dispersing agents, and the like, may also be incorporated into the pharmaceutical compositions.

For oral administration, the active ingredient can be administered in solid dosage forms, such as capsules, tablets, and powders, or in liquid dosage forms, such as elixirs, syrups, and suspensions. Active component(s) can be encapsulated in gelatin capsules together with inactive ingredients and powdered carriers, such as glucose, lactose, sucrose, mannitol, starch, cellulose or cellulose derivatives, magnesium stearate, stearic acid, sodium saccharin, talcum, magnesium carbonate and the like. Examples of additional inactive ingredients that may be added to provide desirable color, taste, stability, buffering capacity, dispersion or other known desirable features are red iron oxide, silica gel, sodium lauryl sulfate, titanium dioxide, edible white ink and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric-coated for selective disintegration in the gastrointestinal tract. Liquid dosage forms for oral administration can contain colouring and flavouring to increase patient acceptance.

The compounds of the invention are however preferably administered parentally. Preparations of the compounds of the invention for parental administration must be sterile. Sterilisation is readily accomplished by filtration through sterile filtration membranes, optionally prior to or following lyophilisation and reconstitution. The parental route for administration of compounds of the invention is in accord with known methods, e.g. injection or infusion by intravenous, intraperitoneal, intramuscular, intraarterial or intralesional routes. The compounds of the invention may be administered continuously by infusion or by bolus injection. A typical composition for intravenous infusion could be made up to contain 100 to 500 ml of sterile 0.9% NaCl or 5% glucose optionally supplemented with a 20% albumin solution and 1 mg to 10 g of the compound of the invention, depending on the particular type of compound of the invention and its required dosing regime. Methods for preparing parenterally administrable compositions are well known in the art and described in more detail in various sources, including, for example, Remington's Pharmaceutical Science (15th ed., Mack Publishing, Easton, Pa., 1980) (incorporated by reference in its entirety for all purposes).

The invention also relates to compounds as defined above, wherein the specifier V is removed by an enzyme that is transported to the vicinity of target cells or target tissue via antibody-directed enzyme prodrug therapy (ADEPT), polymer-directed enzyme prodrug therapy (PDEPT), virus-directed enzyme prodrug therapy (VDEPT) or gene-directed enzyme prodrug therapy (GDEPT) (see e.g. U.S. Pat. No. 4,975,278, Melton et al., 1996, J. Natl. Can. Inst. 88(3/4): 153–165).

The invention is further exemplified by the following Examples. These examples are for illustrative purposes and are not intended to limit the scope of the invention

BRIEF DESCRIPTION OF DRAWINGS

FIG. 1 shows schematically the conversion of a spacer containing tripartate prodrug into the parent drug.

FIG. 2 shows schematically the structure of an elongated spacer containing prodrug.

FIG. 3 shows the principle of 1,6-elimination.

FIG. 11 shows schematically the structure of a prodrug containing two or more electronic cascade spacers.

FIG. 12 shows the synthesis of para-nitrophenyl (PNP) carbonate-activated tripeptide-spacer conjugate.

FIG. 13 shows the catalytic coupling of a second electronic cascade spacer molecule (para-aminobenzyl alcohol (PABA)) to the 4-nitrophenyl carbonate-activated tripeptide-spacer conjugate in the presence of hydroxy benzotriazole (HOBt).

EXAMPLES

Example 1

Figure 4:
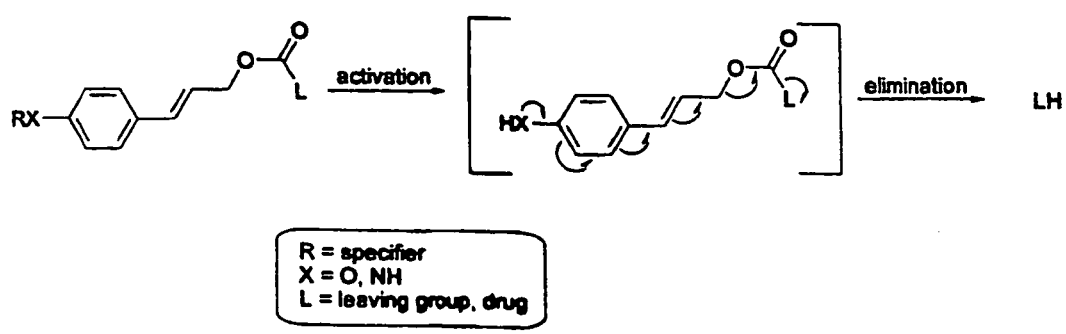
FIG. 4 shows the principle of 1,8-elimination.
Figure 5:
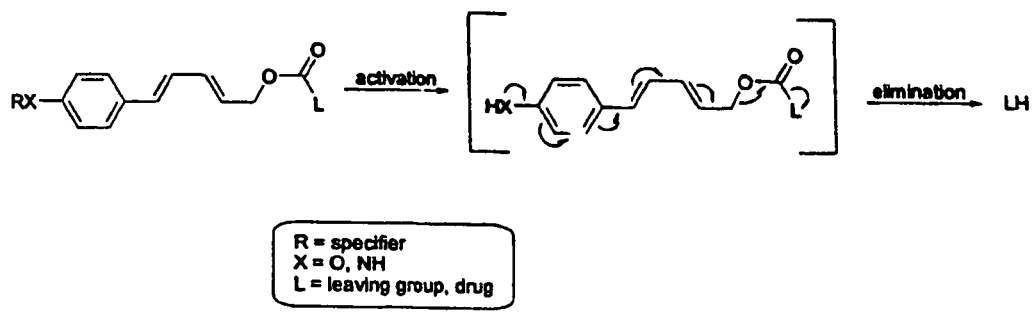
FIG. 5 shows the principle of 1,10-elimination.
Figure 6:
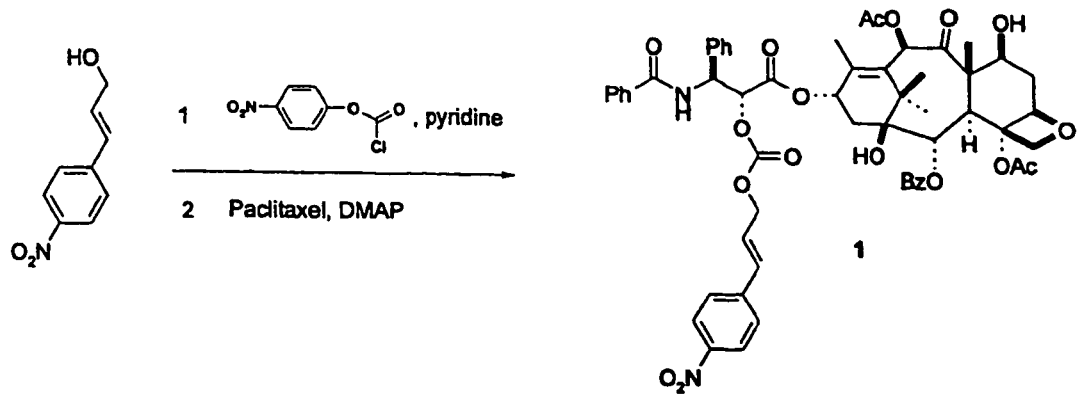
FIG. 6 shows the synthesis of the model paclitaxel-containing compound to prove the principle of 1,8-elimination.
Figure 7:
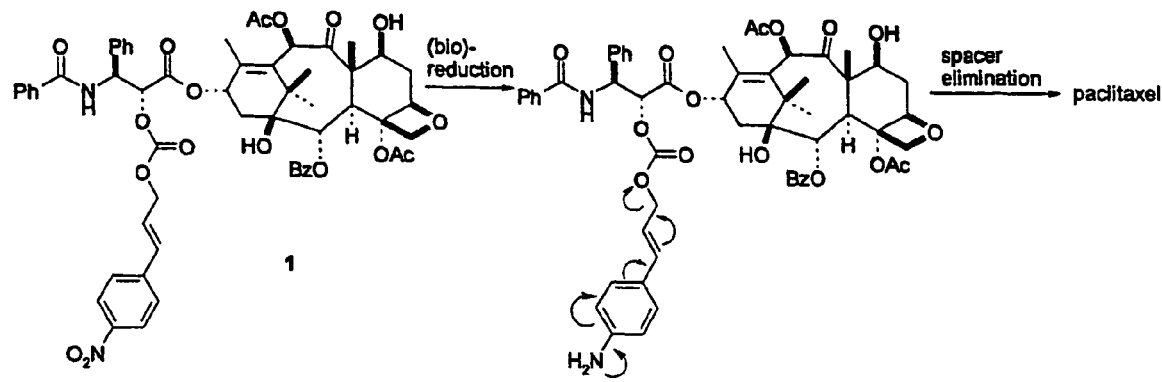
FIG. 7 shows the mechanism for the release of paclitaxel after reduction and 1,8-elimination.
Figure 8:
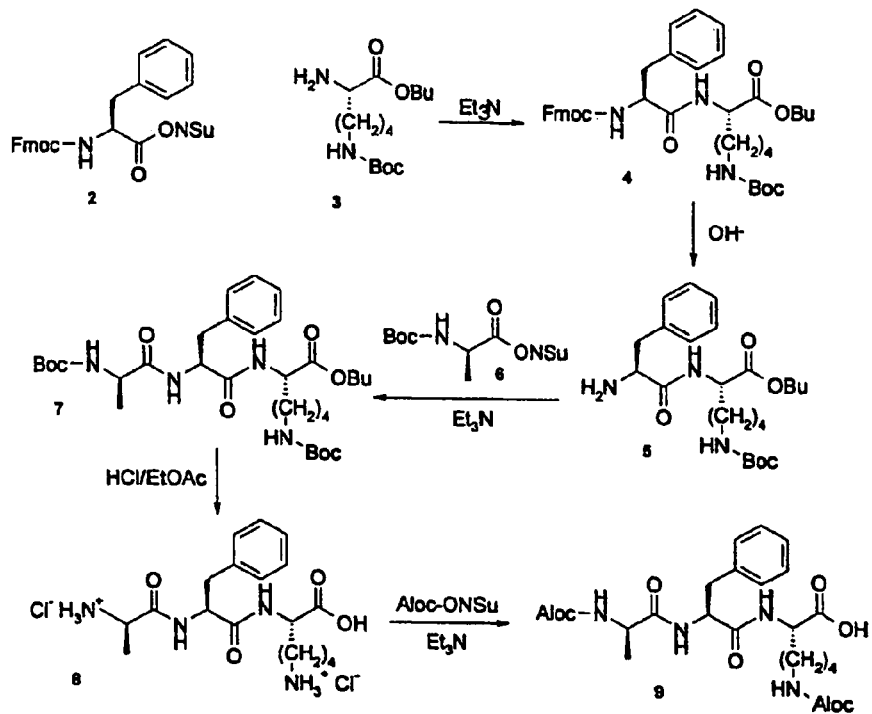
FIG. 8 shows the synthesis of the doubly Aloc-protected D-Ala-Phe-Lys tripeptide.
Figure 9:
FIG. 9 shows the synthesis of the 1,8-elimination spacer para-aminocinnamyl alcohol (PACA).
Figure 10:
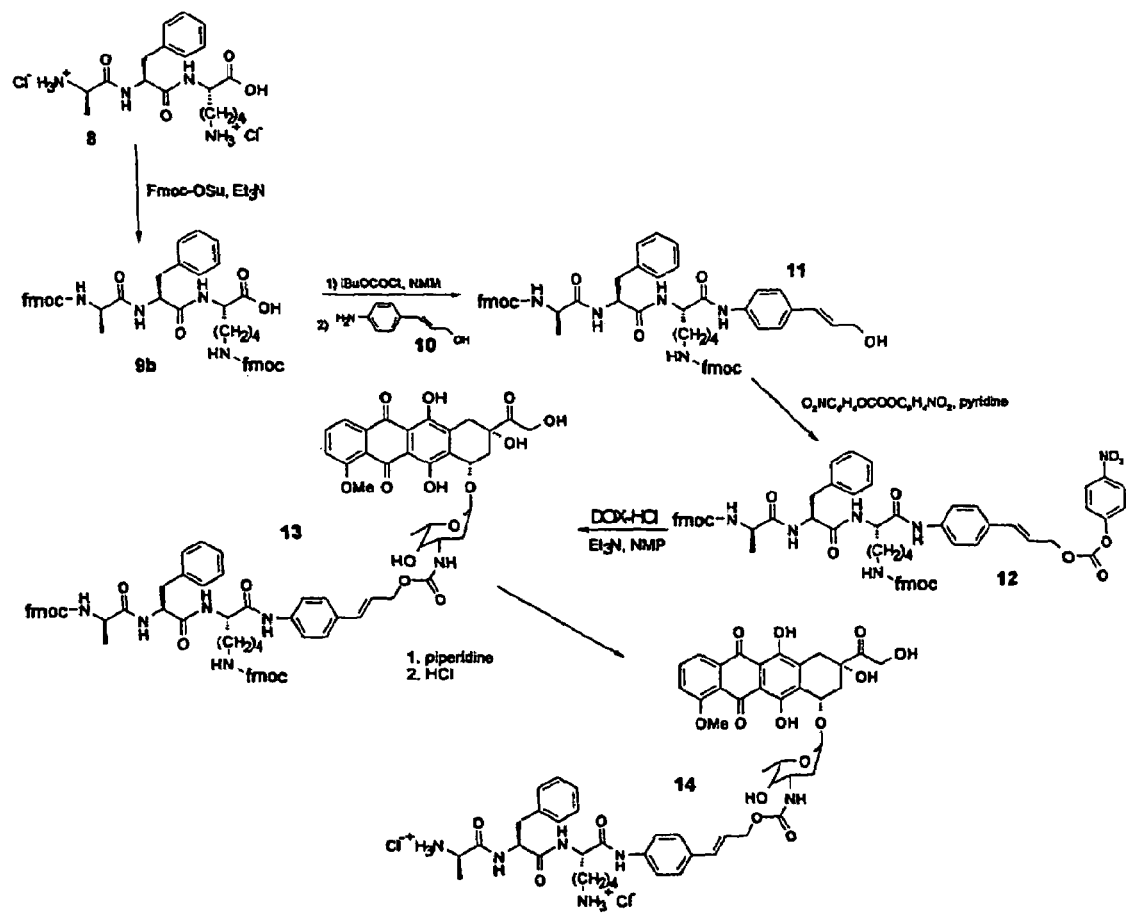
FIG. 10 shows the synthesis of a 1,8-elimination spacer containing prodrug.
Figure 14:
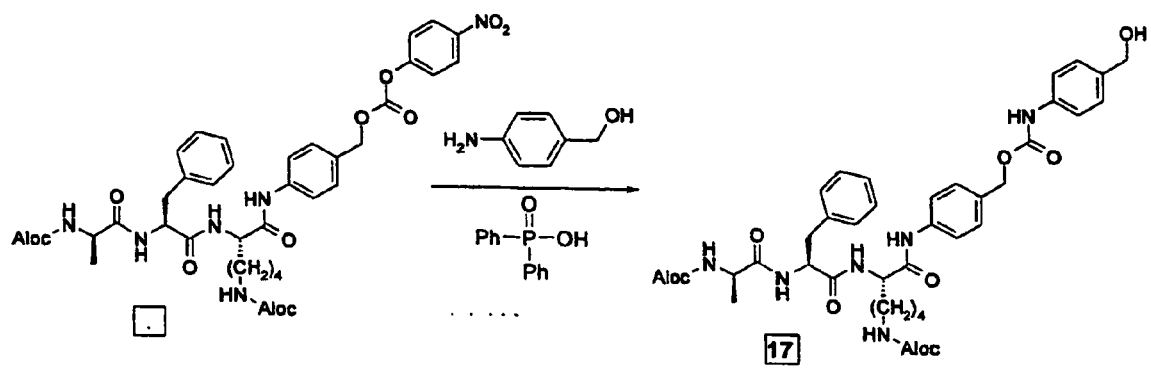
FIG. 14 shows a reaction to chemically link two electronic cascade spacer molecules by coupling a second electronic cascade 1,6-elimination spacer molecule to a 4-nitrophenyl carbonate activated tripeptide-1,6-elimination spacer conjugate in the presence of catalytic amounts of diphenyl phosphinic acid.
Figure 15:
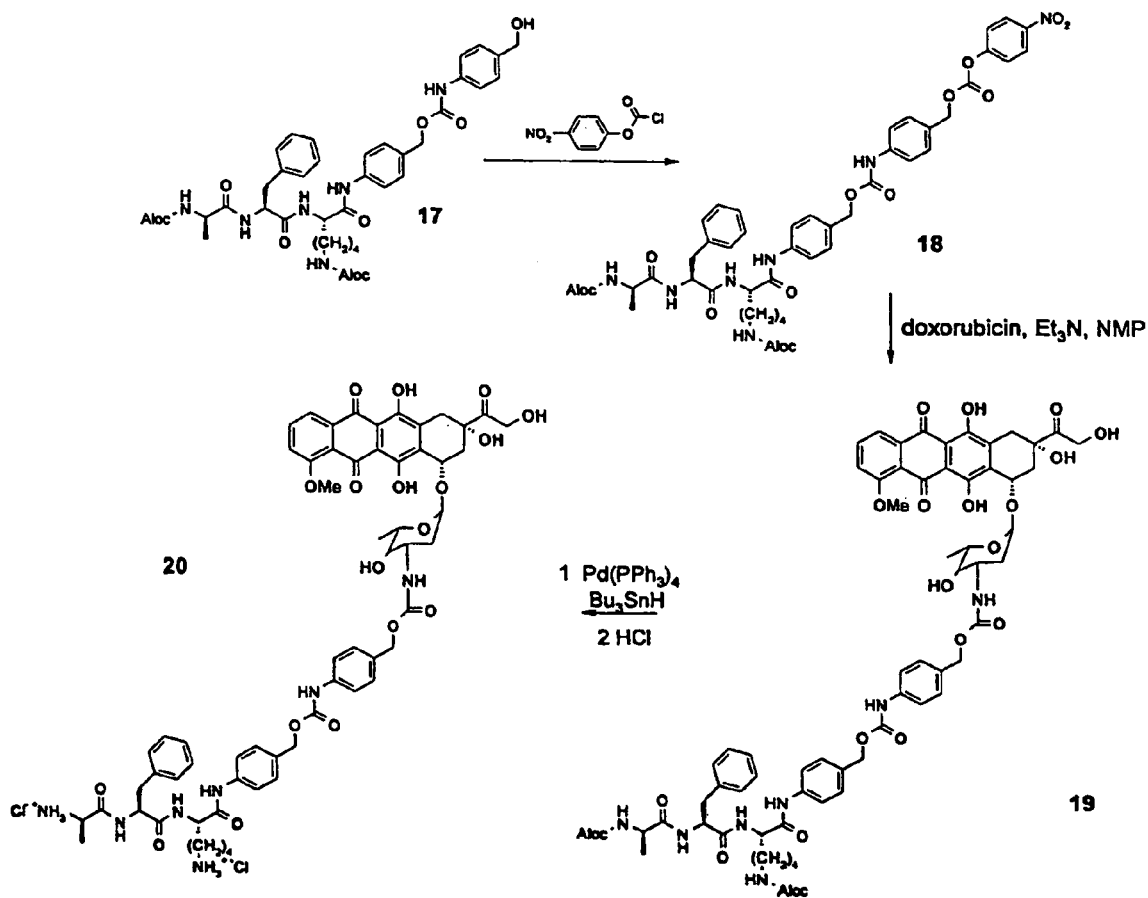
FIG. 15 shows the synthesis of a doxorubicin containing double 1,6-elimination spacer containing prodrug.
Figure 16:
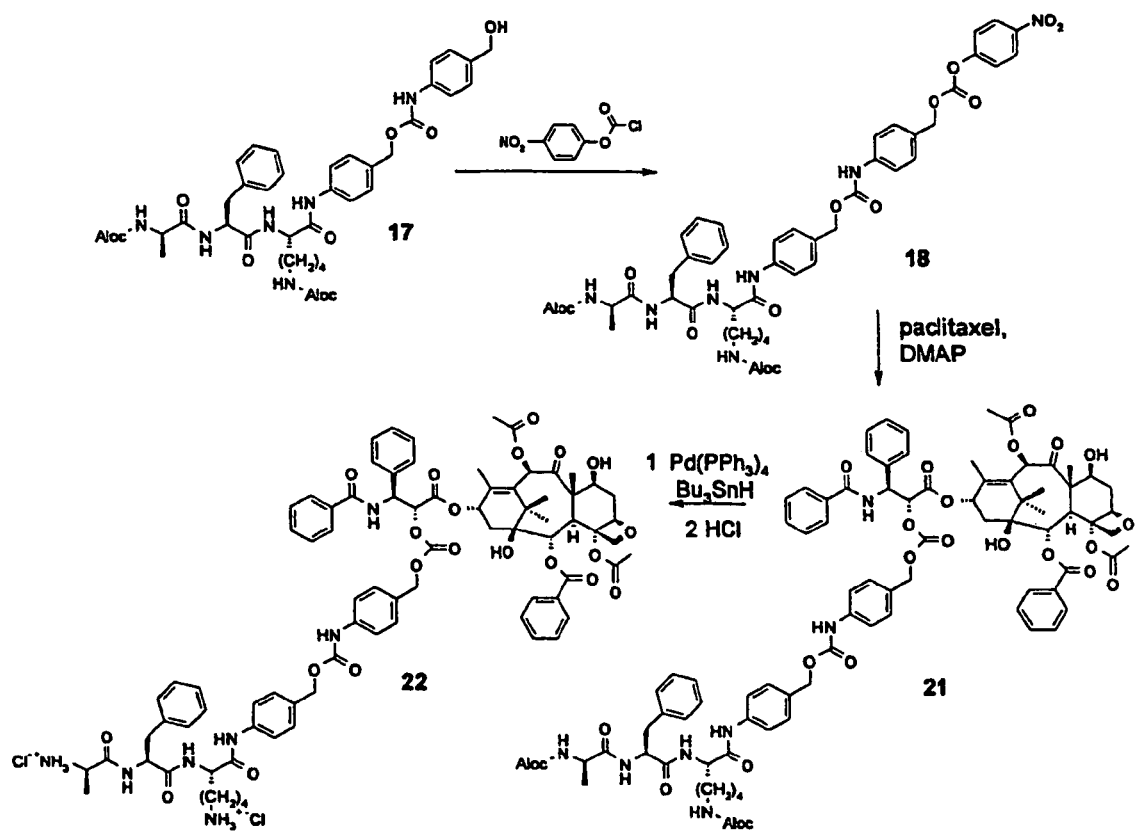
FIG. 16 shows the synthesis of a paclitaxel containing double 1,6-elimination spacer containing prodrug.
Figure 17:
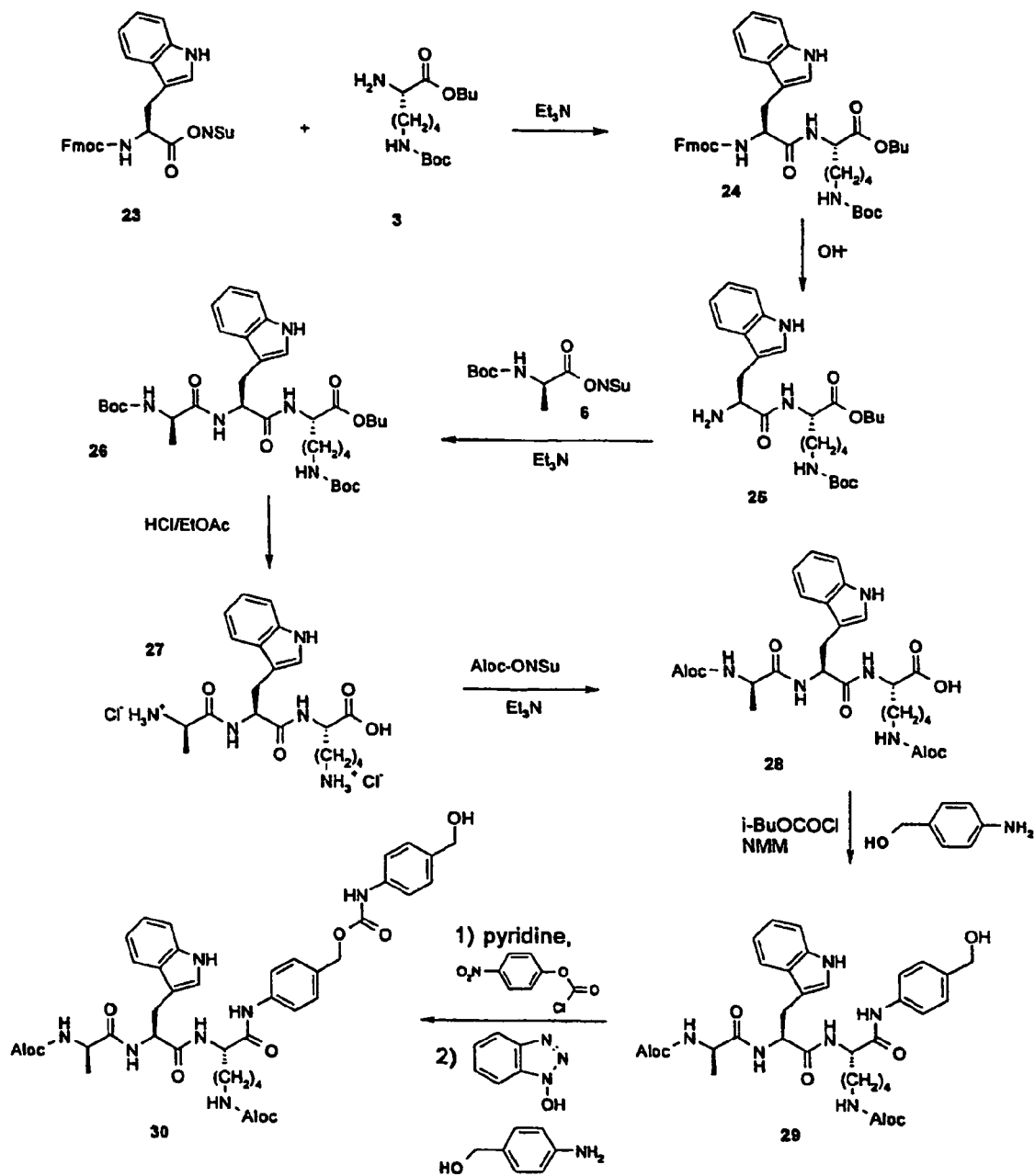
FIG. 17 shows the synthesis of a tryptophan-containing tripeptide double spacer conjugate.
Figure 18:
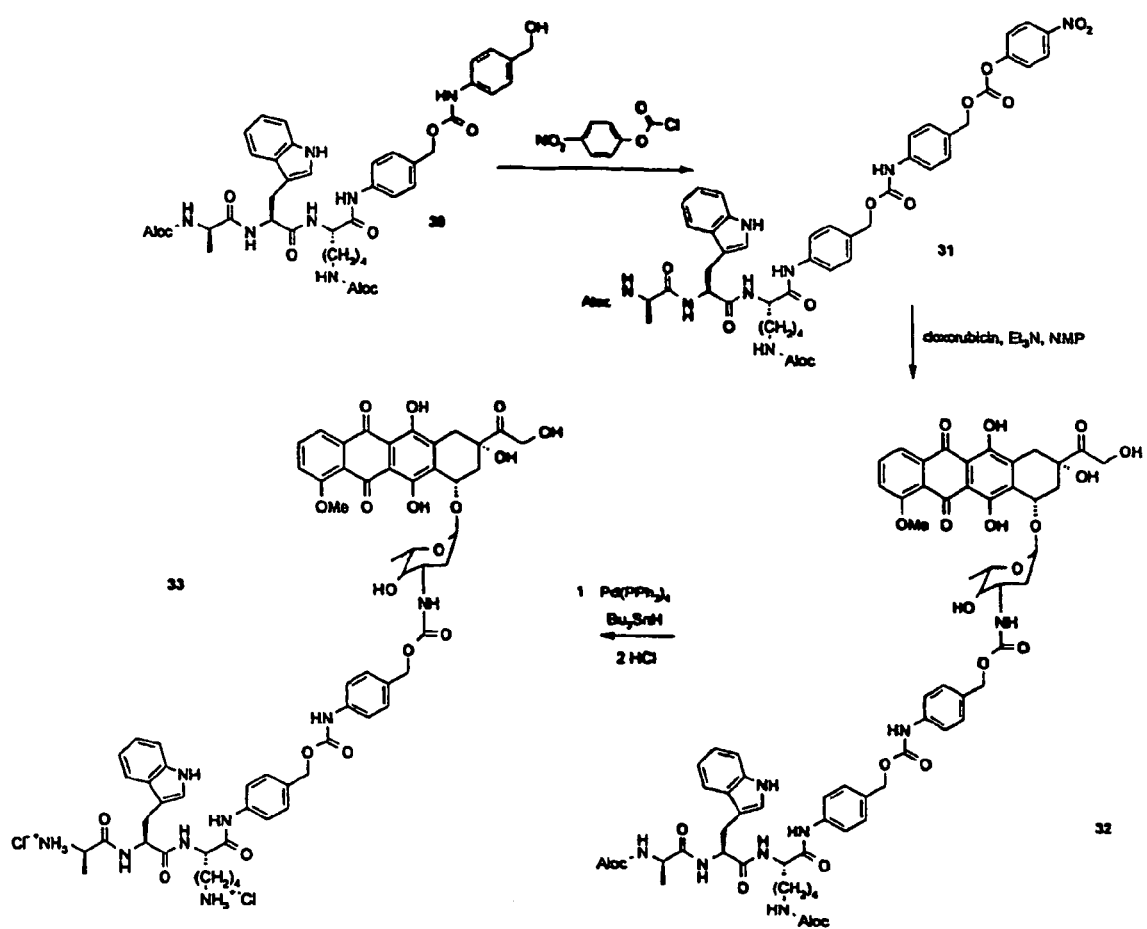
FIG. 18 shows the synthesis of a tryptophan-containing doxorubicin prodrug.
Figures 19, 20:
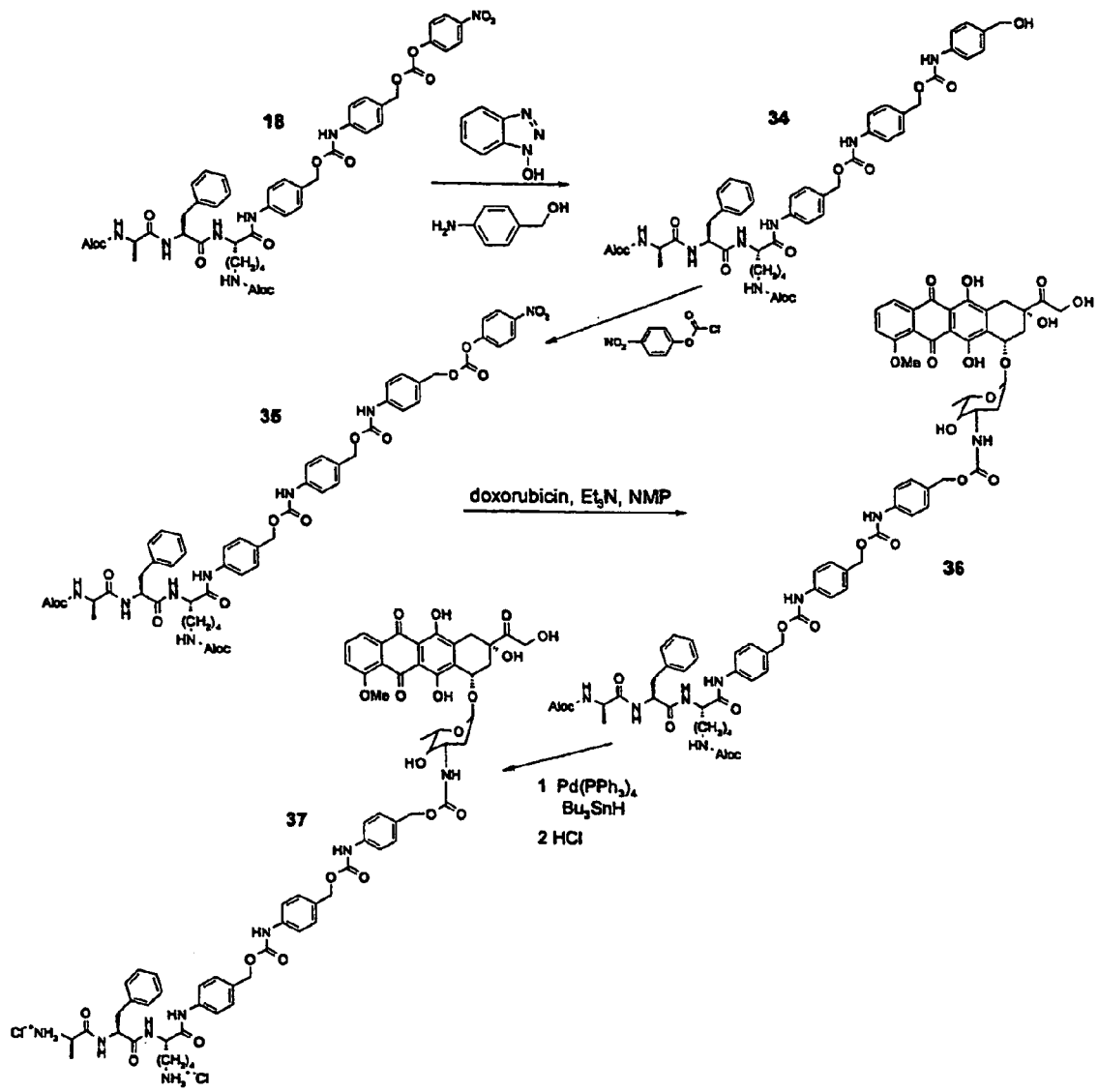
FIG. 19 shows the synthesis of a doxorubicin containing triple 1,6-elimination spacer containing prodrug.
FIG. 20 shows schematically the structure of a prodrug of paclitaxel that contains both an electronic cascade spacer and a cyclisation spacer coupled to the drug via a 2'-carbamate linkage.
Figure 21:
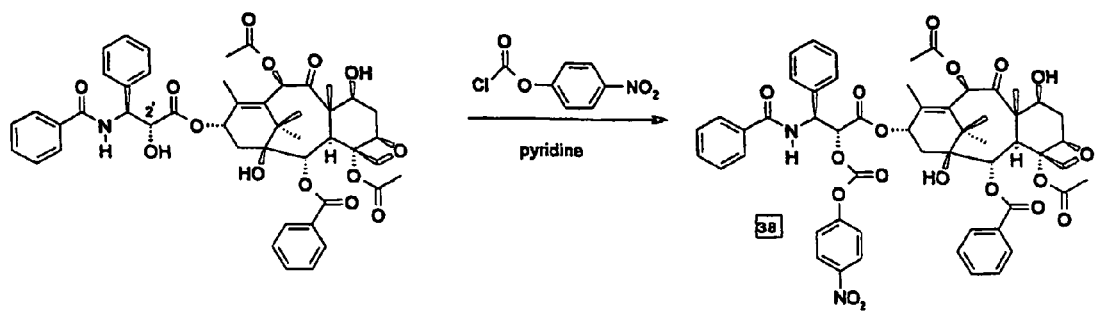
FIG. 21 shows the regioselective synthesis of 2'-(4nitrophenyl carbonate) activated paclitaxel using 4-nitrophenyl chloroformate at low temperature.
Figure 22:
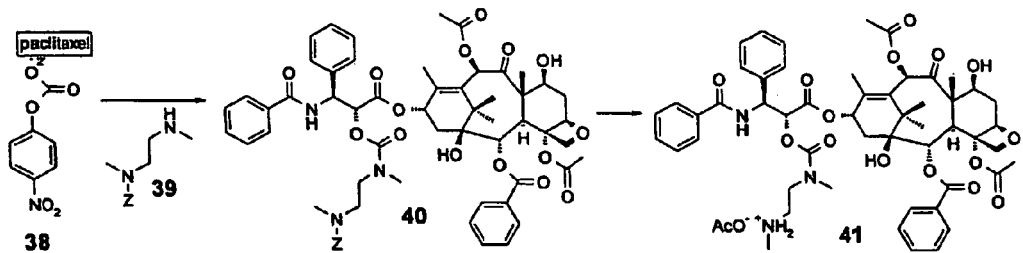
FIG. 22 shows the synthesis of the acid protected paclitaxel-ω-amino aminocarbonyl cyclisation spacer conjugate.
Figure 23:
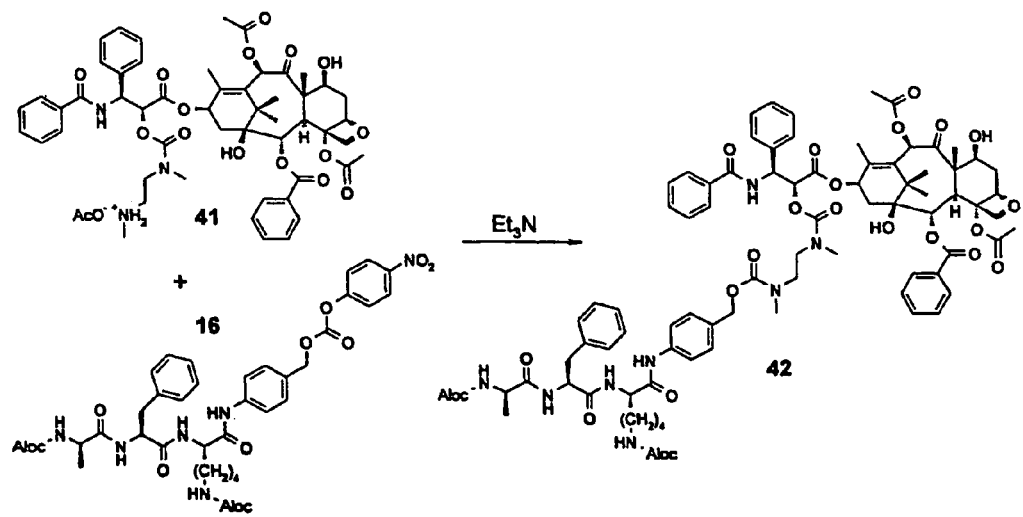
FIG. 23 shows the coupling of the acid protected paclitaxel-ω-amino aminocarbonyl cyclisation spacer conjugate to the 4-nitrophenyl carbonate activated tripeptide-1,6-elimination spacer conjugate.
Figure 24:
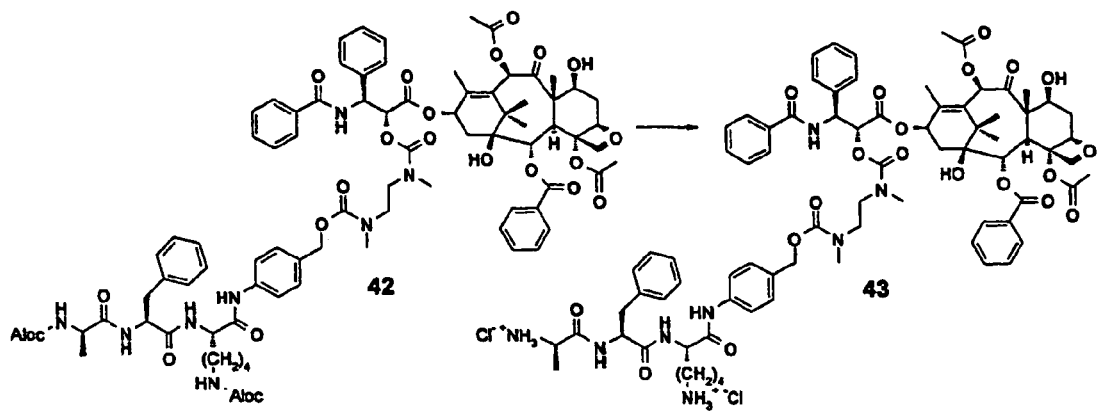
FIG. 24 shows the deprotection reaction to obtain the paclitaxel prodrug that contains a 1,6-elimination spacer and an ω-amino aminocarbonyl cyclisation spacer.
Figure 25:
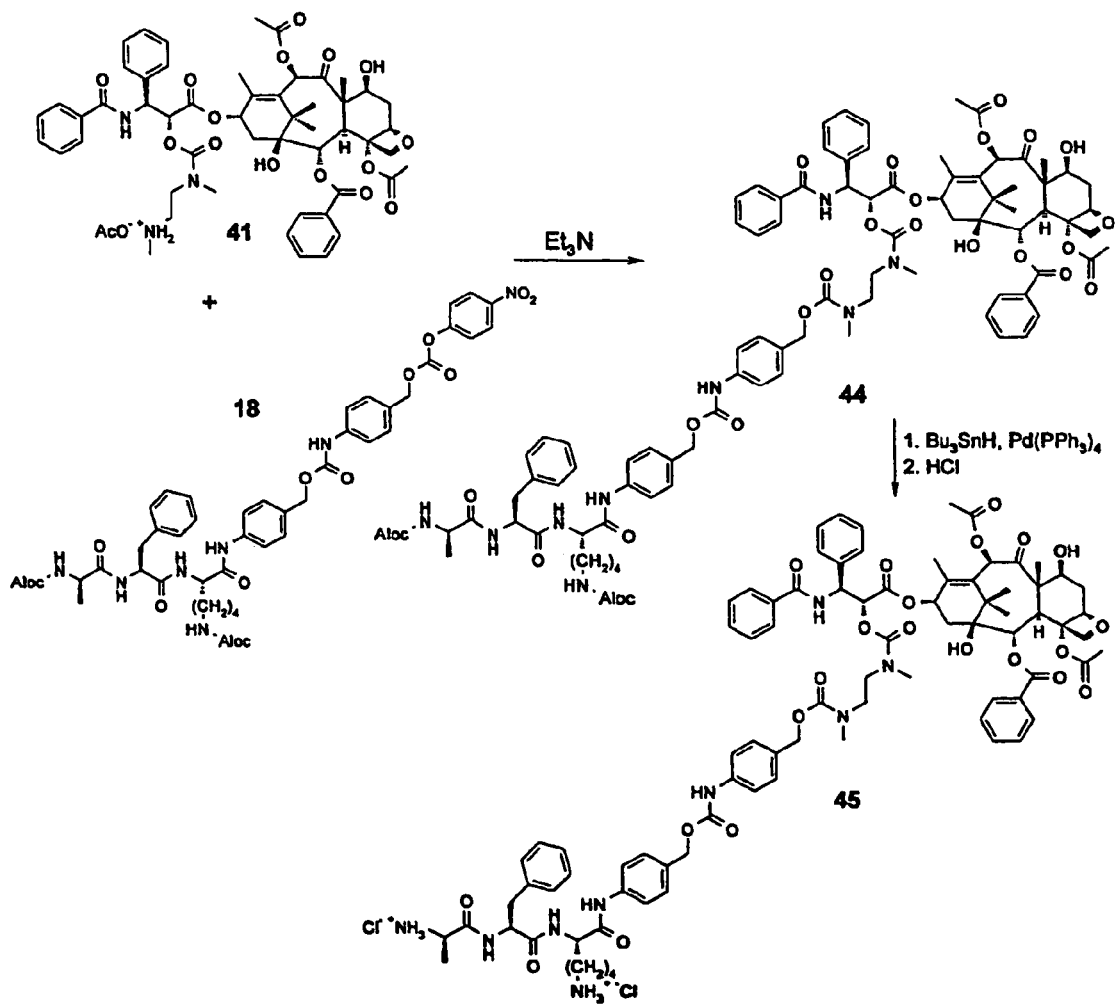
FIG. 25 shows the preparation of a paclitaxel prodrug that contains two 1,6-elimination spacers and an ω-amino aminocarbonyl cyclisation spacer.
Figure 26:
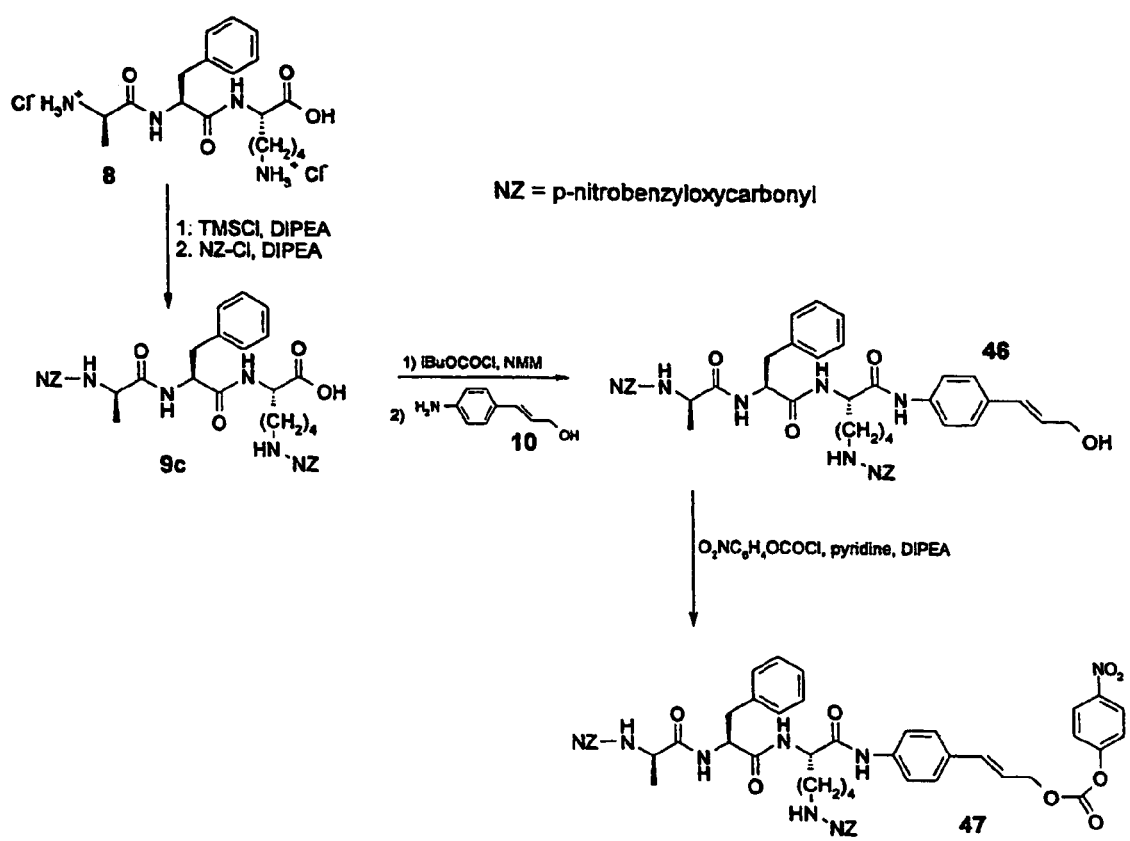
FIG. 26 shows the synthesis of para-nitrophenyl (PNP) carbonate-activated doubly para-nitrobenzyloxycarbonyl-protected tripeptide-spacer conjugate.
Figure 27:
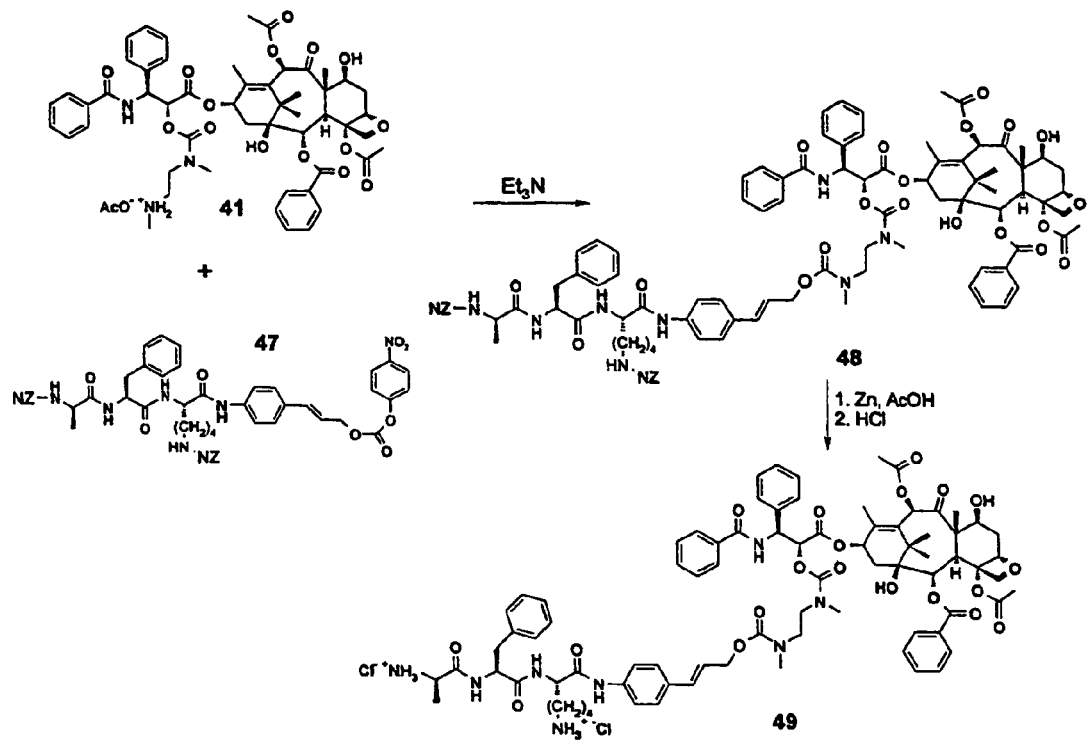
FIG. 27 shows the preparation of a paclitaxel prodrug that contains a 1,8-elimination spacer and an ω-amino aminocarbonyl cyclisation spacer.
Figure 28:
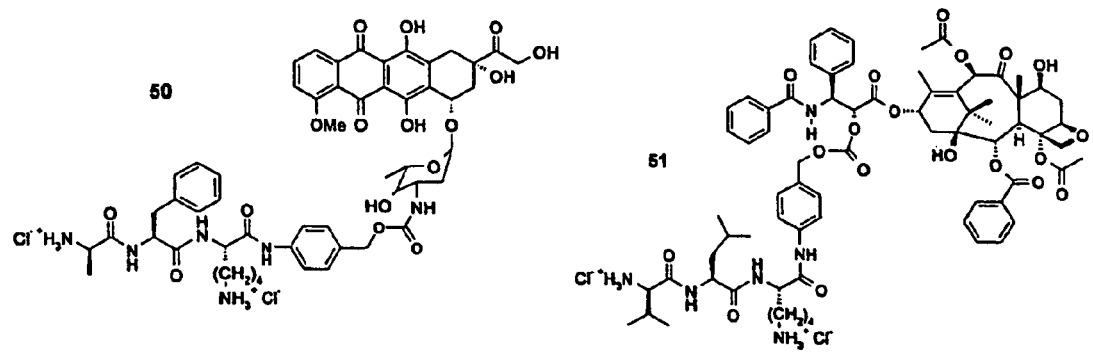
FIG. 28 shows the structure of previously reported doxorubicin and paclitaxel prodrugs containing one electronic cascade spacer.

Synthesis of 2'-[4-nitrocinnamyl carbonate]-paclitaxel 1.

To a solution of 200 mg (1.12 mmol, 4.8 equiv) 4-nitrocinnamyl alcohol in dry dichloromethane/tetrahydrofuran under an Argon atmosphere was added pyridine (94 µl, 5.0 equiv) and 4-nitrophenyl chloroformate (236 mg, 5.0 equiv). The reaction mixture was stirred for 12 h at room temperature. The mixture was cooled to 0° C. and a catalytic amount of DMAP, a few drops of triethyl amine and 200 mg paclitaxel (1.0 equiv) were added. The reaction mixture was stirred at room temperature for 12 h. Solvents were evaporated and the remaining solid was dissolved in dichlorometaane. The organic layer was thoroughly washed with a saturated sodium bicarbonate solution, 0.5 N potassium bisulfate and brine and dried over anhydrous sodium sulfate. After evaporation of the solvents the residual yellow oil was purified by means of column chromatography (ethyl acetate-hexane; 1:1), to yield 144 mg of 1 (58%). M.P. 151° C.; $^1$H-NMR (300 Mz, CDCl$_3$) δ 1.17 (s, 3H, 17), 1.22 (s, 3H, 16), 1.70 (s, 3H, 19), 1.96 (s, 3H, 18), 2.22 (s, 3H, 10-OAc), 2.46 (s, 3H, 4-OAc), 2.55 (m, 1H, 6a), 3.82 (d, 1H, J=7.0 Hz, 3), 4.26 (d, 1H, J=8.4 Hz, 20b), 4.32 (d, 1H, J=8.4 Hz, 20a), 4.39 (m, 1H, 7), 4.87 (bt, 2H, CH$_2$-spacer), 4.99 (bd, 1H, J=7.9 Hz, 5), 5.46 (d, 1H, J=2.8 Hz, 2'), 5.72 (d, 1H, J=7.1 Hz, 2), 6.01 (m, 1H, 3'), 6.26 (bt, 1H, 13), 6.34 (s, 1H, 10), 6.43 (dt, 1H, J=16.0 Hz, HC=C<u>H</u>—CH$_2$), 6.75 (d, 1H, J=16.0 Hz, <u>HC</u>=CH—CH$_2$), 7.35–7.67 (m, 13H, aromatic), 7.75 (d, 2H, J=7.2 Hz, aromatic), 8.15 (d, 2H, J=7.2 Hz, aromatic), 8.19 (d, 2H, J=8.7 Hz, nitrophenyl) ppm; MS (FAB) m/e 1059 (M+H)$^+$, 1081 (M+Na)$^+$; Anal. ($C_{57}H_{58}N_2O_{18}$·2½$H_2O$) calculated C, 62.01%; H, 5.75%; N, 2.54%; measured C, 62.06%; H, 5.31%; N, 2.60%.

Example 2

Principle of 1,8-elimination: Chemical Reduction of the Nitrocinnamyl Carbonate 1.

36 mg of 2'-[nitrocinnamyl carbonate]-paclitaxel 1 was dissolved in 8 ml methanol and 2 ml acetic acid. A catalytic amount of zinc powder was added and the red mixture was stirred for 12 h. Dichloromethane was added and the organic layer was washed with saturated sodium bicarbonate, 0.5 N potassium bisulfate, brine, and water and dried over anhydrous sodium sulfate. After evaporation of the solvents the residual yellow film was purified by means of column chromatography (ethyl acetate-hexane; 2:1), to yield 28 mg of paclitaxel (confirmation by 300 MHz $^1$H-NMR) and 4 mg of unreacted starting compound. When the compound was stirred in the absence of zinc powder under the same conditions, no paclitaxel was formed, indicating that reduction of the nitro group by zinc leads to the release of paclitaxel.

Example 3

Synthesis of Aloc-D-Ala-Phe-Lys(Aloc)-OH 9.

Step a: Synthesis of Fmoc-Phe-Lys(Boc)-OBu 4.

To a solution of 2.50 g Fmoc-Phe-ONSu 2 (ONSu=N-hydroxysuccinimide) (5.16 mmol) in dry dichloromethane under an Argon atmosphere were added at 0° C. 0.791 ml triethyl amine (1.1 eq.) and 1.92 g H-Lys(Boc)OBu.HCl 3 (1.1 eq.). The reaction mixture was stirred at room temperature for 5 hours, then dichloromethane was added and the organic layer was washed with 10% citric acid, saturated sodium bicarbonate and water. The organic layer was dried over anhydrous sodium sulphate and evaporated. The resulting white solid 4 (3.08 g, 89%) was used without further purification. M.P. 93° C.; $^1$H-NMR (300 MHz, CDCl$_3$): δ 1.10–1.90 (m, 24H, 6 $CH_2$-Lys and 18 tert-butyl), 3.06 (m, 2H, N—$CH_2$-Lys and benzylic), 4.19 (t, 1H, Fmoc), 4.25–4.55 (m, 4H, 2 Fmoc and 2 Hα), 7.19–7.78 (m, 13H, aromatic) ppm; MS (FAB) m/e 672 (M+H)$^+$, 694 (M+Na)$^+$; $C_{39}H_{49}N_3O_7$ calculated C, 69.72%; H, 7.35%; N, 6.25%; measured C, 69.69%; H, 7.48%; N, 6.22%.

Step b: Synthesis of Boc-D-Ala-Phe-Lys(Doc)OBu 7.

3.08 g (4.58 mmol) of Fmoc-Phe-Lys(Boc)OBu 4 was dissolved in 100 ml of dioxane/methanol/2N sodium hydroxide (70/25/5) and stirred at room temperature for approximately 1 hour. The reaction mixture was neutralised with acetic acid (0.571 ml) and organic solvents were evaporated. Water and dioxane was added and the solution was freeze dried. Diisopropylether was added to the resulting solid. After filtration, the filtrate was evaporated. The residual product 5 was dissolved in dry dichloromethane and added at 0° C. to a solution of 1.19 g (4.16 mmol) Boc-D-Ala-ONSu 6 and 0.634 ml (1.1 eq.) of triethyl amine in dry dichloromethane. The reaction mixture was stirred overnight after which dichloromethane was added. The organic layer was washed with 10% citric acid, saturated sodium bicarbonate and water. The organic layer was dried over anhydrous sodium sulphate and evaporated. The product was purified by means of column chromatography (SiO$_2$—CHCl$_3$/MeOH 20/1) to afford 2.56 g (4.13 mmol. 99%) of Boc-D-Ala-Phe-Lys(Boc)-OBu 7 as a white foam. M.P. 59° C.; $^1$H-NMR (300 MHz, CDCl$_3$): δ 1.25 (d, 3H, $CH_3$-Ala), 1.43 (bs, 27H, tert-butyl), 1.00–1.90 (m, 6H, $CH_2$-Lys). 2.80–3.30 (m, 4H, N—$CH_2$-Lys and benzylic), 4.15 (m, 1H, Hα), 4.35 (m, 1H, Hα), 4.64 (dd, 1H, Hα), 7.15–7.35 (m, 5H, aromatic) ppm; MS (FAB) m/e 621 (M+H)$^+$, 643 (M+Na)$^+$; $C_{32}H_{52}N_4O_8$ (.1/2$H_2O$) calculated C, 61.03%; H, 8.48%; N, 8.90%; measured C, 61.15%; H, 8.44%; N, 8.66%.

Step c: Synthesis of D-Ala-Phe-Lys-OH 8.

2.56 g (4.13 mmol) Boc-D-Ala-Phe-Lys(Boc)-OBu 7 was stirred in a solution of HCl in EtOAc (3M). After 5 hours the solvent was evaporated, tert-butanol was added and evaporated twice to remove remaining hydrochloric acid. The resulting product was freeze dried in a mixture of dioxane/water to yield a cream coloured powder 8, which was used without further purification. $^1$H-NMR (300 MHz, $D_2O$): δ 0.94 (d, 3H, $CH_3$-Ala), 1.10–1.85 (m, 6H, $CH_2$-Lys), (dd, 1H, Hα), 4.54 (q, 1H, Hα), 7.10–7.22 (m, 5H, aromatic) ppm; MS (FAB) m/e 365 (M+H)$^+$.

Step d: Synthesis of Aloc-D-Ala-Phe-Lys(Aloc)-OH 9.

To solution of 706 mg (1.61 mmol) D-Ala-Phe-Lys-OH 8 in water/acetonitrile was added triethyl amine until a pH of 9–9.5 was reached. Then a solution of 704 mg (2.2 eq.) Aloc-ONSu in acetonitrile was added and the reaction mixture was kept basic by adding triethyl amine. After the pH of the mixture did not alter anymore, a 0.5 M solution of HCl was added until a pH of 3 was reached. The mixture was thoroughly extracted with dichloromethane. The organic layer was washed with water and the water layer was extracted again with dichloromethane. The organic layer was dried over anhydrous sodium sulphate and evaporated to dryness to result in the desired product 9 as a cream coloured foam (742 mg, 86%). M.P. 141° C.; $^1$H-NMR (300 MHz, CDCl$_3$): δ 1.10–1.95 (m, 6H, $CH_2$-Lys), 1.21 (d, 3H, $CH_2$-Ala), 2.90–3.30 (m, 4H, N—$CH_2$-Lys and benzylic), 4.20 (m, 1H, Hα), 4.55 (m, 5H, Hα and 4 Aloc), 4.76 (bd, 1H, Hα), 5.17–5.31 (m, 4H, Aloc), 5.83–5.92 (m, 2H, Aloc), 7.20–7.28 (m, 5H, aromatic) ppm; MS (FAB) m/e 533 (M+H)$^+$, 555 (M+Na)$^+$; $C_{26}H_{36}N_4O_8$ calculated C 58.63%; H, 6.81%; N, 10.52%; measured C, 58.54%; H, 6.81%; N, 10.28%.

Example 4

Synthesis of 4-aminocinnamyl Alcohol 10.

To a solution of 1.5 g (8.37 mmol) of 4-nitrocinnamyl alcohol in THF/methanol (60 mL, 1:1 v/v) was added a catalytic amount of Raney Nickel and hydrazine monohydrate (1.22 mL, 25.1 mmol). The mixture was stirred at room temperature for 3 h, additional hydrazine monohydrate (1.22 mL) being added after 1.5 h. The reaction mixture was filtered over HFLO and concentrated under reduced pressure to 5 mL. Dichloromethane (100 mL) was added and the resultant solution was washed with water, dried over $Na_2SO_4$, filtered, and concentrated, which gave 10 (1.24 g, 8.31 mmol, 99%).

$^1$H NMR (300 MHz, CDCl$_3$) δ 4.24 (d, 2H, J=6.1 Hz, C$H_2$OH), 6.11–6.20 (dt, 1H, J=6.1 Hz, J=15.8 Hz, CH═CH—$CH_2$OH), 6.48 (d, 1H, J=15.8 Hz, C$\underline{H}$═CH—$CH_2$), 6.62 (d, 2H, J=11.1 Hz, aromatic), 7.19 (d, 2H, J=11.0 Hz, aromatic) ppm; MS (EI) m/e 149(M)$^+$.

Example 5

Synthesis of Fmoc-D-Ala-Phe-Lys(Emoc)PACA 11.

To a solution of D-Ala-Phe-Lys-OH 8 (3.20 g, 8.79 mmol) in a 7:3 mixture of water and acetonitrile (300 mL) was added triethylamine until a pH of 8.5 was reached. A solution of Fmoc-OSu (5.93 g, 17.6 mmol) in acetonitrile (50 ml) was added. The pH of the resultant solution was kept at a pH of 8.5–9.0 by the addition of triethylamine. When the pH did no longer change, a 1 N aqueous HCl solution was added to neutralize the solution. The solution was concentrated under reduced pressure to remove acetonitrile. The resultant aqueous solution was extracted 4 times with ethyl acetate. The combined organic layers were dried over $Na_2SO_4$, filtered, and concentrated under reduced pressure. The residue was thoroughly washed with diisopropyl ether to remove apolar contaminations. This gave 5.54 g (6.85 mmol, 78%) of crude 9b.

A solution of 9b (500 mg, 0.618 mmol) in THF (50 mL) was cooled to −40° C. Then, N-methylmorpholine (75 μL, 0.68 mmol) and isobutyl chloroformate (89 μL, 0.68 mmol) were added consecutively. The resultant solution was stirred at −40° C. for 3.5 h. A solution of para-aminocinnamyl alcohol (111 mg, 0.742 mmol) in THF (20 mL) was added slowly. The reaction mixture was stirred at −20° C. for 5 h and then concentrated under reduced pressure. The crude product was purified by means of column chromatography ($SiO_2$—$CH_2Cl_2$/MeOH 93/7). This gave 516 mg of 11 (0.549 mmol, 89%).

$^1$H NMR (300 MF $CDCl_3$/$CD_3OD$) δ 1.17 (d, 3H, J=6.8 Hz, $CH_3$ of Ala), 1.20–2.00 (m, 6H, 3×$CH_2$-Lys), 2.89–3.26 (m, 4H, N—$CH_2$ of Lys and Ph-$CH_2$ of Phe), 3.88–4.58 (m, 11H, $CH_2$ and CH of Fmoc and $CH_2$ of spacer and 3×Hα), 6.21 (dt, 1H, J=15.9 Hz, J=5.8 Hz, CH=CH—C$\underline{H}_2$), 6.48 (d, 1H, J=15.7 Hz, C$\underline{H}$=CH—$CH_2$) 7.15–7.43 (m, 17H, aromatic), 7.52–7.57 (m, 2H, aromatic), 7.67 (d, 1H, J=7.4 Hz, aromatic), 7.71 (d, 1H, J=7.4 Hz, aromatic) ppm; MS (FAB) m/e 940 (M+H)$^+$.

Example 6

Synthesis of Fmoc-D-Ala-Phe-Lys(Fmoc)-PACC-PNP 12.

To a solution of 11 (800 mg, 0.851 mmol) in THF (15 mL) were added at 0° C. DIPEA (594 μL, 3.40 mmol), para-nitrophenyl chloroformate (515 mg, 2.55 mmol), and pyridine (17.3 μL, 0.213 mmol). The reaction mixture was stirred at room temperature for 2 h, after which dichloromethane (50 mL) and water (50 mL) were added. The aqueous layer was separated from the organic layer and extracted with dichloromethane (3×100 mL). The combined organic layers were washed with water, a saturated aqueous $NaHCO_3$ solution, and brine, dried with anhydrous $Na_2SO_4$, filtered, and concentrated under reduced pressure. The residue was washed with a 1:2 mixture of dichloromethane and diethyl ether. This gave 12 (812 mg, 0.734 mmol, 86%).

$^1$H NMR (300 MHz, DMSO-$d_4$) δ 0.95 (d, 3H, J=7.8 Hz, $CH_3$ of Ala), 1.05–1.90 (m, 6H, 3×$CH_2$ of Lys), 2.90 (dd, 1H, J=11.4 Hz, J=15.0 Hz, $CH_2$ of Phe), 3.11 (m, 2H, N—$CH_2$ of Lys), 3.26 (m, 1H, $CH_2$ of Phe), 4.24–4.89 (m, 9H, $CH_2$ and CH of Fmoc and 3×Hα), 5.24 (d, 2H, J=6.6 Hz, CH=CH—C$\underline{H}_2$), 6.81 (dt, 1H, J=17.4 Hz, J=7.0 Hz, CH=C$\underline{H}$—$CH_2$), 7.23 (d, 1H, J=17.4 Hz, C$\underline{H}$=CH—$CH_2$), 7.66–8.25 (m, 23H, aromatic), 8.44–8.48 (m, 4H, aromatic), 8.97 (d, 2H, J=10.1 Hz, aromatic) ppm; MS (FAB) m/e 1105 (M+H)$^+$.

Example 7

Synthesis of Fmoc-D-Ala-Phe-Lys(fmoc)-PACC-DOX 13.

To a solution of 12 (100 mg, 90.5 μmol) in N-methylpyrrolidinone (2 mL) were added triethylamine (13.2 μL, 95.0 μmol) and doxorubicin hydrochloride (55.1 mg, 95.0 μmol). The reaction mixture was stirred at room temperature for 15 h and then poured into 10% isopropanol in ethyl acetate (25 mL). The resultant solution was washed with water, diluted with dichloromethane (50 mL), dried with anhydrous $Na_2SO_4$, filtered, and concentrated under reduced pressure. The crude product was purified by column chromatography ($SiO_2$—$CH_2Cl_2$/MeOH 93/7) and subsequent precipitation from diethyl ether, which gave 13 (82.3 mg, 54.5 μmol, 60%).

$^1$H NMR (300 MHz, DMSO-$d_6$) δ 0.98 (d, 3H, J=6.8 Hz, $CH_3$ of Ala), 1.12 (d, 3H, J=6.7 Hz, 5'-Me), 1.24–2.25 (m, 8H, 3×$CH_2$ of Lys and 2' and 8), 2.79 (m, 1H, $CH_2$ of Phe), 2.97 (m, 4H, N—$CH_2$ of Lys and 10), 3.11 (m, 1H, $CH_2$ of Phe), 3.47 (m, 1H, 4'), 3.74 (m, 1H, 3'), 3.97 (s, 3H, $OCH_3$), 3.97–4.37 & 4.54–4.60 & 4.72 & 4.85 & 4.97 & 5.24 & 5.47 (14H, $CH_2$ and CH of Fmoc and CH=CH—C$\underline{H}_2$ and 1' and 5' and 7 and 14 and OH), 6.20 (m, 1H, CH=C$\underline{H}$—$CH_2$), 6.55 (d, 1H, J=16.2 Hz, C$\underline{H}$=CH—$CH_2$), 7.14–7.93 (m, 32H, aromatic) ppm; MS (FAB) m/e 1533 (M+Na)$^+$.

Example 8

Synthesis of D-Ala-Phe-Lys-PACC-DOX (.2HCl) 14.

To a stirred solution of 50 (40.0 mg, 26.5 μmol) in DMF (2 mL) was added piperidine (128 μL, 1.30 mmol). After 10 min, the reaction mixture was slowly added to a stirred solution of ice-cold diethyl ether. The precipitate was collected by means of centrifugation, washed with diethyl ether, and dissolved in ethyl acetate. An approximately 0.5 M solution of HCl in ethyl acetate (200 μL) was added and the precipitate formed was collected by means of centrifugation. The residue was dissolved in a 2:1 mixture of tert-butanol and chloroform, and the resultant solution was concentrated under reduced pressure. This procedure was repeated twice, yielding 51 (29.4 mg, 25.8 μmol, 97%) as an orange solid after freeze-drying.

$^1$H NMR (300 MHz, $CDCl_3$/$CD_3OD$) δ 1.22 (d, 3H, 5'-Me), 1.29 (d, 3H, $CH_3$ of Ala), 1.30–2.00 (m, 8H, 3×$CH_2$ of Lys and 2'), 2.17 (br.d, 1H, 8), 2.39 (br.d, 1H, 8), 2.93–2,35 (m, 7H, $CH_2$ of Phe and N—$CH_2$ of Lys and 10 and 4'), 3.63 (m, 1H, 3'), 3.85–4.20 (m, 3H, 5' and 2×Hα), 4.07 (s, 3H, $OCH_3$), 4.50–4.78 (m, 5H, Hα and 14 and CH=CH—C$\underline{H}_2$), 5.25 (m, 1H, 1'), 5.48 (m, 1H, 7), 6.15 (m, 1H, CH=C$\underline{H}$—$CH_2$), 6.56 (d, 1H, J=14.6 Hz, C$\underline{H}$=CH—$CH_2$), 7.23–7.56 (m, 10H, aromatic and 3), 7.82 (t, 1H, J=8.0 Hz, 2), 8.01 (m, 1H, 1) ppm; MS (FAB) m/e 1065 (M+H)$^+$.

Example 9

Synthesis of Aloc-D-Ala-Phe-Lys(Aloc)-PABA 15.

A solution of 730 mg (1.37 mmol) protected tripeptide Aloc-D-Ala-Phe-Lys(Aloc)-OH 9 was dissolved in dry THF under an Argon atmosphere and cooled to −40° C. NMM (166 μl, 1.1 eq.) and isobutyl chloroformate (196 μl, 1.1 eq.) were added. The reaction mixture was stirred for 3 hours at a temperature below −30° C. A solution of 4-aminobenzyl alcohol (203 mg, 1.2 eq.) and NMM (181 μl, 1.2 eq.) in dry THF was added dropwise to the reaction mixture. After 2 hours THF was evaporated and dichloromethane was added. The organic layer was washed with saturated sodium bicarbonate, a 0.5 N potassium bisulphate solution and brine, dried over anhydrous sodium sulphate, and evaporated. The residual pale yellow solid was purified by means of column chromatography ($SiO_2$—$CHCl_3$/MeOH 9/1) to afford 812 mg (93%) of the desired product 15 as a cream coloured powder. M.P. 156° C.; $^1$H-NMR (300 MHz, DMSO-D$^6$): δ 0.96 (d, 3H, $CH_3$-Ala), 1.10–1.85 (m, 6H, $CH_2$-Lys), 2.77 (dd, 1H, benzylic Phe), 2.97 (bd, 2H, N—$CH_2$-Lys), 3.09 (dd, 1H, benzylic Phe), 4.00 (t, 1H, Hα), 4.20–4.60 (m, 8H, 2 Hα and 4 Aloc and $CH_2$—OH), 5.00–5.35 (m, 4H, Aloc), 5.76–5.95 (m, 2H, Aloc), 7.05–7.30 (m, 7H, aromatic), 7.41 (d, 1H, NH), 7.56 (d, 2H, aromatic), 8.12 (d, 1H, NH), 8.18 (d, 1H, NH), 9.80 (s, 1H, NH anilide) ppm; MS (FAB) m/e 638 (M+H)$^+$, 660 (M+Na)$^+$; $C_{33}H_{43}N_5O_8$ (.½ $H_2O$) calculated C, 61.29%; H, 6.86%; N, 10.83%; measured C, 61.39%; H, 6.54%; N, 10.55%.

Example 10

Synthesis of Aloc-D-Ala-Phe-Lys(Aloc)-PABC-PNP 16.

To a solution of 384 mg (0.602 mmol) 15 in dry TBF/$CH_2Cl_2$ under an Argon atmosphere, 4-nitrophenyl chloroformate (182 mg, 1.5 eq.) and dry pyridine (73 µl, 1.5 eq.) were added. The reaction mixture was stirred at room temperature for 48 hours, then EtOAc was added. The organic layer was washed with 10% citric acid, brine and water, dried over anhydrous sodium sulphate and evaporated yielding a yellow solid. The product was purified by means of column chromatography ($SiO_2$—$CH_2Cl_2$/MeOH 30/1) to afford 324 mg (67%) of carbonate 16. $^1$H-NMR (300 MHz, $CDCl_3$/$CD_3OD$): δ 1.21 (d, 3H, $CH_3$-Ala), 1.25–2.05 (m, 6H, $CH_2$-Lys), 2.95 (dd, 1H, benzylic Phe), 3.13 (bt, 1H, N—$CH_2$-Lys), 3.27 (dd, 1H, benzylic Phe), 4.08 (dd, 1H, Hα), 4.25 (dd, 1H, Hα), 4.30–4.65 (m, 5H, Hα and 4 Aloc), 5.04–5.35 (m, 4H, Aloc), 5.26 (s, 2H, $CH_2$—OH), 5.65–6.00 (m, 2H, Aloc), 7.10–7.35 (m, 5H, aromatic), 7.39–7.43 (2*d, 4H, aromatic), 7.71 (d, 2H, aromatic), 8.28 (d, 2H, aromatic) ppm; MS (FAB) m/e 803 (M+H)$^+$, 825 (M+Na)$^+$.

Example 11

Synthesis of Aloc-D-Ala-Phe-Lys(Aloc)-PABC-PABA 17.

To a solution of 156 mg (194 µmol) of compound 16 and 26.3 mg (1.1 eq.) PABA in dry N,N-dimethyl formamide under an Argon atmosphere was added diisopropylethyl amine (34 µl, 1.0 eq.) and a catalytic amount of N-hydroxybenzotriazole (7.9 mg, 0.3 eq.). The reaction solution was stirred for 24 hours after which it was diluted with 10% propanol-2/EtOAc. The organic layer was washed with saturated sodium bicarbonate, 0.5 N potassium hydrogensulfate and brine, dried over anhydrous sodium sulfate and evaporated to dryness. The yellow residual film was purified by means of column chromatography ($SiO_2$—$CHCl_3$/MeOH 9/1) to yield 148 mg (97%) of the desired product 17. M.P. 196–197° C.; $^1$H-NMR (300 MHz, $CDCl_3$): δ 1.20 (d, 3H, $^3J$=6.4 Hz, $CH_3$-Ala), 1.27–2.05 (m, 6H, 3 $CH_2$-Lys), 2.99 (dd, 1H, benzylic), 3.14 (m, 2H, N—$CH_2$-Lys), 3.27 (dd, 1H, benzylic), 4.00–4.64 (m, 7H, 3 Hα and Aloc), 4.57 (s, 2H, benzylic-spacer), 5.14 (s, 2H, benzylic-spacer), 5.06–5.37 (m, 4H, Aloc), 5.72 (m, 1H, Aloc), 5.88 (m, 1H, Aloc), 7.10–7.46 (m, 11H, aromatic), 7.64 (d, 2H, $^3J$=8.3 Hz, aromatic) ppm; MS (FAB) m/e 809 (M+Na)$^+$;; $C_{41}H_{50}N_6O_{10}$ (.½$H_2O$) calculated C 61.87%; H, 6.46%; N, 10.56%; measured C, 61.84%; H, 6.38%; N, 10.38%.

Example 12

Synthesis of Aloc-D-Ala-Phe-Lys(Aloc)-PABC-PABC-PNP 18.

A solution of 80.2 mg (102 µmol) of compound 17, pyridine (25 µl, 3.0 eq.) and 4-nitrophenyl chloroformate (44.3 mg, 220 µmol) in dry tetrahydrofuran/dichloromethane was stirred under an Argon atmosphere at 0° C. for two hours and overnight at room temperature. The solution was evaporated in vacuo and the residual product was dissolved in dichloromethane. After washing the organic layer with brine and 0.5 N potassium bisulfate, the organic layer was dried over anhydrous sodium sulfate and concentrated to dryness. The resulting crude product was subjected to column chromatography ($SiO_2$—$CHCl_3$/MeOH 20/1) to obtain 61.9 mg (84%) of compound 18. M.P. 69–70° C.; $^1$H-NMR (300 MHz, $CDCl_3$/$CD_3OD$): δ 1.23 (d, 3H, $^3J$=7.0 Hz, $CH_3$-Ala), 1.10–2.08 (m, 6H, 3 $CH_2$-Lys), 3.04 (m, 1H, benzylic), 3.13 (m, 2H, N—$CH_2$-Lys), 3.27 (bd, 1H, benzylic), 4.06 (m, 1H, Hα), 4.26 (m, 1H, Hα), 4.35–4.70 (m, 5H, Hα and Aloc), 5.04–5.47 (m, 4H, Aloc), 5.14 (s, 2H, benzylic-spacer), 5.24 (s, 2H, benzylic-spacer), 5.72 (m, 1H, Aloc), 5.90 (m, 1H, Aloc), 7.10–7.46 (m, 13H, aromatic), 7.65 (d, 2H, $^3J$=8.3 Hz, aromatic), 8.27 (d, 2H, $^3J$=9.1 Hz, aromatic-PNP) ppm; MS (FAB) m/e 952 (M+H)$^+$, 974 (M+Na)$^+$; $C_{40}H_{46}O_{12}$ (.¼$H_2O$) calculated C, 59.51%; H, 5.81%; N, 10.41%; measured C 59.52%; H, 5.54%; N, 10.12%.

Example 13

Synthesis of Aloc-D-Ala-Phe-Lys(Aloc)-PABC-PABC-DOX 19.

The double spacer containing 4-nitrophenyl carbonate 18 (140 mg, 0.147 mmol) and doxorubicin-HCl (94.1 mg, 1.1 eq.) in N-methylpyrrolidinone were treated at room temperature with triethyl amine (22.5 µl, 1.1 eq.). The reaction mixture was stirred in the dark for 72 hours, again triethyl amine (1.1 eq.) was added and after an additional 24 hours the reaction mixture was diluted with 10% 2-propanol/ethyl acetate. The organic layer was washed with water and brine, and was dried ($Na_2SO_4$). After evaporation of the solvents the crude product was purified by means of column chromatography (chloroform-methanol; 9:1) followed by circular chromatography using a chromatotron supplied with a 2 mm silica plate (chloroform-methanol; 9:1), to yield 72 mg (36%) of protected prodrug 19. M.P. 129° C.; $^1$H-NMR (300 MHz, $CDCl_3$/$CD_3OD$): δ 1.22 (d, 3H, J=7.1 Hz, sugar $CH_3$), 1.27 (d, 3H, J=6.7 Hz, $CH_3$-Ala), 1.25–2.00 (m, 8H, $CH_2$-Lys and 2'), 2.15 (dd, 1H, 8), 2.36 (bd, 1H, 8), 3.04 (bd, 1H, J=18.7 Hz, 10), 2.90–3.50 (m, 5H, benzylic Phe and N—$CH_2$-Lys and 10), 3.37 (bs, 1H, 4'), 3.58 (m, 1H, 3'), 3.85 (m, 1H, Hα), 4.08 (s, 3H, OMe), 4.14 (m, 1H, Hα), 4.29 (dd, 1H, 5'), 4.3–74.68 (m, 5H, Hα and 4 Aloc), 4.76 (s, 2H, 14), 4.96 (s, 2H, benzylic spacer), 5.11 (s, 2H, benzylic spacer), 5.02–5.40 (m, 4H, Aloc), 5.48 (bs, 1H, 1'), 5.61–6.00 (m, 3H, Aloc and 7), 7.08–7.39 (m, 9H, aromatic 5H Phe and 4H spacers), 7.33 (d, 2H, J=8.3 Hz, 2H aromatic spacer), 7.42 (d, 1H, J=8.4 Hz, 3), 7.62 (d, 2H, J=8.0 Hz, 2H aromatic spacer), 7.80 (t, 1H, J=8.1 Hz, 2), 8.03 (d, 1H, J=7.5 Hz, 1) ppm; MS (FAB) m/e 1378 (M+Na)$^+$; Anal. ($C_{69}H_{77}N_7O_{22}$.2$H_2O$) calculated C, 59.52%; H, 5.86%; N, 7.04%; measured C, 59.34%; H, 5.71%; N, 6.66%.

Example 14

Synthesis of H-D-Ala-Phe-Lys-PABC-PABC-DOX.5.7HCl 20.

To a solution of 48 mg (0.035 mmol) protected prodrug 19 in dry tetrahydrofuran/dichloromethane under an argon atmosphere was added morpholine (31 µl, 10 eq.) together with a catalytic amount of $Pd(PPh_3)_4$. The reaction mixture was stirred for one hour in the dark. The red precipitate was collected by means of centrifugation. Ethyl acetate was added and the mixture was acidified using 1.0 ml of 0.5 M hydrochloric acid/ethyl acetate. The precipitate was collected by means of centrifugation and washed several times with ethyl acetate. Tert-butanol was added and evaporated and the resulting red film was freeze dried in water yielding 37 mg (83%) of prodrug 20. Mp>300° C.; $^1$H-NMR (300 MHz, $CDCl_3/CD_3OD$): δ 1.20 (d, 3H, J=7.0 Hz, sugar $CH_3$), 1.27 (d, 3H, J=6.5 Hz, $CH_3$-Ala), 1.38–2.05 (m, 8H, $CH_2$-Lys and 2'), 2.18 (dd, 1H, 8), 2.36 (bd, 1H, 8), 2.82–3.41 (m, 6H, benzylic Phe and N—$CH_2$-Lys and 10), 3.37 (s, 1H, 4'), 3.60 (bs, 1H, 3'), 4.02 (m, 1H, Hα), 4.08 (s, 3H, OMe), 4.18 (1,1H, Hα), 4.53 (dd, 1H, 5'), 4.66 (dd, 1H, Hα), 4.77 (s, 2H, 14), 4.95 (bs, 2H, benzylic spacer), 5.14 (s, 2H, benzylic spacer), 5.27 (bs, 1H, 1'), 5.48 (bs, 1H, 7), 7.09–7.50 (m, 11H, aromatic 5H Phe and 6H spacers and 3), 7.58 (d, 2H, J=8.4 Hz, 2H aromatic spacer), 7.82 (t, 1H, J=8.0 Hz, 2), 8.03 (d, 1H, J=7.6 Hz, 1) ppm; MS (FAB) m/e 1188 (M+H)$^+$, m/e 1210 (M+Na)$^+$; Anal. (duplo) ($C_{61}H_{69}N_7O_{18}$.5.7HCl) calculated C, 52.42%; H, 5.39%; N, 7.01%; measured C, 52.38%; H 5.71%; N, 7.14%.

Example 15

Synthesis of 2'-[Aloc-D-Ala-Phe-Lys(Aloc)-PABC-PABC]-paclitaxel 21.

4-Nitrophenyl carbonate 18 (47.4 mg, 49.8 µmol) and paclitaxel (42.3 mg, 1.0 eq.) in dry tetrahydrofuran/dichloromethane under an Argon atmosphere were treated at room temperature with N,N-dimethyl-4-aminopyridine (DMAP) (6.7 mg, 1.1 eq.). The reaction mixture was stirred in the dark for 48 hours and was then concentrated to dryness. The product was dissolved in dichloromethane and the organic layer was washed with saturated sodium bicarbonate, 0.5 N potassium bisulfate and brine and dried over anhydrous sodium sulfate. After evaporation of the solvents the residual yellow film was purified by means of column chromatography ($SiO_2$—EtOAc/Hex/MeOH 5/5/1), to yield 67.5 mg (82%) of the desired protected paclitaxel prodrug 21. M.P. 137–138° C.; $^1$H-NMR (300 Mz, $CDCl_3$): δ 1.14 (s, 17), 1.23 (s, 3H, 16), 1.27 (d, 3H, $^3$J=7.1 Hz, $CH_3$-Ala), 1.05–2.10 (m, 6H, $CH_2$-Lys), 1.67 (s, 3H, 19), 1.89 (s, 3H, 18), 2.22 (s, 3H, 10-OAc), 2.44 (s, 3H, 4-OAc), 2.97 (m, 1H, benzylic), 3.14 (m, 2H, N—$CH_2$-Lys), 3.21 (m, 1H, benzylic), 3.81 (d, 1H, $^3$J=7.0 Hz, 3), 4.03 (m, 1H, Hα), 4.20 (d, 1H, $^2$J=8.4 Hz, 20b), 4.31 (d, 1H, $^2$J=8.4 Hz, 20a), 4.43 (m, 1H, 7), 4.34–4.74 (m, 6H, Hα and Aloc), 4.90–5.37 (m, 11H, 2 Hα, Aloc, 5 and 2 benzylic-spacer), 5.44 (d, 1H, $^3$J=2.9 Hz, 2'), 5.63 (m, 1H, Aloc), 5.69 (d, 1H, $^3$J=7.1 Hz, 2), 5.87 (m, 1H, Aloc), 5.97 (bd, 1H, $^3$J=2.9 Hz, $^3$J=9.2 Hz, 3'), 6.26 (m, 1H, 13), 6.29 (m, 1H, 10), 7.05–7.80 (m, 26H, aromatic), 8.14 (d, 2H, 3J=7.2 Hz, aromatic) ppm; MS (FAB) m/e 1668 (M+H)$^+$, 1689 (M+Na)$^+$; $C_{89}H_{99}N_7O_{25}$ (.2$H_2O$) calculated C, 62.78%; H, 6.10%; N, 5.76%; measured C, 62.55%; H, 5.82%; N, 5.57%.

Example 16

Synthesis of 2'-[H-D-Ala-Phe-Lys-PABC-PABC]-paclitaxel (.2HCl) 22.

To a solution of 51.4 mg (30.8 µmol) protected prodrug 21 in dry tetrahydrofuran under an Argon atmosphere was added glacial acetic acid (8.9 µl, 5 eq.) together with tributyltinhydride (24.6 µl, 3 eq) and a catalytic amount of $Pd(PPh_3)_4$. After 30 minutes the reaction mixture carefully 1 ml 0.5 M HCl/EtOAc was added to the reaction solution. The product was precipitated by addition of diethyl ether and the white precipitate was collected by means of centrifugation and washed several times with ether. Tert-butanol was added and evaporated again to remove an excess of HCl and the resulting product was dissolved in water and freeze dried yielding 46.9 mg (100%) of the desired prodrug 22. M.P. >192° C. (dec.); $^1$H-NMR (300 MHz, $CDCl_3/CD_3OD$): δ 1.15 (s, 3H, 17), 1.21 (s, 3H, 16), 1.10–2.00 (m, 9H, $CH_2$-Lys and $CH_3$-Ala), 1.67 (s, 3H, 19), 1.90 (s, 3H, 18), 2.20 (s, 3H, 10-OAc), 2.43 (s, 3H, 4-OAc), 2.85 (m, 4H, benzylic and N—$CH_2$-Lys), 3.80 (d, 1H, $^3$J=6.9 Hz, 3), 4.24 (d, 1H, $^2$J=8.4 Hz, 20b), 4.31 (d, 1H, $^2$J=8.4 Hz, 20a), 4.39 (dd, 1H), 4.56 (m, 1H, Hα), 5.68 (m, 1H, Hα), 4.98 (d, 1H, 5), 5.08 (m, 4H, 2 benzylic-spacer), 5.43 (d, 1H, $^3$J=2.7 Hz, 2'), 5.70 (d, 1H, $^3$J=7.0 Hz, 2), 5.97 (m, 1H, 3'), 6.22 (m, 1H, 13), 6.32 (m, 1H, 10), 7.05–7.68 (m, 24H, aromatic), 7.71 (d, 1H, $^3$J=7.2 Hz, aromatic), 8.14 (d, 2H, $^3$J=7.3 Hz, aromatic) ppm; MS (FAB) m/e 1499 (M+H)$^+$, 1521 (M+Na)$^+$; $C_{81}H_{91}N_7O_{21}$ (.3.7HCl) calculated C, 59.60%; H, 5.85 %; N, 6.01%; measured C, 59.60%; H, 5.88%; N, 5.98%.

Example 17

Synthesis of Fmoc-Trp-Lys(Boc)-OBu 24.

To a solution of 3.00 g (5.73 mmol) Fmoc-Trp-ONSu 23 in dry dichloromethane under an argon atmosphere were added at 0° C. 0.791 ml (1.00 equiv) triethylamine and 2.12 g (1.10 equiv) H-Lys (Boc)-OBu.HCl. The mixture was stirred at rt for 5 hours, then dichloromethane was added and the organic layer was washed with 10% citric acid, saturated sodium bicarbonate and water, dried over sodium sulfate and evaporated. The white solid 24 (3.52 g, 86%) was used without further purification. $^1$H-NMR (300 MHz, $CDCl_3$): δ 1.10–1.92 (m, 24H, 3 $CH_2$-Lys and 18 t-Bu), 2.80–3.20 (m, 3H, N—$CH_2$-Lys and $CH_2$-Trp), 3.52 (d, 1H, $CH_2$-Trp), 4.19 (t, 1H, Fmoc), 4.29–4.82 (m, 5H, 2 Fmoc, 2 Hα and NH), 6.54 (d, H, Aryl), 7.06-7.76 (m, 12H, aromatic) ppm; MS (FAB) m/e 1444 (2M+Na); Anal. ($C_{41}H_{50}N_4O_7$.4$H_2O$) C, H, N calculated C, 62.90%; H, 6.30%; N, 7.15%; measured C, 63.22%; H, 6.49%; N, 7.13%.

Example 18

Synthesis of Boc-D-Ala-Trp-Lys(oc)-OBu 26.

3.52 g (4.95 mmol) of Fmoc-Trp-Lys(Boc)-OBu 24 was dissolved in 100 ml of dioxane/methanol/2N sodium hydroxide (70/25/5) and stirred at rt for 1 hour. The mixture was neutralized with acetic acid (0.570 ml) and organic solvents were evaporated. Water and dioxane were added and the solution was freeze dried. Diisopropylether was added and after filtration the filtrate was evaporated. The product was dissolved in dry dichloromethane and added at 0° C. to a solution of 1.41 g (4.93 mmol) Boc-D-Ala-ONSu 6 and 0.756 ml (1.10 equiv) of triethylamine in dry dichloromethane. The mixture was stirred for 16 hours after which dichloromethane was added. The organic layer was washed with 10% citric acid, saturated sodium bicarbonate and water, and dried over sodium sulfate and evaporated. The product was purified by means of column chromatography ((SiO$_2$—first ethyl acetate/heptane 1/1 and then CHCl$_3$/MeOH; 9/1) to afford 2.26 g (3.42 mmol, 69%) of the tripeptide 26 as white foam. $^1$H-NMR (300 MHz, CDCl$_3$): δ 0.99–1.90 (m, 36H, 3 CH$_2$-Lys, CH$_3$-Ala and 3 t-Bu), 2.80–3.50 (m, 4H, N—CH$_2$-Lys and 2 CH$_2$-Trp), 3.99 (m, 1H, Hα), 4.33 (m, 1H, Hα), 4.77 (br d, 1H, Hα), 6.90–7.65 (m, 5H, aromatic) ppm; MS (AB) m/e 660 (M+H)$^+$, 682 M+Na)$^+$; Anal. (C$_{34}$H$_{53}$N$_5$O$_8$.H$_2$O)C, H, N calculated C, 60.25%; H, 8.17%; N, 10.33%; measured C, 60.47%; H, 8.08%; N, 9.73%.

Example 19

Synthesis of Aloc-D-Ma-Trp-Lys(Aloc)-OH 28.

2.56 g (4.13 mmol) Boc-D-Ala-Trp-Lys (Boc)-OBu (26) was stirred in a solution of hydrochloric acid in ethyl acetate (3M). After 5 hour the solvent was evaporated, tert-butanol was added and evaporated twice to remove remaining hydrochloric acid. The product was freeze dried in dioxane/water to yield a brown coloured powder.

To a solution of 706 mg (1.61 mmol) D-Ala-Phe-Lys-OH 27 in water/acetonitrile was added triethylamine until a pH of 9–9.5 was reached. Then a solution of 1.58 g (2.20 equiv) Aloc-ONSu in acetonitrile was added and the mixture was kept basic by adding triethylamine. After the pH of the mixture did not alter anymore, a 0.5 M solution of hydrochloric acid in ethyl acetate was added until a pH of 3 was reached. The mixture was thoroughly extracted with dichloromethane. The organic layer was washed with water, dried (Na$_2$SO$_4$) and evaporated. The cream coloured product 28 was used without further purification. $^1$H-NMR (300 MH, CDCl$_3$): δ 1.00–1.80 (m, 9H, 3 CH$_2$-Lys and CH$_2$-Ala), 2.80–3.35 (m, 4H, N—CH$_2$-Lys and CH$_2$Trp), 4.13 (m, 1H, Hα), 4.14 (m, 1H, Hα). 4.30–4.95 (m, 6H, 4 Aloc and 2 Hα), 5.01–5.40 (m, 5H, 4 Aloc and Hα), 5.70–6.30 (m, 3H, 2 Aloc and NH), 6.90–7.70 (m, 5H, aromatic) ppm; MS (FAB) m/e 572 (M+H)$^+$, 594 (M+Na)$^+$; Anal. (C$_{29}$H$_{37}$N$_5$O$_8$.1 ½H$_2$O) calculated C, 56.18%; H, 6.44%; N, 11.70%; measured C, 56.07%; H, 6.22%; N, 11.21%.

Example 20

Synthesis of Aloc-D-Ala-Trp-Lys(Aloc)-PABA 29.

A solution of 239 mg (0.419 mmol) Aloc-D-Ala-Trp-Lys(Aloc)-OH 28 was dissolved in dry tetrahydrofuran under an argon atmosphere and cooled to −40° C. N-methylmorpholine (48.3 µl, 1.05 equiv) and isobutylchloroformate (57.0 µl, 1.05 equiv) were added. The reaction mixture was stirred for 2 hours at a temperature below −30° C. A solution of 4-aminobenzyl alcohol (51.5 mg, 1.00 equiv) and N-methylmorpholine (50.6 µl, 1.1 equiv) in dry THF was added dropwise to the reaction mixture. After 2 hours tetrahydrofuran was evaporated and dichloromethane was added. The organic layer was washed with saturated sodium bicarbonate, a 0.5 N potassium bisulphate solution and brine, dried (Na$_2$SO$_4$) and evaporated to afford 265 mg (94%) of the desired product 29 as a cream coloured powder. $^1$H-NMR (300 MHz, CDCl$_3$/CD$_3$OD): δ 1.00–1.62 (m, 9H, CH$_3$-Ala and 3 CH$_2$-Lys), 2.90–3.70 (m, 4H, N—CH$_2$-Lys and CH$_2$-Trp), 4.48–4.92 (m, 7H, 2 Hα and 4 Aloc), 4.72 (s, 2H, CH$_2$—OH), 5.00–5.50 (m, 5H, 4 Aloc and Hα), 5.35–6.05 (m, 2H, Aloc), 6.80–7.83 (m, 9H, aromatic) ppm; MS (FAB) m/e 677 (M+H)$^+$, 699 (M+Na)$^+$.

Example 21

Synthesis of Aloc-D-Ala-Trp-Lys(Aloc)-PABC-PNP.

To a solution of 384 mg (0.602 mmol) of Aloc-D-Ala-Trp-Lys(Aloc)-PABA 29 in dry tetra hydrofuran/dichloromethane under an argon atmosphere, 4-nitrophenylchloroformate (182 mg, 1.50 equiv) and dry pyridine (73 µl, 1.50 equiv) were added. The mixture was stirred at rt for 48 hours, and then ethyl acetate was added. The organic layer was washed with 10% citric acid, brine and water, dried Na$_2$SO$_4$) and evaporated yielding a yellow solid. The product was purified by means of column chromatography (SiO$_2$—CHCl$_3$/MeOH; 30/1) to afford 324 mg (67%) of carbonate Aloc-D-Ala-Trp-Lys(Aloc)-PABC-PNP as a cream coloured powder. $^1$H-NMR (300 MHz, CDCl$_3$/CD$_3$OD): δ 1.00–2.10 (m, 9H, CH$_3$-Ala and 3 CH$_2$-Lys), 2.90–3.70 (m, 4H, N—CH$_2$-Lys and CH$_2$-Trp), 3.64 (m, 1H, Hα), 3.81 (m, 1H, Hα), 4.38–4.81 (m, 5H, Hα and 4 Aloc), 5.10–5.35 (m, 4H, Aloc), 5.21 (s, 2H, CH$_2$—OH), 5.40–6.00 (m, 2H, Aloc), 7.00–7.85 (m, 11H, aromatic), 8.25 (d, 2H, J=8.1, aromatic); MS (FAB) m/e 842 (M+H)$^+$, 864 (M+Na)$^+$.

Example 22

Synthesis of Aloc-D-Ala-Trp-Lys(Aloc)-PABC-PABA 30.

To a solution of 219 mg (260 µmol) of Aloc-D-Ala-Trp-Lys(Aloc)PABC-PNP and 35.2 mg (1.1 equiv) 4-aminobenzyl alcohol in dry N,N-dimethylformamide under an Argon atmosphere was added diisopropylethylamine (45.3 µl, 1.00 equiv) and a catalytic amount of N-hydroxybenzotriazole (10.5 mg, 0.30 equiv). The reaction solution was stirred for 48 hours after which it was diluted with 10% propanol-2/EtOAc. The organic layer was washed with saturated sodium bicarbonate, 0.5 N potassium bisulfate and brine, dried over anhydrous sodium sulfate and evaporated to dryness. The pale yellow residual film was purified by means of column chromatography (SiO$_2$—CHCl$_3$/MeOH 15/1) to yield 192 mg (89%) of the desired product 30. $^1$H-NMR (300 MHz, CDCl$_3$): δ 0.90–2.10 (m, 9H, CH$_3$-Ala and 3 CH$_2$-Lys), 2.90–3.70 (m, 4H, N—CH$_2$-Lys and CH$_2$-Trp), 4.08 (m, H, Hα), 4.40–4.86 (m, 6H, 2 benzylic-spacer and 4 Aloc), 4.90–5.40 (m, 7H, 2 benzylic-spacer Hα and Aloc), 5.50 (m, 1H, Aloc), 5.92 (m, 1H, Aloc), 6.72–7.82 (m, 13H, aromatic) ppm; MS (FAB) m/e 848 (M+Na)$^+$; (C$_{43}$H$_{51}$N$_7$O$_{10}$ .2¾H$_2$O) calculated C, 58.99%; H, 6.50%; N, 11.20%; measured C, 59.15%; H, 6.25%; N 11.15%.

Example 23

Synthesis of Aloc-D-Ala-Trp-Lys(Aloc)-PABC-PABC-PNP 31.

A solution of 70 mg (85 µmol) of compound 30, pyridine (17 µl, 2.5 equiv) and 4-nitrophenylchloroformate (34 mg, 2.0 equiv) was stirred under an Argon atmosphere at 0° C. for two hours and for 24 hours at room temperature. The solution was evaporated in vacuo and the residual product was dissolved in chloroform. After washing the organic layer with brine and 0.5 N potassium bisulfate, the organic layer was dried over anhydrous sodium sulfate and concentrated to dryness. The resulting crude product was subjected to column chromatography (SiO$_2$—CHCl$_3$/MeOH 20/1) to obtain 54 mg (64%) of 31 as a pale yellow solid. $^1$H-NMR (300 MHz, CDCl$_3$/CD$_3$OD): δ 0.90–2.10 (m, 9H, CH$_3$-Ala and 3 CH$_2$-Lys), 2.90–3.10 (m, 4H, N—CH$_2$-Lys and CH$_2$-

Trp), 3.27 (bd, 1H, benzylic), 4.35–4.78 (m, 6H, 2Hα and Aloc), 4.90–5.52 (m, 4H, Aloc), 5.13 (s, 2H, benzylic-spacer), 5.60 (m, 1H, Aloc), 5.94 (m, 1H, Aloc), 7.10–7.46 (m, 15H, aromatic), 8.36 (d, 2H, aromatic-PNP) ppm; MS (FAB) m/e 991 (M+H)$^+$, 1013 (M+Na)$^+$; $C_{50}H_{54}N_{54}N_8O_{14}·¾H_2O$) calculated C 59.78%; H, 5.57 %; N, 11.15%; measured C, 60.12%; H, 5.89%; N, 10.76%.

Example 24

Synthesis of Aloc-D-Ala-Trp-Lys(Aloc)-PABC-PABC-DOX 32.

The double spacer-containing 4-nitrophenylcarbonate 31 (41 mg, 0.041 mmol) and doxorubicin-HCl (26 mg, 1.1 equiv) in N-methylpyrrolidinone were treated at room temperature with triethylamine (6.3 μl, 1.1 equiv). The reaction mixture was stirred in the dark for 48 hours, again triethylamine (1.1 equiv) was added and after an additional 24 hours the reaction mixture was diluted with 10% 2-propanol/ethyl acetate. The organic layer was washed with water and brine, and was dried ($Na_2SO_4$). After evaporation of the solvents the crude product was purified by means of column chromatography ($SiO_2$—$CHCl_3$/MeOH; 9/1) followed by circular chromatography using a chromatotron supplied with a 2 mm silica plate (chloroform-methanol; 9/1), to yield 45 mg (78%) of the protected prodrug 32. $^1$H-NMR (300 MHz, $CDCl_3$/$CD_3OD$): δ 0.92–1.52 (m, 13H, sugar $CH_3$, $CH_3$-Ala, 3 $CH_2$-Lys and 2'), 2.15 (dd, 1H, 8), 2.36 (bd, 1H, 8), 3.18 (bd, 1H, 10), 2.90–3.10 (m, 5H, N—$CH_2$-Lys and $CH_2$-Trp and 10), 3.59 (bs, 1H, 4'), 3.82 (m, 1H, 3'), 3.85 (m, 1H, Hα), 4.11 (s, 3H, OMe), 4.21 (m, 1H, Hα), 4.45 (dd, 1H, 5'), 4.30–4.62 (m, 5H, Hα and 4 Aloc), 4.76 (s, 2H, 14), 4.96 (s, 2H, benzylic spacer), 5.11 (s, 2H, benzylic spacer), 5.513–5.4 (m, 2H, Aloc), 5.48 (bs, 1H, 1'), 5.58 (m, 2H, Aloc and 7), 5.91(m, 2H, Aloc), 6.70–7.39 (m, 11H, aromatic 5 Trp and 6 spacers), 7.41 (d, 1H, J=8.4 Hz, 3), 7.63 (d, 2H, aromatic spacer), 7.78 (t, 1H, 2), 8.03 (d, 1H, J=7.6 Hz, 1) ppm; MS (FAB) m/e 1417 (M+Na)$^+$.

Example 25

Synthesis of D-Ala-Trp-Lys-PABC-PABC-DOX (.7½ HCl) 33.

To a solution of 36 mg (0.026 mmol) protected prodrug 32 in dry THF/dichloromethane under an argon atmosphere was added morpholine (22 μl, 10 equiv) together with a catalytic amount of $Pd(PPh_3)_4$. The reaction mixture was stirred for 1 hour in the dark. The red precipitate was collected by means of centrifugation. Ethyl acetate was added and the mixture was acidified using 0.5 ml of 1 M hydrochloric acid/ethyl acetate. The precipitate was collected by means of centrifugation and washed several times with ethyl acetate. Tert-butanol was added and evaporated and the resulting red film was freeze dried in water yielding 28 mg (72%) of the doxorubicin prodrug 33. $^1$H-NMR (300 MHz, $CDCl_3$/$CD_3OD$): δ 1.10–1.96 (m, 13H, $CH_3$-Ala, $CH_3$-sugar, 3 $CH_2$-Lys and 2'), 2.09 (m, 1H, 8), 2.35 (bd, 1H, J=15.1 Hz, 8), 2.79–3.39 (m, 3H, N—$CH_2$-Lys, $CH_2$-Trp and 10), 3.60 (s, 1H, 4'), 4.00 (bs, 1H, 3'), 4.09 (s, 3H, OMe), 4.54 (m, 1H, 5'), 4.77 (s, 2H, 14), 4.97 (2*d, 2H, Bn spacer), 5.13 (s, $CH_2$, Bn spacer), 5.28 (bs, 1H, 1'), 5.48 (bs, 1H, 7), 6.99–7.72 (m, 12H, 5 Trp and 6 spacer), 7.62 (d, 1H, 7.6 Hz, 3), 7.55 (d, 2H, J=8.2 Hz, aromatic spacer), 7.83 (t, 1H, 2), 8.05 (d, 1H, J=7.7 Hz, 1) ppm; MS (FAB) m/e 1228 (M+H)$^+$; Anal. ($C_{63}H_{70}N_8O_{18}·7$ $^{1/2}$HCl) calculated C, 50.42%; H, 5.21%; N, 7.47%; measured C, 50.56%; H, 5.48%; N, 7.35%.

Example 26

Synthesis of Aloc-D-Ala-Phe-Lys(Aloc)-PABC-PABC-PABA 34.

100 mg (0.105 mmol) of Aloc-D-Ala-Phe-Lys(Aloc)-PABC-PABC-PNP 18 was dissolved in dry N,N-diethylformamide under an argon atmosphere and cooled to –8° C. 4-Aminobenzylalcohol (14.2 mg, 1.1 equiv), dipea (18.3 μl, 1.0 equiv) and 1-hydroxybenzotriazole (HOBt) (4 mg, 0.3 equiv) were added. The reaction mixture was stirred for 48 hours at room temperature, and diluted with 10% 2-propanol/ethyl acetate. The organic layer was washed with water, saturated sodium bicarbonate, 0.5 N potassium bisulfate, and brine, dried over sodium sulfate ($Na_2SO_4$), and evaporated to yield the desired product 34 as a cream colored powder 86 mg (88%). $^1$H NMR (300 MHz $CDCl_3$) δ 0.95–2.05 (m, 9H, 3$CH_2$-Lys and $CH_3$-Ala), 2.88–3.11 (m, 4H, 2H Bn-Phe and N—$CH_2$-Lys), 3.95–4.62 (m, 7H, 3Hα and 4H Aloc), 4.75 (s, 2H, $CH_2$—OH), 5.12–5.21 (m, 6H, 4 Aloc and $CH_2$-Bn), 5.09 (s, 2H, $CH_2$-Bn), 5.65–6.00 (m, 2H, Aloc), 6.79–7.41 (m, 15H, aromatic) 7.62 (d, 2H, aromatic) ppm; MS (FAB) m/e 959 (M+Na)$^+$.

Example 27

Synthesis of Aloc-D-Ala-Phe-Lys(Aloc)-PABC-PABC-PABC-PNP 35.

To a solution of 59 mg (0.063 mmol) of Aloc-D-Ala-Phe-Lys(Aloc)-PABC-PABC-PABA 34 in dry tetrahydrofuran and dichloromethane under an argon atmosphere, were added at –40° C. respectively pyridine (13 μl, 2.5 equiv) and 4-nitrophenyl chloroformate (25 mg, 2.0 equiv). After stirring for 4.5 hours at –40° C. and overnight at 6° C., pyridine (10 μl, 2.0 equiv) and 4-nitrophenylchloroformate (25 mg, 2.0 equiv) were added again. This was repeated after 48 hours stirring at 6° C. After another 48 hours the solution was evaporated in vacuo and the residual product was dissolved in chloroform. The organic layer was washed with 10% citric acid, brine and water, dried over sodium sulfate ($Na_2SO_4$) and evaporated yielding a yellow solid. The crude product was purified by means of column chromatography ($SiO_2$—$CHCl_3$/MeOH; 15/1) to give the desired product 35 quantitatively. $^1$H-NMR (300 Mz, $CDCl_3$/$CD_3OD$): δ 1.12–1.89 (m, 9H, $CH_3$-Ala and 3 $CH_2$-Lys), 3.04 (m, 1H, benzylic), 3.14 (m, 2H, N—$CH_2$-Lys), 3.27 (bd, 1H, benzylic), 4.09 (m, 1H, Hα), 4.28 (m, 1H, Hα), 4.34–4.68 (m, 5H, Hα and Aloc), 5.02–5.40 (m, 4H, Aloc), 5.14 (s, 2H, benzylic-spacer), 5.21 (s, 2H, benzylic-spacer), 5.31 (s, 2H, benzylic spacer), 5.72 (m, 1H, Aloc), 5.90 (m, 1H, Aloc), 7.10–7.52 (m, 17H, aromatic), 7.63 (d, 2H, J=8.3 Hz, aromatic), 8.27 (d, 2H, J=9.1 Hz, aromatic-PNP) ppm; MS (FAB) me 1102 (M+H)$^+$, 1124 (M+Na)$^+$.

Example 28

Synthesis of Aloc-D-Ala-Phe-Lys(Aloc)-PABC-PABC-PABC-DOX 36.

The 4-nitrophenyl carbonate 35 (69 mg, 0.063 mmol) and doxorubicin-HCl (40 mg, 1.1 equiv) in N-methylpyrrolidinone were treated at room temperature with triethylamine (9.7 μl, 1.1 equiv). The reaction mixture was stirred in the dark for 24 hours and the reaction mixture was diluted with 10% 2-propanol/ethyl acetate. The organic layer was washed with water and brine, and was dried over sodium sulfate ($Na_2SO_4$). After evaporation of the solvents the crude product was purified by means of column chromatography (SiO$_2$—CHCl$_3$/MeOH 9/1) followed by circular chromatography using a chromatotron supplied with a 2 mm silica plate (CHCl$_3$/MeOH; 9/1), to yield 65 mg (71%) of the protected prodrug 36. $^1$H-NMR (300 MHz, CDCl$_3$/CD$_3$OD): δ 1.10–1.80 (m, 14H, sugar CH$_3$, CH$_3$-Ala, 3 CH$_2$-Lys and 2'), 2.14 (dd, 1H, 8), 2.36 (bd, 1H, 8), 3.18 (bd, 1H, 10), 2.82–3.41 (m, 6H, benzylic Phe and N—CH$_2$-Lys and 10), 3.37 (s, 1H, 4'), 3.60 (bs, 1H, 3'), 4.02 (m, 1H, Hα), α), 4.07 (s, 3H, OMe) 4.29 (dd, 1H, 5'), 4.37–4.68 (m, 5H, Hα and 4 Aloc), 4.76 (s, 2H, 14), 4.95 (bs, 2H, benzylic spacer), 5.10 (s, 2H, benzylic spacer), 5.14 (s, 2H, benzylic spacer), 5.02–5.35 (m, 4H, Aloc), 5.27 (bs, 1H, 1'), 5.47 (bs, 1H, 7), 5.70 (m, 1H, Aloc), 5.89 (m, 1H, Aloc), 7.09–7.50 (m, 16H, 5 Phe and 10 spacers and 3), 7.64 (d, 2H, J=8.4 Hz, 2H aromatic spacer), 7.79 (t, 1H, J=8.1 Hz, 2), 8.06 (d, 1H, J=7.5 Hz, 1) ppm; MS (FAB) m/e 1506 (M+H)$^+$, 1528 (M+Na)$^+$.

Example 29

Synthesis of D-Ala-Phe-Lys-PABC-PABC-PABC-DOX (.2HCl) 37.

To a solution of 40 mg protected prodrug 36 (0.027 mmol) in dry tetrahydrofuran/dichloromethane under an argon atmosphere were added morpholine (24 μl, 10 equiv) and a catalytic amount of Pd(PPh$_3$)$_4$. The reaction mixture was stirred for 1 hour in the dark. The red precipitate was collected by means of centrifugation and washed several times with ethyl acetate. Water and dioxane were added and the mixture was acidified using 4.4 ml of 0.125 mM hydrochloric acid. After freeze drying 26 mg (70%) of doxorubicin prodrug 37 was obtained. $^1$H-NMR (300 MHz, CDCl$_3$/CD$_3$OD): δ 1.19 (d, 3H, J=6.9 Hz, sugar CH$_3$), 1.27 (d, 3H, J=6.6 Hz, CH$_3$-Ala), 1.25–2.00 (m, 8H, 3 CH$_2$-Lys and 2'), 2.18 (dd, 1H, 8), 2.33 (br d, 1H, J=16.1 Hz, 8), 2.89–3.38 (m, 6H, N—CH$_2$-Lys and 10 and Bn Phe), 3.60 (s, 1H, 4'), 3.72 (m, 1H, 3'), 4.08 (s, 3H, OMe), 4.18 (m, 1H, Hα), 4.53 (dd, 1H, 5') 4.66 (m, 1H, Hα), 4.77 (s, 2H, 14), 4.96 (s, 2H, Bn spacer), 5.11 (s, 2H, bn spacer), 5.17 (s, 2H, Bn spacer), 5.27 (br s, 1H 1'), 5.48 (br s, 1H, 7), 7.05–7.35 (m, 16H, aromatic spacer and 3), 7.52 (d, 2H, J=8.5 Hz, aromatic spacer), 7.84 (t, 1H, 2), 8.01 (d, 1H, J=7.7 Hz, 1) ppm.

Example 30

Synthesis of 2'-[4-nitrophenyl carbonate]-paclitaxel 38.

To a solution of 194 mg (0.227 mmol) paclitaxel in dry dichloromethane under an Argon atmosphere was added pyridine (4 drops). At –50° C., 275 mg (6.0 eq.) 4-nitrophenyl chloroformate dissolved in dry dichloromethane was added. The reaction mixture was stirred at –50° C. and after 4 hours 4-nitrophenyl chloroformate (4.2 eq.) was added. After 1 hour the mixture was diluted with dichloromethane and washed with 0.5 N potassium bisulfate and brine and dried over anhydrous sodium sulphate. After evaporation of the solvents the residual yellow film was purified by means of column chromatography (SiO$_2$—EtOAc/Hex 1/1), to yield 133 mg of activated paclitaxel 38 (78%, 73% conversion). M.P. 161° C.; $^1$H-NMR (300 MHz, CDCl$_3$): δ 1.14 (s, 3H, 17), 1.25 (s, 3H, 16), 1.68 (s, 3H, 19), 1.92 (s, 3H, 18), 2.22 (s, 3H, 10-OAc), 2.49 (s, 3H, 4-OAc), 2.55 (m, 1H, 6a), 3.82 (d, 1H, 3), 4.21 (d, 1H, 20b), 4.32 (d, 1H, 20a), 4.42 (m, 1H, 7), 4.96 (bd, 1H, 5), 5.53 (d, 1H, 2'), 5.69 (d, 1H, 2), 6.09 (q, 1H, 3'), 6.29 (s, 1H, 10), 6.34 (m, 1H, 13), 6.90 (d, 1H, N—H), 7.20–7.65 (m, 13H, aromatic), 7.75 (d, 2H, aromatic), 8.15 (d, 2H, aromatic), 8.25 (d, 2H, nitrophenyl) ppm; MS (FAB) m/e 1020 (M+H)$^+$, 1042 (M+Na)$^+$; C$_{54}$H$_{54}$N$_2$O$_{19}$ (.1½H$_2$O) calculated C, 62.00%; N, 2.68%; measured C, 61.89%; H, 5.52%; N, 2.64%.

Example 31

Synthesis of 2'-[H-D-Ala-Phe Lys-PABC-N(Me)-(CH$_2$)$_2$—N(Me)CO]-paclitaxel (.2HCl) 43.

Step a: Synthesis of N(Me)—(CH$_2$)$_2$—N(Me)—Z 39 (Z=benzyloxycarbonyl).

To a solution of 1.21 g (13.7 mmol) N,N'-dimethyl ethylenediamine in dry dichloromethane under an Argon atmosphere at room temperature was added dropwise a solution of Z-ONSu (338 mg, 1.36 mmol) in dry dichloromethane. After stirring for 120 minutes the solution was concentrated in vacuo. The residual product was dissolved in ethyl acetate and the organic layer was washed with brine. The organic solvent was dried over anhydrous sodium sulfate and evaporated to dryness. The oily product was purified by means of column chromatography (SiO$_2$—CHCl$_3$/MeOH 1/1) to obtain 249 mg (83%) of the product 39 as an oil. $^1$H-NMR (300 MHz, CDCl$_3$): δ 2.42 (bd, 3H, $^3$J=13.9 Hz, CH$_3$—NH—CH$_2$), 2.73 (m, 2H, CH$_3$—NH—CH$_2$), 2.95 (s, 3H, CH$_3$—N), 3.41 (bs, 2H, CH$_2$—N), 5.13 (s, 2H, CH$_2$—Z), 7.25–7.40 (m, 5H, aromatic) ppm.

Step b: Synthesis of 2'-[Z—N(Me)—(CH$_2$)$_2$—N(Me)CO]-paclitaxel 40.

To a solution of 114 mg (112 μmol) 2'-activated paclitaxel 38 and 25 mg Z-protected N,N'-dimethyl ethylenediamine 39 in dry dichloromethane under an Argon atmosphere at –50° C. was added triethyl amine (20.0 μl, 144 μmol). The solution was stirred 7 hours at –40° C., subsequently allowed to heat up to room temperature and then stirring was continued overnight at room temperature. The solution was diluted with dichloromethane and washed with saturated sodium bicarbonate, brine and 0.5 N potassium bisulfate. The organic layer was dried over anhydrous sodium sulfate and concentrated in vacuo to obtain a yellow film. The product was purified by column chromatography (SiO$_2$—EtOAc/Hex 2/1) to obtain 113 mg (92%) of the desired product 40. M.P. 130–131° C.; $^1$H-NMR (300 MHz, CDCl$_3$): δ 1.12 (s, 3H, 17), 1.21 (s, 3H, 16), 1.70 (s, 3H, 19), 2.00 (s, 3H, 18), 2.26 (s, 3H, 10-OAc), 2.60 (s, 3H, 4-OAc), 2.90 (s, 3H, CH$_3$-spacer), 2.94 (s, 3H, CH$_3$-spacer), 2.97 (m, 1H, CH$_2$-spacer), 3.06 (m, 1H, CH$_2$-spacer), 3.54 (m, 1H, CH$_2$-spacer), 3.78 (m, 1H, CH$_2$-spacer), 3.84 (d, 1H, $^3$J=7.2 Hz, 3), 4.23 (d, 1H, $^2$J=8.4 Hz, 20b), 4.32 (d, 1H, $^2$J=8.4 Hz, 20a), 4.47 (m, 1H, 7), 4.69 (d, 1H, $^2$J=12.4 Hz, benzylic), 4.85 (d, 1H, $^2$J=12.4 Hz, benzylic), 5.01 (m, 1H, 5), 5.47 (d, 1H, $^3$J=2.9 Hz, 2'), 5.68 (d, 1H, $_3$J=7.0 Hz, 2), 6.19 (dd, 1H, $^3$J=9.8 Hz, $^3$J=2.9 Hz, 3'), 6.28 (s, 1H, 10), 6.33 (m, 1H, 13), 6.94–7.70 (m, 16H, aromatic), 7.83 (d, 2H, $^3$J=7.3 Hz, aromatic), 8.16 (d, 2H, $^3$J=7.1 Hz, aromatic), 8.57 (d, 1H, $^3$J=9.8 Hz, NH) ppm; MS (FAB) m/e 1102 (M+H)$^+$, 1124 (M+Na)$^+$; C$_{60}$H$_{67}$N$_3$O$_{17}$ (.H$_2$O) calculated C, 64.33%; H, 6.21%; N, 3.73%; measured C, 64.65%; H, 6.11%; N, 3.76%.

Step c: Synthesis of 2'-[N(Me)—(CH$_2$)$_2$—N(Me)CO]-paclitaxel (.7AcOH) 41.

To a solution of 61.8 mg (56.1 μmol) of 40 in 5% acetic acid/methanol was added a catalytic amount of 10% Pd—C. The mixture was stirred for 1 hour under a H$_2$ atmosphere. The Pd—C was removed by means of centrifugation, methanol was evaporated in vacuo, and ethyl acetate was added.

The organic layer was extracted with water. The water layer was freeze dried yielding 78.0 mg (100%) of the desired product 41.

Step d: Synthesis of 2'-[Aloc-D-Ala-Phe-Lys(Aloc)-PABC-N(Me)—(CH$_2$)$_2$—N(Me)CO]-paclitaxel 42.

To a solution of 152 mg (95.8 µmol) of paclitaxel-spacer compound 41 and 80.7 mg (101 µmol) of carbonate 16 in dry tetrahydrofuran under an Argon atmosphere was added triethyl amine (200 µl, 1.44 mmol). After 24 hours the solution was concentrated to dryness and the residual product was dissolved in dichloromethane and washed with saturated sodium bicarbonate and brine. The organic layer was dried over anhydrous sodium sulfate and evaporated in vacuo. The crude product was subjected to column chromatography (SiO$_2$—EtOAc/Hex/MeOH 5/5/1) to obtain 113 mg (72%) of the desired protected prodrug 42. M.P. 127–128° C.; $^1$H-NMR (300 Mz, CDCl$_3$): δ 1.13 (s, 3H, 17), 1.22 (s, 3H, 16), 1.27 (d, 3H, $^3$J=5.6 Hz, CH$_3$-Ala), 1.04–2.00 (m, 6H, CH$_2$-Lys), 1.69 (s, 3H, 19), 2.00 (s, 3H, 18), 2.22 (s, 3H, 10-OAc), 2.59 (s, 3H, 4-OAc), 2.90 (s, 3H, CH$_3$-spacer), 2.91 (s, 3H, CH$_3$-spacer), 2.76–3.46 (m, 6H, CH$_2$-spacer, benzylic and N—CH$_2$-Lys), 3.54. (m, 1H, CH$_2$-spacer), 3.74 (m, 1H, CH$_2$-spacer), 3.84 (d, 1H, $^3$J=7.0 Hz, 3), 4.00–5.00 (m, 3H, 3 Hα), 4.23 (d, 1H, $^2$J=8.4 H 20b), 4.32 (d, 1H, $^2$J=8.4 Hz, 20a), 4.48 (m, 1H, 7), 4.62 (d, 1H, $^2$J=12.3 Hz, benzylic), 4.83 (d, 1H, $^2$J=12.4 Hz, benzylic), 4.30–4.73 (m, 4H, Aloc), 4.93–5.39 (m, 5H, Aloc and 5), 5.48 (d, 1H, $^3$J=2.9 Hz, 2'), 5.69 (d, 1H, $^3$J=7.0 Hz, 2), 5.54–5.78 (m, 1H, Aloc), 5.88 (m, 1H, Aloc), 6.18 (bd, 1H, 3'), 6.30 (s, 1H, 10), 6.33 (m, 1H, 13), 7.05–7.78 (m, 20H, aromatic), 7.82 (d, 2H, $^3$J=7.4 Hz, aromatic), 8.16 (d, 2H, $^3$J=7.2 Hz, aromatic) ppm; MS (FAB) m/e 1653 (M+Na)$^+$; C$_{86}$H$_{102}$N$_8$O$_{24}$ calculated C, 62.61%; H, 6.35%; N 6.79%; measured C, 62.40%; H 6.31%; N, 6.36%.

Step e: Synthesis of 2'-[H-D-Ala-Phe-Lys-PABC-N(Me)—(CH$_2$)$_2$—N(Me)CO]-paclitaxel (.2HCl) 43.

To a solution of 83.0 mg (50.9 µmol) protected prodrug 42 in dry tetrahydrofuran under an Argon atmosphere was added glacial acetic acid (12 µl, 4.0 eq.) together with tributyltinhydride (41 µl, 3.0 eq) and a catalytic amount of Pd(PPh$_3$)$_4$. After 30 minutes the product was precipitated by addition of diethyl ether. The white precipitate was collected by means of centrifugation and washed several times with diethyl ether. Tert-butanol was added and evaporated again to remove an excess of HCl and the resulting product was dissolved in water/dioxane and freeze dried yielding 56 mg (70%) of prodrug 43. M.P. 142° C.; $^1$H-NMR (300 MHz, CDCl$_3$): δ 1.13 (s, 3H, 17), 1.21 (s, 3H, 16), 1.26 (d, 3H, $^3$J=6.6 Hz, CH$_3$—Ala), 1.05–2.00 (m, 6H CH$_2$-Lys), 1.69 (s, 3H, 19), 2.00 (s, 3H, 18), 2.22 (s, 3H, 10-OAc), 2.58 (s, 3H, 4-OAc), 2.89 (s, 3H, CH$_3$-spacer), 2.91 (s, 3H, CH$_3$-spacer), 2.67–3.64 (m, 3H, Ch$_2$-spacer), 2.95 (m, 1H, benzylic), 3.07 (m, 2H, N—CH$_2$-Lys), 3.15 (m, 1H, benzylic), 3.78 (m, 1H, CH$_2$-spacer), 3.83 (d, 1H, $^3$J=7.1 Hz, 3), 4.10–5.05(m, 2H, 2 Hα), 4.22 (d, 1H, $^2$J=8.4 Hz, 20b), 4.32 (d, 1H, $^2$J=8.4 Hz, 20a), 4.46 (m, 1H, 7), 4.60 (m, 1H, Hα), 4.65 (d, 1H, $^2$J=12.3 Hz, benzylic-spacer), 4.80 (d, 1H, $^2$J=12.4 Hz, benzylic-spacer), 4.99 (bd, 5H, $^3$J=7.4 Hz, 5), 5.47 (d, 1H, $^3$J=2.9 Hz, 2'), 5.68 (d, 1H, $^3$J=6.9 Hz, 2), 6.17 (bd, 1H, $^3$J=2.9 Hz, $^3$J=9.6 Hz, 3'), 6.30 (s, 1H, 10), 6.31 (m, 1H, 13), 7.05–7.70 (m, 20H, aromatic), 7.82 (d, 2H, $^3$J=7.5 Hz, aromatic), 8.16 (d, 2H, $^3$J=7.2 Hz, aromatic), 8.54 (d, 1H, $^3$J=9.6 Hz, NH-paclitaxel) ppm; MS (FAB) m/e 1463 (M+H)$^+$, 1485 (M+Na)$^+$; C$_{85}$H$_{97}$N$_7$O$_{22}$ (.3AcOH) calculated C 61.04%; H, 6.50%; N, 6.71%; measured C, 60.91%; H, 6.45%; N, 7.10%.

Example 32

Synthesis of 2'-O-[D-Ala-Phe-Lys-PABC-PABC-N(Me): CH—N(Me)CO]paclitaxel.2HCl.

Step a: Synthesis of 2'-O-[Aloc-D-Ala-Phe-Lys(Aloc)-PABC-PABC-N(Me)—(CH$_2$)$_2$—N(Me)CO]paclitaxel.

To a solution of paclitaxel-spacer conjugate 41 (50 mg, 48.6 µmol) and peptide-spacer conjugate 18 (46.3 mg, 48.6 µmol) in THF (3 mL) was added triethylamine (101 µL, 0.730 mmol). The reaction mixture was stirred at room temperature for 15 h and then concentrated under reduced pressure. The residue was dissolved in dichloromethane, and the solution was washed with a saturated aqueous NaHCO$_3$ solution and brine, dried over Na$_2$SO$_4$, filtered, and concentrated under reduced pressure. Column chromatography (SiO$_2$—EtOAc/Hex/MeOH 5/4/1) gave 44 (58.2 mg, 32.7 µmol, 67%).

$^1$H-NMR (300 MHz, CDCl$_3$): δ 1.12 (s, 3H, 17), 1.21 (s, 3H, 16), 1.26 (d, 3H, J=6.6 Hz, CH$_3$ of Ala), 1.05–2.00 (m, 6H, 3×CH$_2$ of Lys), 1.69 (s, 3H, 19), 1.99 (s, 3H, 18), 2.22 (s, 3H, 10-OAc), 2.58 (s, 3H, 4-OAc), 2.90 (s, 3H, N—CH$_3$), 2.91 (s, 3H, N—CH$_3$), 2.80–3.85 (m, 9H, N—CH$_2$—CH$_2$—N and CH$_2$ of Phe and N—CH$_2$ of Lys and 3), 4.00–5.38 (m, 19H, 3×Hα and 20 and 7 and 2×CH$_2$ of spacer and 5 and 2×CH$_2$=CH—CH$_2$), 5.46 (d, 1H, J=2.7 Hz, 2'), 5.60 (m, 1H, CH$_2$=CH—CH$_2$), 5.69 (d, 1H, J=6.9 Hz, 2), 5.89 (m, 1H, CH$_2$=CH—CH$_2$), 6.16 (dd, 1H, J=9.3 Hz, J=2.4 Hz, 3'), 6.30 (s, 1H, 10), 6.31 (m, 1H, 13), 7.09–7.81 (m, 26H, aromatic), 8.16 (d, 2H, J=7.2 Hz, aromatic) ppm.

Step b: Synthesis of 2'-O-[D-Ala-Phe-Lys-PABC-PABC-N(Me)-(CH$_2$)$_2$—N(Me)CO]paclitaxel.2HCl.

To a solution of protected prodrug 44 (50.0 mg, 28.1 µmol) in dry THF (3 mL) were added tributyltin hydride (22.7 µL), Pd(PPh$_3$)$_4$ (6.5 mg, 5.6 µmol), and acetic acid (6.5 µL, 0.112 mmol). After 30 min, the reaction mixture was slowly added to cold diethyl ether. The white precipitate was collected by means of centrifugation and washed two times with diethyl ether. The residue was suspended in ethyl acetate and a 0.5 M HCl solution in ethyl acetate (0.5 mL) was added under vigorous stirring. The white precipitate was collected by means of centrifugation and washed two times with ethyl acetate. tert-Butyl alcohol was added to the residue and subsequently evaporated to remove excess HCl. The residue was dissolved in water en freeze-dried, giving 45 (32.0 mg, 19.0 µmol, 68%).

$^1$H-NMR (300 MHz, CDCl$_3$/CD$_3$OD): δ 1.17 (s, 3H, 17), 1.19(s, 3H, 16), 1.26 (d, 3H, J=6.9 Hz, CH$_3$ of Ala), 1.20–2.00 (m, 6H, 3×CH$_2$ of Lys), 1.70 (s, 3H, 19), 2.02 (s, 3H, 18 ), 2.21 (s, 3H, 10-OAc), 2.55 (s, 3H, 4-OAc), 2.80–2.99 (m, 4H, CH$_2$ of Phe and N—CH$_2$ of Lys), 2.93 (s, 6H, 2×N—CH$_3$), 3.10–3.87 (m, 4H, N—CH$_2$—CH$_2$—N), 3.86 (d, 1H, J=6.9 Hz, 3), 4.06 (q, 1H, J=7.0 Hz, Hα), 4.26–4.76 & 5.02 (m 8H, 2×Hα and 20 and 7 and CH$_2$ of spacer and 5), 5.16 (s, 2H, CH$_2$ of spacer), 5.45 (d, 1H, J=2.5 Hz, 2'), 5.72 (d, 1H, J=7.1 Hz, 2), 6.10 (m, 1H, 3'), 6.26 (m, 1H, 13), 6.40 (s, 1H, 10), 7.08–7.62 (m, 24H, aromatic), 7.77 (d, 2H, J=7.6 Hz, aromatic), 8.14 (m, 2H, aromatic) ppm.

Example 33

Synthesis of 2'-O-[D-Ala-Phe-Lys-PACC-N(Me)—(CH$_2$)$_2$—N(Me)CO]paclitaxel-2HCl 49.

Step a: Preparation of NZ-D-Ala-Phe-Lys(NZ)—OH 9c.

To a solution of tripeptide 8 (506 mg, 1.39 mmol) in dichloromethane (10 mL) were added trimethylsilyl chloride (0.568 mL, 4.44 mmol) and DIPEA (0.509 mL, 2.92 mmol).

The reaction mixture was stirred at reflux temperature for 1.5 h. Then, the reaction mixture was cooled down to 0° C., after which DIPEA (776 μL, 4.44 mmol) and para-nitrobenzyl chloroformate (NZ—Cl) (629 mg, 2.92 mmol) were added. The reaction mixture was stirred at room temperature for 5 h and then concentrated under reduced pressure. The residue was partitioned between ethyl acetate and acetate buffer (pH=5). The organic layer was washed with more acetate buffer, water, and brine, dried over $Na_2SO_4$, filtered, and concentrated under reduced pressure. Column chromatography ($SiO_2$—$CH_2Cl_2$/MeOH/AcOH 90/7/5) gave 9c (620 mg, 0.858 mmol, 61%).

$^1$H-NMR (300 MHz, $CDCl_3$/$CD_3OD$): δ 1.18 (d, 3H, J=7.1 Hz, $CH_3$ of Ala), 1.36–1.97 (m, 6H, 3×$CH_2$ of Lys), 2.94 (dd, 1H, $CH_2$ of Phe), 3.12–3.23 (m, 3H, $CH_2$ of Phe and N—$CH_2$ of Lys), 4.12 (m, 1H, Hα), 4.42 (m, 1H, Hα), 4.63 (m, 1H, Hα), 5.17 (m, 4H, $CH_2$ of NZ), 7.17–7.25 (m, 5H, aromatic), 7.51 (d, 4H, J=8.2 Hz, aromatic), 8.19 (d, 4H, J=8.0 Hz, aromatic) ppm.

Step b: Preparation of NZ-D-Ala-Phe-Lys(Z)-PACA 46.

To a solution of protected tripeptide 9c (300 mg, 0.415 mmol) in THF (10 mL) were added at −40° C. N-methylmorpholine (50.2 μL, 0.457 mmol) and isobutyl chloroformate (62.4 mg, 0.457 mmol). The reaction mixture was stirred at −30° C. for 3 h. Then, spacer 10 (77.3 mg, 0.498 mmol) and N-methylmorpholine (55.0 μL, 0.498 mmol) in THF (5 nL) were added. The reaction mixture was stirred for 15 h, the reaction temperature slowly being raised to room temperature. The reaction mixture was concentrated under reduced pressure and the residue was dissolved in dichloromethane. The solution was washed with a saturated aqueous $NaHCO_3$ solution, a 0.5 M aqueous $KHSO_4$ solution, and brine, dried over $Na_2SO_4$, filtered, and concentrated under reduced pressure. Column chromatography ($SiO_2$—$CHCl_3$/MeOH 93/7) gave 46 (267 mg, 0.313 mmol, 75%).

$^1$H-NMR (300 MHz, $CDCl_3$/$CD_3OD$): δ 1.22 (d, 3H, J=7.2 Hz, $CH_3$ of Ala), 1.40–2.04 (m, 6H, 3×$CH_2$ of Lys), 2.96 (dd, 1H, J=9.9 Hz, J=14.4 Hz, $CH_2$ of Phe), 3.15 (m, 2H, N—$CH_2$ of Lys), 3.30 (dd, 1H, J=14.4 Hz, J=4.2 Hz, $CH_2$ of Phe), 4.08 (m, 1H, Hα), 4.23 (dd, 2H, J=1.1 Hz, J=5.6 Hz, $CH_2$ of spacer), 4.46 (m, 1H, Hα), 4.56 (m, 1H, Hα), 4.90 (d, 1H, J=13.8 Hz, $CH_2$ of NZ), 4.99 (d, 1H, J=13.8 Hz, $CH_2$ of NZ), 5.17 (s, 2H, $CH_2$ of NZ), 6.26 (dt, 1H, J=5.7 Hz, J=15.9 Hz, CH=C$\underline{H}$—$CH_2$), 6.52 (d, 1H, J=15.9 Hz, C$\underline{H}$=CH—$CH_2$), 7.22–7.32 (m, 9H, aromatic), 7.53 (d, 2H, J=8.6 Hz, aromatic), 7.61 (d, 2H, J=8.6 Hz, aromatic), 8.04 (d, 2H, J=8.6 Hz, aromatic), 8.19 (d, 2H, J=8.6 Hz, aromatic) ppm.

Step c: Preparation of NZ-D-Ala-Phe-Lys(NZ)-PACC-PNP 47.

To a solution of peptide-spacer 46 (244 mg, 0.286 mmol) in THF (15 mL) were added DIPEA (0.216 mL, 1.24 mmol), para-nitrophenyl chloroformate (187 mg, 0.927 mmol), and pyridine (6.3 μL, 77.2 μmol). The reaction mixture was stirred for 48 h and then diluted with ethyl acetate (50 mL). The solution was washed with a 10% aqueous citric acid solution, water, and brine, dried over $Na_2SO_4$, filtered, and concentrated under reduced pressure. Column chromatography ($SiO_2$—$CHCl_3$/MeOH 95/5) gave 47 (291 mg, 0.286 mmol, 100% A).

$^1$H-NMR (300 MHz, $CDCl_3$/$CD_3OD$/DMSO-$_6$): δ 1.23 (d, 3H, J=7.1 Hz, $CH_3$ of Ala), 1.38–2.03 (m, 6H, 3×$CH_2$ of Lys), 2.97 (dd, 1H, J=9.9 Hz, J=14.0 Hz, $CH_2$ of Phe), 3.14 (m, 2H, N—$CH_2$ of Lys), 3.28 (dd, 1H, $CH_2$ of Phe), 4.10 (m, 1H, Hα), 4.47 (m, 1H, Hα), 4.54 (m, 1H, Hα), 4.87–5.00 (m, 4H, $CH_2$ of spacer and $CH_2$ of NZ), 5.17 (s, 2H, $CH_2$ of NZ), 6.27 (dt, 1H, J=6.8 Hz, J=15.4 Hz, CH=C$\underline{H}$—$CH_2$), 6.70 (d, 1H, J=15.4 Hz, C$\underline{H}$=CH—$CH_2$), 7.22–7.33 (m, 9H, aromatic), 7.47 (d, 2H, J=9.2 Hz, aromatic), 7.53 (d, 2H, J=8.6 Hz, aromatic), 7.67 (d, 2H, J=8.6 Hz, aromatic), 8.04 (d, 2H, J=8.6 Hz, aromatic), 8.18 (d, 2H, J=8.6 Hz, aromatic), 8.30 (d, 2H, J=9.2 Hz, aromatic) ppm.

Step d: Preparation of 2'-O-[NZ-D-Ala-Phe-Lys(NZ)-PACC-N(Me)—$(CH_2)_2$—N(Me)CO]paclitaxel 48.

To a solution of paclitaxel-spacer conjugate 41 (50 mg, 48.6 μmol) and peptide-spacer conjugate 47 (54.5 mg, 53.5 μmol) in THF (3 mL) was added triethylamine (101 μL, 0.730 mmol). The reaction mixture was stirred at room temperature for 15 h and then concentrated under reduced pressured. The residue was dissolved in dichloromethane, and the solution was washed with a saturated aqueous $NaHCO_3$ solution and brine, dried over $Na_2SO_4$, filtered, and concentrated under reduced pressure. Column chromatography ($SiO_2$—EtOAc/Hex/MeOH 5/4/1) gave 48 (65.7 mg, 35.6 μmol, 73%).

$^1$H-NMR (300 MHz, $CDCl_3$): δ 1.12 (s, 3H, 17), 1.21 (s, 3H, 16), 1.30 (d, 3H, J=7.0 Hz, $CH_3$ of Ala), 1.20–2.10 (m, 6H, 3×$CH_2$ of Lys), 1.68 (s, 3H, 19), 2.00 (s, 3H, 18), 2.22 (s, 3H, 10-OAc), 2.58 (s, 3H, 4-OAc), 2.91 (s, 3H, N—$CH_3$), 2.95 (s, 3H, N—$CH_3$), 2.90–3.90 (m, 8H, N—$CH_2$—$CH_2$—N and $CH_2$ of Phe and N—$CH_2$ of Lys), 3.83 (d, 1H, J=6.6 Hz, 3), 4.10–5.00 (m, 11H, 3×Hα and 20 and 5 and 7 and CH=CH—$C\underline{H}_2$ and $CH_2$ of NZ), 5.16 (s, 2H, $CH_2$ of NZ), 5.46 (d, 1H, J=3.3 Hz, 2'), 5.68 (d, 1H, J=7.5 Hz, 2), 6.01–6.17 (m, 2H, 3' and CH=C$\underline{H}$—$CH_2$), 6.31 (s, 1H, 10), 6.32 (m, 1H, 13), 6.40 (d, 1H, J=15.9 Hz, C$\underline{H}$=CH—$CH_2$), 7.19–7.70 (m, 24H, aromatic), 7.83 (d, 2H, J=7.2 Hz, aromatic), 8.01 (d, 2H, J=8.7 Hz, aromatic), 8.15–8.19 (m, 4H, aromatic) ppm.

Step e: Preparation of 2'-O-[D-Ala-Phe-Lys-PACC-N(Me)—$(CH_2)_2$—N(Me)CO]paclitaxel.2HOAc 49.

To a solution of protected prodrug 48 (50.0 mg, 27.1 μmol) in methanol (5 mL) was added acetic acid (1.5 mL) and zinc (88.5 mg, 1.35 mmol). The resultant suspension was stirred at room temperature for 24 h. Then, the reaction mixture was filtered over HYFLO. Water was added and methanol was evaporated under reduced pressure. The resultant solution was freeze-dried to obtain a slightly yellow solid, which was dissolved in a mixture of dichloromethane and methanol (2 mL, 1:1 v/v). This solution was added to cold diisopropyl ether. The white precipitate was collected by means of centrifugation and washed two times with diisopropyl ether, which afforded prodrug 49 (27.8 mg, 17.3 μmol, 64%).

Example 34

Stability of Both Double Spacer Containing Paclitaxel Prodrugs 22 and 43.

The prodrugs were incubated at concentrations of 150 μM in 0.1 M Tris/HCl buffer (pH 7.3) for 3 days and showed no formation of degradation products (TTC, $RP_{18}$; $CH_3CN$/$H_2O$/AcOH 19/19/2).

Stability of the Double Spacer Containing Doxorubicin Prodrug 20.

The prodrug was incubated at a concentration of 100–270 μM in 0.1 M Tris/HCl buffer (pH 7.3) for 90 hours and showed no formation of degradation products (TLC, $RP_{18}$; $CH_3CN$/$H_2O$/AcOH 19/19/2).

Example 35

Enzymatic Hydrolysis of the Double Spacer Containing Prodrugs by Plasmin.

Hydrolysis of the doxorubicin prodrugs was investigated by incubation at a prodrug concentration of 100 μM in 0.1 M Tris/hydrochloric acid buffer (pH 7.3) in the presence of 50 or 20 μg/mL human plasmin (Fluka). Analysis was carried out with the following HPLC system using a Chrompack Microsphere-C18 column (3 μm, 2×100×4.6 1 mm). Elution of the analytical column was performed using 7:3 methanol/50 mM $Et_3N$-formate buffer (pH 3.0). Detection was performed using an UV-detector ($\lambda$=500 nm).

|  | [prodrug] (μM) | [plasmin] (μg/mL) | $T_{1/2}$ activation (min) |
|---|---|---|---|
| Prodrug 50 | 100 | 50 | 19 |
| Prodrug 50 | 200 | 20 | >75 |
| Prodrug 20 | 200 | 20 | 12 |

Hydrolysis of the paclitaxel prodrugs was investigated by incubation at a prodrug concentration of 200 μM in 0.1 M Tris/hydrochloric acid buffer (pH 7.3) in the presence of 100 μg/mL human plasmin (Fluka). All double spacer containing paclitaxel prodrugs were converted to yield the corresponding parent drug. Capillary electrophoresis was carried out with a CE Ext. Light Path Capillary (80.5 cm, 50 μm), with 1:1 methanol/0.05 M sodium phosphate buffer (pH 7.0) as eluent Detection was performed at 200 and 254 nm.

|  | [prodrug] (μM) | [plasmin] (μg/mL) | $T_{1/2}$ activation (min) | $T_{1/2}$ cyclisation (min) |
|---|---|---|---|---|
| Prodrug 51 | 200 | 100 | 42 |  |
| Prodrug 43 | 200 | 100 | 4 | 47 |
| Prodrug 22 | 200 | 100 | 7.5 |  |

Example 36

Cytotoxicity.

The anti-proliferative effect of prodrugs and parent drugs was determined in vitro applying seven well-characterised human tumor cell lines and the microculture sulphorhodamine B (SRB) test. The anti-proliferative effects were determined and expressed as $IC_{50}$ values, that are the (pro) drug concentrations that gave 50% inhibition when compared to control cell growth after 5 days of incubation.

TABLE 1

$ID_{50}$ values[a,b] (ng/ml) of prodrugs and parent drugs.

| Cell Line: | MCF-7 | EVSA-T | WIDR | IGROV | M19 | A498 | H226 |
|---|---|---|---|---|---|---|---|
| Prodrug 20 | 242 | 546 | 627 | 896 | 302 | 2303 | 503 |
| Prodrug 43 | 60 | 119 | 117 | 499 | 96 | 681 | 62 |
| Prodrug 22 | 11 | 5 | 5 | 22 | 7 | 25 | 7 |

TABLE 1-continued $ID_{50}$ values[a,b] (ng/ml) of prodrugs and parent drugs.

| Cell Line: | MCF-7 | EVSA-T | WIDR | IGROV | M19 | A498 | H226 |
|---|---|---|---|---|---|---|---|
| Paclitaxel | <3 | <3 | <3 | 10 | <3 | <3 | <3 |
| Doxorubicin | 10 | 8 | 11 | 60 | 16 | 90 | 199 |

[a]Drug dose that inhibited cell growth by 50% compared to untreated control cultures.
[b]SRB cell viability test.
Cell lines: MCF-7; breast cancer. EVSA-T; breast cancer. WIDR; colon cancer. IGROV; ovarian cancer. M19; melanoma. A498; renal cancer. H226; non-small cell lung cancer.

The invention claimed is:

1. A compound of the formula:

$$V-(W)_k-(X)_l-A-Z$$

wherein:

V is an enzymatically removable specifier, optionally being removable after prior binding to a receptor;

$(W)_k-(X)_l-A$ is an elongated self-eliminating spacer system;

W and X are each a 1,(4+2n) electronic cascade self-eliminating spacer, being the same or different;

A is either a spacer group of formula $(Y)_m$, wherein Y is a 1,(4+2n) electronic cascade self-eliminating spacer, or a group of formula U being a cyclisation self-elimination spacer;

Z is a therapeutic or diagnostic moiety;

k and l are independently an integer from 0 (included) to 5 (included);

m is an integer from 1 (included) to 5 (included);

n is an integer from 0 (included) to 10 (included), and k+1>0.

2. The compound of claim 1, wherein group U is an ω-amino aminocarbonyl cyclisation spacer, Z is a moiety bearing a hydroxyl group, and Z is bonded to U via the hydroxyl group of Z.

3. The compound of claim 1, wherein the electronic cascade spacers W, X and Y are independently selected from compounds having the formula:

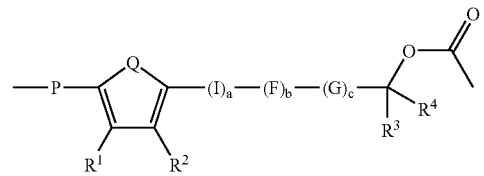

wherein $Q=-R^5C=CR^6-$, S, O, $NR^5$, $-R^5C=N-$, or $-N=CR^5-$ $P=NR^7$, O, S a, b, and c are independently an integer of 0 to 5;

I, F and G are independently selected from compounds having the formula:

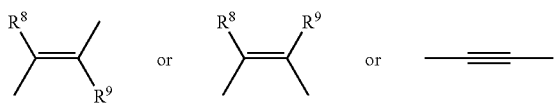

wherein $R^1$, $R^2$, $R^3$, $R^4$, $R^5$, $R^6$, $R^7$, $R^8$, and $R^9$ independently represent H, $C_{1-6}$ alkyl, $C_{3-20}$ heterocyclyl, $C_{5-20}$ aryl, $C_{1-6}$ alkoxy, hydroxy (OH), amino ($NH_2$), mono-substituted amino ($NR_xH$), di-substituted amino ($NR_x^1R_x^2$), nitro ($NO_2$), halogen, $CF_3$, CN, $CONH_2$, $SO_2Me$, CONHMe, cyclic $C_{1-5}$ alkylamino, imidazolyl, $C_{1-6}$ alkylpiperazinyl, morpholino, thiol (SH), thioether ($SR_x$), tetrazole, carboxy (COOH), carboxylate ($COOR_x$), sulphoxy ($S(=O)_2OH$), sulphonate ($S(=O)_2OR_x$), sulphonyl ($S(=O)_2R_x$), sulphixy ($S(=O)OH$), sulphinate ($S(=O)OR_x$), sulphinyl ($S(=O)R_x$), phosphonooxy ($OP(=O)(OH)_2$), and phosphate ($OP(=O)(OR_x)_2$), where $R_x$, $R_x^1$ and $R_x^2$ are independently selected from a $C_{1-6}$ alkyl group, a $C_{3-20}$ heterocyclyl group or a $C_{5-20}$ aryl group, two or more of the substituents $R^1$, $R^2$, $R^3$, $R^4$, $R^5$, $R^6$, $R^7$, $R^8$, or $R^9$ optionally being connected to one another to form one or more aliphatic or aromatic cyclic structures.

4. The compound of claim 2, wherein A is an ω-amino aminocarbonyl cyclisation elimination spacer U and U is a moiety having the formula:

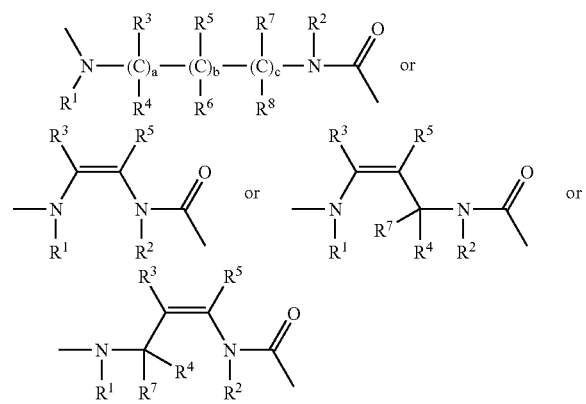

wherein:
a is an integer of 0 or 1; and
b is an integer of 0 or 1; and
c is an integer of 0 or 1; provided that
a+b+c=2 or 3;
and wherein $R^1$ and/or $R^2$ independently represent H, $C_{1-6}$ alkyl, said alkyl being optionally substituted with one or more of the following groups: hydroxy (OH), ether ($OR_x$), amino ($NH_2$), mono-substituted amino ($NR_xH$), di-substituted amino ($NR_x^1R_x^2$), nitro ($NO_2$), halogen, $CF_3$, CN, $CONH_2$, $SO_2Me$, CONHMe, cyclic $C_{1-5}$ alkylamino, imidazolyl, $C_{1-6}$ alkylpiperazinyl, morpholino, thiol (SH), thioether ($SR_x$), tetrazole, carboxy (COOH), carboxylate ($COOR_x$), sulphoxy ($S(=O)_2OH$), sulphonate ($S(=O)_2OR_x$), sulphonyl ($S(=O)_2R_x$), sulphixy ($S(=O)OH$), sulphinate ($S(=O)OR_x$), sulphinyl ($S(=O)R_x$), phosphonooxy ($OP(=O)(OH)_2$), and phosphate ($OP(=O)(OR_x)_2$), where $R_x$, $R_x^1$ and $R_x^2$ are selected from a $C_{1-6}$ alkyl group, a $C_{3-20}$ heterocyclyl group or a $C_{5-20}$ aryl group; and $R^3$, $R^4$, $R^5$, $R^6$, $R^7$, and $R^8$ independently represent H, $C_{1-6}$ alkyl, $C_{3-20}$ heterocyclyl, $C_{5-20}$ aryl, $C_{1-6}$ alkoxy, hydroxy (OH), amino ($NH_2$), mono-substituted amino ($NR_xH$), di-substituted amino ($NR_x^1R_x^2$), nitro ($NO_2$), halogen, $CF_3$, CN, $CONH_2$, $SO_2Me$, CONHMe, cyclic $C_{1-5}$ alkylamino, imidazolyl, $C_{1-6}$ alkylpiperazinyl, morpholino, thiol (SH), thioether ($SR_x$), tetrazole, carboxy (COOH), carboxylate ($COOR_x$), sulphoxy ($S(=O)_2OH$), sulphonate ($S(=O)_2OR_x$), sulphonyl ($S(=O)_2R_x$), sulphixy ($S(=O)OH$), sulphinate ($S(=O)OR_x$), sulphinyl ($S(=O)R_x$), phosphonooxy ($OP(=O)(OH)_2$), and phosphate ($OP(=O)(OR_x)_2$), where $R_x$, $R_x^1$ and $R_x^2$ are selected from a $C_{1-6}$ alkyl group, a $C_{3-20}$ heterocyclyl group or a $C_{5-20}$ aryl group; and wherein $R^1$, $R^2$, $R^3$, $R^4$, $R^5$, $R^6$, $R^7$, and $R^8$ can be a part of one or more aliphatic or aromatic cyclic structures, two or more of the substituents $R^1$, $R^2$, $R^3$, $R^4$, $R^5$, $R^6$, $R^7$, or $R^8$ optionally being connected to one another to form one or more aliphatic or aromatic cyclic structures.

5. The compound of claim 1 wherein A is an electronic cascade spacer having the structural formula:

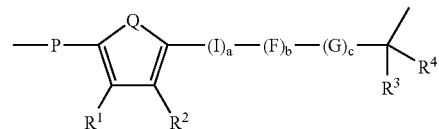

wherein $Q = -R^5C=CR^6-$, S, O, $NR^5$, $-R^5C=N-$, or $-N=CR^5-$ $P = NR^7$, O, S a, b, and c are independently an integer of 0 to 5;

I, F and G are independently selected from compounds having the formula:

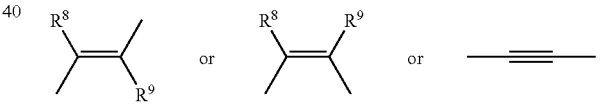

wherein $R^1$, $R^2$, $R^3$, $R^4$, $R^5$, $R^6$, $R^7$, $R^8$, and $R^9$ independently represent H, $C_{1-6}$ alkyl, $C_{3-20}$ heterocyclyl, $C_{5-20}$ aryl, $C_{1-6}$ alkoxy, hydroxy (OH), amino ($NH_2$), mono-substituted amino ($NR_xH$), di-substituted amino ($NR_x^1R_x^2$), nitro ($NO_2$), halogen, $CF_3$, CN, $CONH_2$, $SO_2Me$, CONHMe, cyclic $C_{1-5}$ alkylamino, imidazolyl, $C_{1-6}$ alkylpiperazinyl, morpholino, thiol (SH), thioether ($SR_x$), tetrazole, carboxy (COOH), carboxylate ($COOR_x$), sulphoxy ($S(=O)_2OH$), sulphonate ($S(=O)_2OR$), sulphonyl ($S(=O)_2R_x$), sulphixy ($S(=O)OH$), sulphinate ($S(=O)OR_x$), sulphinyl ($S(=O)R_x$), phosphonooxy ($OP(=O)(OH)_2$), and phosphate ($OP(=O)(OR_x)_2$), where $R_x$, $R_x^1$ and $R_x^2$ are independently selected from a $C_{1-4}$ alkyl group, a $C_{3-20}$ heterocyclyl group or a $C_{5-20}$ aryl group, two or more of the substituents $R^1$, $R^2$, $R^3$, $R^4$, $R^5$, $R^6$, $R^7$, $R^8$, or $R^9$ optionally being connected to one another to form one or more aliphatic or aromatic cyclic structures.

6. The compound of claim 5 wherein Z is a moiety bearing a phenolic hydroxyl group, and Z is bonded to A via the phenolic hydroxyl group of Z.

7. The compound of claim 1 wherein the specifier V contains a substrate that can be cleaved by plasmin.

8. The compound of claim 1 wherein the specifier V contains a substrate that can be cleaved by a cathepsin.

9. The compound of claim 1 wherein the specifier V contains a substrate that can be cleaved by cathepsin B.

10. The compound of claim 1 wherein the specifier V contains a substrate that can be cleaved by β-glucuronidase, prostate-specific antigen (PSA), urokinase-type plasminogen activator (u-PA), or a member of the family of matrix metalloproteinases.

11. The compound of claim 1 to 5 wherein the specifier V contains a nitro-(hetero)aromatic moiety that can be removed by reduction under hypoxic conditions or by reduction by a nitroreductase.

12. The compound of claim 1 wherein the spacer system $(W)_k$—$(X)_l$—A is p-aminobenzyloxycarbonyl-p-aminobenzyloxycarbonyl, p-aminobenzyloxycarbonyl-p-amino-benzyloxycarbonyl-p-aminobenzyloxycarbonyl, p-aminocinnamyloxycarbonyl-p-aminobenzyloxycarbonyl, p-aminobenzyloxycarbonyl-p-aminocinnamyloxycarbonyl, p-aminocinnamyloxycarbonyl-p-aminocinnamyloxycarbonyl, p-aminophenylpentadienyloxycarbonyl-p-aminocinnamyloxycarbonyl p-aminophenylpentadienyloxycarbonyl-p-aminobenzyloxycarbonyl, p-aminophenylpentadienyloxycarbonyl-p-aminophenylpentadienyloxycarbonyl, p-aminobenzyloxycarbonyl(methylamino)ethyl(methylamino)carbonyl, p-aminocinnamyloxycarbonyl(methylamino)ethyl(methylamino)carbonyl, p-aminobenzyloxycarbonyl-p-aminobenzyloxycarbonyl(methylamino)ethyl(methylamino)carbonyl, p-aminocinnamyloxycarbonyl-p-aminobenzyloxycarbonyl(methylamino)ethyl(methylamino)carbonyl, p-aminobenzyloxycarbonyl-p-aminocinnamyloxycarbonyl(methylamino)ethyl(methylamino)carbonyl, p-aminocinnamyloxycarbonyl-p-aminocinnamyloxycaxbonyl(methylamino)ethyl(methylamino)carbonyl, p-aminobenzyloxycarbonyl-p-aminobenzyl, p-aminobenzyloxycarbonyl-p-aminobenzyloxycarbonyl-p-aminobenzyl, p-aminocinnamyloxycarbonyl-p-aminobenzyl, p-aminobenzyloxycarbonyl p-aminocinnamyl, p-aminocinnamyloxycarbonyl-p-aminocinnamyl, p-aminophenylpentadienyloxycarbonyl-p-aminocinnamyl, p-aminophenylpentadienyloxycarbonyl-p-aminobenzyl, or p-aminophenylpentadienyloxycarbonyl-p-aminophenylpentadienyl.

13. The compound of claim 1 wherein the moiety Z is an anticancer agent.

14. The compound of claim 13 wherein the said moiety Z is the amino containing cytotoxic moiety daunorubicin, doxorubicin, N-(5,5-diacetoxypentyl)doxorubicin, an anthracycline, mitomycin C, mitomycin A, 9-amino camptothecin, aminopterin, actinomycin, bleomycin, $N^8$-acetyl spermidine, 1-(2-chloroethyl)-1,2-dimethanesulfonyl hydrazine, tallysomycin, or derivatives thereof,
the hydroxyl containing cytotoxic moiety etoposide, camptothecin, irinotecan, topotecan, 9-amino camptothecin, paclitaxel, docetaxel, esperamycin, 1,8-dihydroxy-bicyclo[7.3.1]trideca-4-ene-2,6-diyne-13-one, anguidine, doxorubicin, morpholine-doxorubicin, N-(5,5-diacetoxypentyl) doxorubicin, vincristine, vinblastine, or derivatives thereof,
the sulfhydryl containing cytotoxic moiety esperamicin, 6-mercaptopurine, or derivatives thereof,
the carboxyl containing cytotoxic moiety methotrexate, camptothecin (ring-opened form of the lactone), butyric acid, retinoic acid, or derivatives thereof.

15. The compound of claim 1 wherein the moiety Z represents the anticancer drug paclitaxel or a paclitaxel derivative that is coupled to the promoiety V—$(W)_k$—$(X)_l$—U— via its 2'-hydroxyl group.

16. The compound of claim 1 wherein the specifier V is a tripeptide.

17. The compound of claim 16 wherein the covalent linkage of said tripeptide specifier moiety to its immediately adjacent moiety is at the C-terminus of said tripeptide specifier moiety.

18. The compound of claim 17 wherein the C-terminal amino acid residue is arginine or lysine, the middle amino acid residue is selected from the group consisting of alanine, valine, leucine, isoleucine, methionine, phenylalanine, cyclohexylglycine, tryptophan and proline, and the N-terminal amino acid residue is a D-amino acid residue, a protected L-amino acid residue, or protected glycine.

19. The compound of claim 1 wherein the specifier V is D-alanylphenylalanyllysine, D-valylleucyllysine, D-alanylleucyllysine, D-valylphenylalanyllysine, D-valyltryptophanyllysine, or D-alanyltryptophanyllysine.

20. The compound of claim 1 wherein the specifier V is an amino-terminal capped peptide covalently linked at its C-terminus to its immediately adjacent moiety.

21. The compound of claim 20 wherein the said amino-terminal capped peptide specifier is benzyloxycarbonylphenylalanyllysine, benzyloxycarbonylvalyllysine, D-phenylalanylphenylalanyllysine, benzyloxycarbonylvalyllysine, tertbutyloxycarbonylphenylalanyllysine, benzyloxycarbonylalanylarginine, benzyloxycarbonylphenylalanyl-N-tosylarginine, 2-aminoethylthiosuccinimidopropionylvalinylcitrulline, 2-aminoethylthiosuccinimidopropionyllysylphenylalanyllysine, acetylphenylalanyllysine, or benzyloxycarbonylphenylalanyl-O-benzoylthreonine.

22. The compound of claim 1 which is N-(D-alanylphenylalanyllysyl-p-aminobenzyloxycarbonyl-p-aminobenzyloxycarbonyl)doxorubicin, N-(D-alanylphenylalanyllysyl-p-aminobenzyloxycarbonyl-p-aminobenzyloxycarbonyl-p-aminobenzyloxycarbonyl)-doxorubicin, N-(D-alanylphenylalanyllysyl-p-aminobenzyloxycarbonyl-p-aminobenzyloxy-carbonyl)daunorubicin, N-(D-alanylphenylalanyllysyl-p-aminobenzyloxycarbonyl-p-amino-benzyloxycarbonyl-p-aminobenzyloxycarbonyl) daunorubicin, N-(D-alanylphenylalanyllysyl-p-aminobenzyloxycarbonyl-p-aminobenzyloxycarbonyl) mitomycin C, N-(D-alanylphenylalanyllysyl-p-aminobenzyloxycarbonyl-p-aminobenzyloxycarbonyl-p-aminobenzyloxycarbonyl)-mitomycin C, N-(D-alanylphenylalanyllysyl-p-aminobenzyloxycarbonyl-p-aminobenzyloxycarbonyl)-9-aminocamptothecin, N-(D-alanylphenylalanyllysyl-p-aminobenzyloxycarbonyl-p-aminobenzyloxycarbonyl-p-aminobenzyloxycarbonyl)-9-aminocamptothecin, 2'-O-(D-alanylphenylalanyllysyl-p-aminobenzyloxycarbonyl-p-aminobenzyloxycarbonyl) paclitaxel, 2'-O-(D-alanylphenylalanyllysyl-p-aminobenzyloxycarbonyl-p-aminobenzyloxycarbonyl-p-aminobenzyloxycarbonyl)paclitaxel, 7-O-(D-alanylphenylalanyllysyl-p-aminobenzyloxycarbonyl-p-aminobenzyloxycarbonyl)paclitaxel, 7-O-(D-alanylphenylalanyllysyl-p-aminobenzyloxycarbonyl-p-aminobenzyloxycarbonyl-p-aminobenzyloxycarbonyl) paclitaxel, 2'-O-(D-alanylphenylalanyllysyl-p-aminobenzyloxycarbonyl-p-aminobenzyloxycarbonyl) docetaxel, 2'-O-(D-alanylphenylalanyllysyl-p-aminobenzyloxycarbonyl-p-aminobenzyloxycarbonyl-p-aminobenzyloxycarbonyl)docetaxel, 7-O-(D-alanylphenylalanyllysyl-p-aminobenzyloxycarbonyl-p-aminobenzyloxycarbonyl)docetaxel, 7-O-(D- alanylphenylalanyllysyl-p-aminobenzyloxycarbonyl-p-aminobenzyloxycarbonyl-p-aminobenzyloxycarbonyl)docetaxel, O-(D-alanylphenylalanyllysyl-p-aminobenzyloxycarbonyl-p-aminobenzyloxycarbonyl)camptothecin, O-(D-alanylphenylalanyllysyl-p-aminobenzyloxycarbonyl-p-aminobenzyloxycarbonyl-p-aminobenzyloxycarbonyl)camptothecin, O-(D-alanylphenylalanyllysyl-p-aminobenzyloxycarbonyl-p-aminobenzyloxycarbonyl)-9-aminocamptothecin, O-(D-alanylphenylalanyllysyl-p-aminobenzyloxycarbonyl-p-aminobenzyloxycarbonyl-p-aminobenzyloxycarbonyl)-9-aminocamptothecin, O-(D-alanylphenylalanyllysyl-p-aminobenzyloxycarbonyl-p-aminobenzyloxycarbonyl)etoposide, O-(D-alanylphenylalanyllysyl-p-aminobenzyloxycarbonyl-p-aminobenzyloxycarbonyl-p-aminobenzyloxycarbonyl)etoposide, O-(D-alanylphenylalanyllysyl-p-aminobenzyloxycarbonyl-p-aminobenzyloxycarbonyl)irinotecan, O-(D-alanylphenylalanyllysyl-p-aminobenzyloxycarbonyl-p-aminobenzyloxycarbonyl-p-aminobenzyloxycarbonyl)irinotecan, O-(D-alanylphenylalanyllysyl-p-aminobenzyloxycarbonyl-p-aminobenzyloxycarbonyl)topotecan, O-(D-alanylphenylalanyllysyl-p-aminobenzyloxycarbonyl-p-aminobenzyloxycarbonyl-p-aminobenzyloxycarbonyl)topotecan, N-(D-alanylphenylalanyllysyl-p-aminocinnamyloxy-carbonyl-p-aminobenzyloxycarbonyl)doxorubicin, N-(D-alanylphenylalanyllysyl-p-aminocinnamyloxycarbonyl-p-aminobenzyloxycarbonyl)daunorubicin, N-(D-alanylphenylalanyllysyl-p-aminocinnamyloxycarbonyl-p-aminobenzyloxycarbonyl)mitomycin C, N-(D-alanylphenylalanyllysyl-p-aminocinnamyloxycarbonyl-p-aminobenzyloxycarbonyl)-9-aminocamptothecin, 2'-O-(D-alanylphenylalanyllysyl-p-aminocinnamyloxycarbonyl-p-aminobenzyloxycarbonyl)paclitaxel, 7-O-(D-alanylphenylalanyllysyl-p-aminocinnamyloxycarbonyl-p-aminobenzyloxycarbonyl)paclitaxel, 2'-O-(D-alanylphenylalanyllysyl-p-aminocinnamyloxycarbonyl-p-aminobenzyloxycarbonyl)docetaxel, 7-O-(D-alanylphenylalanyllysyl-p-aminocinnamyloxycarbonyl-p-aminobenzyloxycarbonyl)docetaxel, O-(D-alanylphenylalanyllysyl-p-aminocinnamyl-oxycarbonyl-p-aminobenzyloxycarbonyl)camptothecin, O-(D-alanylphenylalanyllysyl-p-amino-cinnamyloxycarbonyl-p-aminobenzyloxycarbonyl)-9-aminocamptothecin, O-(D-alanylphenylalanyllysyl-p-aminocinnamyloxycarbonyl-p-aminobenzyloxycarbonyl)etoposide, O-(D-alanylphenylalanyllysyl-p-aminocinnamyloxycarbonyl-p-aminobenzyloxycarbonyl)irinotecan, O-(D-alanylphenylalanyllysyl-p-aminocinnamyloxycarbonyl-p-aminobenzyloxycarbonyl)topotecan, N-(D-alanylphenylalanyllysyl-p-aminocinnamyloxycarbonyl-p-aminocinnamyloxycarbonyl)doxorubicin, N-(D-alanylphenylalanyllysyl-p-amino-cinnamyloxycarbonyl-p-aminocinnamyloxycarbonyl)daunorubicin, N-(D-alanylphenylalanyllysyl-p-aminocinnamyloxycarbonyl-p-aminocinnamyloxycarbonyl)mitomycin C, N-(D-alanylphenylalanyllysyl-p-aminocinnamyloxycarbonyl-p-aminocinnamyloxycarbonyl)-9-aminocamptothecin, 2'-O-(D-alanylphenylalanyllysyl-p-aminocinnamyloxycarbonyl-p-aminocinnamyloxycarbonyl)paclitaxel, 7-O-(D-alanylphenylalanyllysyl-p-aminocinnamyloxycarbonyl-p-aminocinnamyloxycarbonyl)paclitaxel, 2'-O-(D-alanylphenylalanyllysyl-p-amino-cinnamyloxycarbonyl-p-aminocinnamyloxycarbonyl)docetaxel, 7-O-(D-alanylphenylalanyllysyl-p-aminocinnamyloxycarbonyl-p-aminocinnamyloxycarbonyl)docetaxel, O-(D-alanylphenylalanyllysyl-p-aminocinnamyloxycarbonyl-p-aminocinnamyloxycarbonyl)camptothecin, O-(D-alanylphenylalanyllysyl-p-aminocinnamyloxycarbonyl-p-aminocinnamyloxycarbonyl)-9-aminocamptothecin, O-(D-alanylphenylalanyllysyl-p-aminocinnamyloxycarbonyl-p-aminocinnamyloxycarbonyl)etoposide, O-(D-alanylphenylalanyllysyl-p-aminocinnamyloxycarbonyl-p-aminocinnamyloxycarbonyl)irinotecan, O-(D-alanylphenylalanyllysyl-p-aminocinnamyl-oxycarbonyl-p-aminocinnamyloxycarbonyl)topotecan, 2'-O-(D-alanylphenylalanyllysyl-p-aminobenzyloxycarbonyl(methylamino)ethyl(methylamino)carbonyl)paclitaxel, 7-O-(D-alanylphenylalanyllysyl-p-aminobenzyloxycarbonyl(methylamino)ethyl(methylamino)carbonyl)paclitaxel, 2'-O-(D-alanylphenylalanyllysyl-p-aminobenzyloxycarbonyl(methylamino)ethyl(methylamino)carbonyl)docetaxel, 7-O-(D-alanylphenylalanyllysyl-p-aminobenzyloxycarbonyl(methylamino)ethyl(methylamino)carbonyl)-docetaxel, O-(D-alanylphenylalanyllysyl-p-aminobenzyloxycarbonyl(methylamino)ethyl(methylamino)carbonyl)camptothecin, O-(D-alanylphenylalanyllysyl-p-aminobenzyloxycarbonyl(methylamino)ethyl(methylamino)carbonyl)-9-aminocamptothecin, O-(D-alanylphenylalanyllysyl-p-aminobenzyloxycarbonyl(methylamino)ethyl(methylamino)carbonyl)etoposide, O-(D-alanylphenylalanyllysyl-p-aminobenzyloxycarbonyl(methylamino)ethyl(methylamino)carbonyl)irinotecan, O-(D-alanylphenylalanyllysyl-p-aminobenzyloxycarbonyl(methylamino)ethyl(methylamino)carbonyl)topotecan, 2'-O-(D-alanylphenylalanyllysyl-p-aminocinnamyloxycarbonyl(methylamino)ethyl(methylamino)carbonyl)paclitaxel, 7-O-(D-alanylphenylalanyllysyl-p-aminocinnamyloxycarbonyl(methylamino)ethyl(methylamino)carbonyl)paclitaxel, 2'-O-(D-alanylphenylalanyllysyl-p-aminocinnamyloxycarbonyl(methylamino)ethyl(methylamino)carbonyl)docetaxel, 7-O-(D-alanylphenylalanyllysyl-p-aminocinnamyloxycarbonyl(methylamino)ethyl(methylamino)carbonyl)docetaxel, O-(D-alanylphenylalanyllysyl-p-aminocinnamyloxycarbonyl(methylamino)ethyl(methylamino)carbonyl)camptothecin, O-(D-alanylphenylalanyllysyl-p-aminocinnamyloxycarbonyl(methylamino)ethyl(methylamino)carbonyl)-9-aminocamptothecin, O-(D-alanylphenylalanyllysyl-p-aminocinnamyloxycarbonyl(methylamino)ethyl(methylamino)carbonyl)etoposide, O-(D-alanylphenylalanyllysyl-p-aminocinnamyloxycarbonyl(methylamino)ethyl(methylamino)carbonyl)irinotecan, O-(D-alanylphenylalanyllysyl-p-aminocinnamyloxycarbonyl(methylamino)ethyl(methylamino)carbonyl)topotecan, 2'-O-(D-alanylphenylalanyllysyl-p-aminobenzyloxycarbonyl-p-aminobenzyloxycarbonyl(methylamino)ethyl(methylamino)carbonyl)paclitaxel, 7-O-(D-alanylphenylalanyllysyl-p-aminobenzyloxycarbonyl-p-aminobenzyloxycarbonyl(methylamino)ethyl(methylamino)carbonyl)paclitaxel, 2'-O-(D-alanylphenylalanyllysyl-p-aminobenzyloxycarbonyl-p-aminobenzyloxycarbonyl(methylamino)ethyl(methylamino)carbonyl)docetaxel, 7-O-(D-alanylphenylalanyllysyl-p-aminobenzyloxycarbonyl-p-aminobenzyloxycarbonyl(methylamino)ethyl(methylamino)carbonyl)docetaxel, O-(D-alanylphenylalanyllysyl-p-aminobenzyloxycarbonyl-p-aminobenzyloxycarbonyl(methylamino)ethyl(methylamino)carbonyl)camptothecin, O-(D-alanylphenylalanyllysyl-p-aminobenzyloxycarbonyl-p-aminobenzyloxycarbonyl(methylamino)ethyl(methylamino)carbonyl)-9-aminocamptothecin, O-(D-alanylphenylalanyllysyl-p-aminobenzyloxycarbonyl-p-aminobenzyloxycarbonyl(methylamino)ethyl(methylamino)carbonyl)etoposide, O-(D-alanylphenylalanyllysyl-p-aminobenzyloxycarbonyl-p-aminobenzyloxycarbonyl(methylamino)ethyl(methylamino)carbonyl)irinotecan, O-(D-alanylphenylalanyllysyl-p-aminobenzyloxycarbonyl-p-aminobenzyloxycarbonyl(methylamino)ethyl(methylamino)carbonyl)topotecan, N-(D-valylleucyllysyl-p-aminobenzyloxycarbonyl-p-aminobenzyloxy-carbonyl)doxorubicin, N-(D-valylleucyllysyl-p-aminobenzyloxycarbonyl-p-aminobenzyloxy-carbonyl-p-aminobenzyloxycarbonyl)doxorubicin, N-(D-valylleucyllysyl-p-aminobenzyloxy-carbonyl-p-aminobenzyloxycarbonyl)daunorubicin, N-(D-valylleucyllysyl-p-aminobenzyloxy-carbonyl-p-aminobenzyloxycarbonyl-p-aminobenzyloxycarbonyl)daunorubicin, N-(D-valylleucyllysyl-p-aminobenzyloxycarbonyl-p-aminobenzyloxycarbonyl)mitomycin C, N-(D-valylleucyllysyl-p-aminobenzyloxycarbonyl-p-aminobenzyloxycarbonyl-p-aminobenzyloxycarbonyl)mitomycin C, N-(D-valylleucyllysyl-p-aminobenzyloxycarbonyl-p-aminobenzyl-oxycarbonyl)-9-aminocamptothecin, N-(D-valylleucyllysyl-p-aminobenzyloxycarbonyl-p-aminobenzyloxycarbonyl-p-aminobenzyloxycarbonyl)-9-aminocamptothecin, 2'-O-(D-valylleucyllysyl-p-aminobenzyloxycarbonyl-p-aminobenzyloxycarbonyl)paclitaxel, 2'-O-(D-valylleucyllysyl-p-aminobenzyloxycarbonyl-p-aminobenzyloxycarbonyl-p-aminobenzyloxy-carbonyl)paclitaxel, 7-O-(D-valylleucyllysyl-p-aminobenzyloxycarbonyl-p-aminobenzyloxy-carbonyl)paclitaxel, 7-O-(D-valylleucyllysyl-p-aminobenzyloxycarbonyl-p-aminobenzyloxy-carbonyl-p-aminobenzyloxycarbonyl)paclitaxel, 2'-O-(D-valylleucyllysyl-p-aminobenzyloxy-carbonyl-p-aminobenzyloxycarbonyl)docetaxel, 2'-O-(D-valylleucyllysyl-p-aminobenzyloxy-carbonyl-p-aminobenzyloxycarbonyl-p-aminobenzyloxycarbonyl)docetaxel, 7-O-(D-valyl-leucyllysyl-p-aminobenzyloxycarbonyl-p-aminobenzyloxycarbonyl)docetaxel, 7-O-(D-valylleucyllysyl-p-aminobenzyloxycarbonyl-p-aminobenzyloxycarbonyl-p-aminobenzyloxycarbonyl)docetaxel, O-(D-valylleucyllysyl-p-aminobenzyloxycarbonyl-p-aminobenzyloxycarbonyl)camptothecin, O-(D-valylleucyllysyl-p-aminobenzyloxycarbonyl-p-aminobenzyloxycarbonyl-p-aminobenzyloxycarbonyl)camptothecin, O-(D-valylleucyllysyl-p-aminobenzyl-oxycarbonyl-p-aminobenzyloxycarbonyl)-9-aminocamptothecin, O-(D-valylleucyllysyl-p-aminobenzyloxycarbonyl-p-aminobenzyloxycarbonyl-p-aminobenzyloxycarbonyl)-9-amino-camptothecin, O-(D-valylleucyllysyl-p-aminobenzyloxycarbonyl-p-aminobenzyloxycarbonyl)-etoposide, O-(D-valylleucyllysyl-p-aminobenzyloxycarbonyl-p-aminobenzyloxycarbonyl-p-aminobenzyloxycarbonyl)etoposide, O-(D-valylleucyllysyl-p-aminobenzyloxycarbonyl-p-aminobenzyloxycarbonyl)irinotecan, O-(D-valylleucyllysyl-p-aminobenzyloxycarbonyl-p-aminobenzyloxycarbonyl-p-aminobenzyloxycarbonyl)irinotecan, O-(D-valylleucyllysyl-p-aminobenzyloxycarbonyl-p-aminobenzyloxycarbonyl)topotecan, O-(D-valylleucyllysyl-p-aminobenzyloxycarbonyl-p-aminobenzyloxycarbonyl-p-aminobenzyloxycarbonyl)topotecan, N-(D-valylleucyllysyl-p-aminocinnamyloxycarbonyl-p-aminobenzyloxycarbonyl)doxorubicin, N-(D-valylleucyllysyl-p-aminocinnamyloxycarbonyl-p-aminobenzyloxycarbonyl)daunorubicin, N-(D-valylleucyllysyl-p-aminocinnamyloxycarbonyl-p-aminobenzyloxycarbonyl)mitomycin C, N-(D-valylleucyllysyl-p-aminocinnamyloxycarbonyl-p-aminobenzyloxycarbonyl)-9-aminocamptothecin, 2'-O-(D-valylleucyllysyl-p-aminocinnamyloxycarbonyl-p-aminobenzyloxycarbonyl)paclitaxel, 7-O-(D-valylleucyllysyl-p-aminocinnamyloxycarbonyl-p-aminobenzyloxycarbonyl)paclitaxel, 2'-O-(D-valylleucyllysyl-p-aminocinnamyloxycarbonyl-p-aminobenzyloxycarbonyl)docetaxel, 7-O-(D-valylleucyllysyl-p-aminocinnamyloxycarbonyl-p-aminobenzyloxycarbonyl)docetaxel, O-(D-valylleucyllysyl-p-aminocinnamyloxycarbonyl-p-aminobenzyloxycarbonyl)camptothecin, O-(D-valylleucyllysyl-p-aminocinnamyloxycarbonyl-p-aminobenzyloxycarbonyl)-9-aminocamptothecin, O-(D-valylleucyllysyl-p-aminocinnamyloxycarbonyl-p-aminobenzyloxycarbonyl)etoposide, O-(D-valylleucyllysyl-p-aminocinnamyloxycarbonyl-p-aminobenzyloxycarbonyl)irinotecan, O-(D-valylleucyllysyl-p-aminocinnamyloxycarbonyl-p-aminobenzyloxycarbonyl)topotecan, N-(D-valylleucyllysyl-p-aminocinnamyloxycarbonyl-p-aminocinnamyloxycarbonyl)doxorubicin, N-(D-valylleucyllysyl-p-aminocinnamyloxycarbonyl-p-aminocinnamyloxycarbonyl)daunorubicin, N-(D-valylleucyllysyl-p-aminocinnamyloxycarbonyl-p-aminocinnamyloxycarbonyl)mitomycin C, N-(D-valylleucyllysyl-p-aminocinnamyloxycarbonyl-p-aminocinnamyloxycarbonyl)-9-amino-camptothecin, 2'-O-(D-valylleucyllysyl-p-aminocinnamyloxycarbonyl-p-aminocinnamyloxycarbonyl)paclitaxel, 7-O-(D-valylleucyllysyl-p-aminocinnamyloxycarbonyl-p-aminocinnamyloxycarbonyl)paclitaxel, 2'-O-(D-valylleucyllysyl-p-aminocinnamyloxycarbonyl-p-aminocinnamyloxycarbonyl)docetaxel, 7-O-(D-valylleucyllysyl-p-aminocinnamyloxycarbonyl-p-aminocinnamyloxycarbonyl)docetaxel, O-(D-valylleucyllysyl-p-aminocinnamyloxycarbonyl-p-aminocinnamyloxycarbonyl)camptothecin, O-(D-valylleucyllysyl-p-aminocinnamyloxycarbonyl-p-aminocinnamyloxycarbonyl)-9-aminocamptothecin, O-(D-valylleucyllysyl-p-aminocinnamyloxycarbonyl-p-aminocinnamyloxycarbonyl)etoposide, O-(D-valylleucyllysyl-p-aminocinnamyloxycarbonyl-p-aminocinnamyloxycarbonyl)irinotecan, O-(D-valylleucyllysyl-p-aminocinnamyloxycarbonyl-p-aminocinnamyloxycarbonyl)topotecan, 2'-O-(D-valylleucyllysyl-p-aminobenzyloxycarbonyl(methylamino)ethyl(methylamino)carbonyl)paclitaxel, 7-O-(D-valylleucyllysyl-p-aminobenzyloxycarbonyl(methylamino)ethyl(methylamino)carbonyl)paclitaxel, 2'-O-(D-valylleucyllysyl-p-aminobenzyloxycarbonyl(methylamino)ethyl(methylamino)carbonyl)docetaxel, 7-O-(D-valylleucyllysyl-p-aminobenzyloxycarbonyl(methylamino)ethyl(methylamino)carbonyl)docetaxel, O-(D-valylleucyllysyl-p-aminobenzyloxycarbonyl(methylamino)ethyl(methylamino)carbonyl)camptothecin, O-(D-valylleucyllysyl-p-aminobenzyloxycarbonyl(methylamino)ethyl(methylamino)carbonyl)-9-aminocamptothecin, O-(D-valylleucyllysyl-p-aminobenzyloxycarbonyl(methylamino)ethyl(methylamino)carbonyl)etoposide, O-(D-valylleucyllysyl-p-aminobenzyloxycarbonyl(methylamino)ethyl(methylamino)carbonyl)irinotecan, O-(D-valylleucyllysyl-p-aminobenzyloxycarbonyl(methylamino)ethyl(methylamino)carbonyl)topotecan, 2'-O-(D-valylleucyllysyl-p-aminocinnamyloxycarbonyl(methylamino)ethyl(methylamino)carbonyl)paclitaxel, 7-O-(D-valylleucyllysyl-p-aminocinnamyloxycarbonyl (methylamino)ethyl(methylamino)carbonyl)-paclitaxel, 2'-O-(D-valylleucyllysyl-p-aminocinnamyloxycarbonyl (methylamino)ethyl(methylamino)carbonyl)docetaxel, 7-O-(D-valylleucyllysyl-p-aminocinnamyloxycarbonyl-(methylamino)ethyl(methylamino)carbonyl)docetaxel, O-(D-valylleucyllysyl-p-aminocinnamyloxycarbonyl (methylamino)ethyl(methylamino)carbonyl)camptothecin, O-(D-valylleucyllysyl-p-aminocinnamyloxycarbonyl(methylamino)ethyl(methylamino)carbonyl)-9-aminocamptothecin, O-(D-valylleucyllysyl-p-aminocinnamyloxycarbonyl (methylamino)ethyl(methylamino)carbonyl)etoposide, O-(D-valylleucyllysyl-p-aminocinnamyloxycarbonyl(methylamino)ethyl(methylamino)carbonyl)irinotecan, O-(D-valylleucyllysyl-p-aminocinnamyloxycarbonyl(methylamino)ethyl(methylamino)carbonyl)topotecan, 2'-O-(D-valylleucyllysyl-p-aminobenzyloxycarbonyl-p-aminobenzyloxycarbonyl(methylamino)ethyl (methylamino)carbonyl)paclitaxel, 7-O-(D-valylleucyllysyl-p-aminobenzyloxycarbonyl-p-aminobenzyloxycarbonyl(methylamino)ethyl (methylamino)carbonyl)paclitaxel, 2'-O-(D-valylleucyllysyl-p-aminobenzyloxycarbonyl-p-aminobenzyloxycarbonyl(methylamino)ethyl (methylamino)carbonyl)docetaxel, 7-O-(D-valylleucyllysyl-p-aminobenzyloxycarbonyl-p-aminobenzyloxycarbonyl(methylamino)ethyl (methylamino)carbonyl)docetaxel, O-(D-valylleucyllysyl-p-aminobenzyloxycarbonyl-p-aminobenzyloxycarbonyl (methylamino)ethyl(methylamino)carbonyl)camptothecin, O-(D-valylleucyllysyl-p-aminobenzyloxycarbonyl-p-aminobenzyloxycarbonyl(methylamino)ethyl(methylamino) carbonyl)-9-aminocamptothecin, O-(D-valylleucyllysyl-p-aminobenzyloxycarbonyl-p-aminobenzyloxycarbonyl (methylamino)ethyl(methylamino)carbonyl)etoposide, O-(D-valylleucyllysyl-p-aminobenzyloxycarbonyl-p-aminobenzyloxycarbonyl(methylamino)ethyl(methylamino) carbonyl)irinotecan, O-(D-valyl-leucyllysyl-p-aminobenzyloxycarbonyl-p-aminobenzyloxycarbonyl(methylamino) ethyl(methylamino)carbonyl)topotecan, or a salt thereof.

23. The compound of claim 22 which is N-(D-alanylphenylalanyllysyl-p-aminobenzyloxycarbonyl-p-aminobenzyloxycarbonyl)doxorubicin.

24. The compound of claim 22 which is N-(D-valylleucyllysyl-p-aminobenzyloxycarbonyl-p-aminobenzyloxycarbonyl)doxorubicin.

25. The compound of claim 22 which is 2'-O-(D-alanylphenylalanyllysyl-p-aminobenzyloxycarbonyl(methylamino)ethyl(methylamino)carbonyl)paclitaxel.

26. The compound of claim 22 which is 2'-O-(D-valylleucyllysyl-p-aminobenzyloxycarbonyl(methylamino) ethyl(methylamino)carbonyl)paclitaxel.

27. The compound of claim 22 which is 2'-O-(D-alanylphenylalanyllysyl-p-aminocinnamyloxycarbonyl(methylamino)ethyl(methylamino)carbonyl)paclitaxel.

28. The compound of claim 22 which is 2'-O-(D-valylleucyllysyl-p-aminocinnamyloxycarbonyl(methylamino) ethyl(methylamino)carbonyl)paclitaxel.

29. The compound of claim 1 wherein the moiety Z is an antibiotic, an anti-inflammatory agent, or an anti-viral agent.

30. The compound of claim 1 wherein the specifier V contains a polymer.

31. The compound of claim 1, wherein the specifier V is removed by an enzyme that is transported to the vicinity of target cells or target tissue via antibody-directed enzyme prodrug therapy ("ADEPT"), polymer-directed enzyme prodrug therapy ("PDEPT"), virus-directed enzyme prodrug therapy ("VDEPT") or gene-directed enzyme prodrug therapy ("GDEPT").

32. A process for preparing a pharmaceutical composition in a solid or a liquid formulation for administration orally, topically or by injection, said process comprising mixing a compound according to claim 1 with a pharmaceutically acceptable carrier.

33. A pharmaceutical composition comprising a compound of claim 1 and a pharmaceutically acceptable carrier.

34. The compound of claim 1 wherein the specifier V contains a moiety capable of targeting the compound to the target site by selectively complexing with a receptor or other receptive moiety associated with a target cell population.

35. The compound of claim 1 wherein the specifier V contains an antigen-recognizing immunoglobulin or an antigen-recognizing fragment of an immunoglobulin.

* * * * *